(12) United States Patent
Avram et al.

(10) Patent No.: US 12,109,271 B2
(45) Date of Patent: Oct. 8, 2024

(54) MICROPARTICLE SYSTEMS AND THEIR USE FOR THE TREATMENT OF MULTIPLE SCLEROSIS

(71) Applicant: UNIVERSITY OF FLORIDA RESEARCH FOUNDATION, INCORPORATED, Gainesville, FL (US)

(72) Inventors: Dorina Avram, Tampa, FL (US); Benjamin George Keselowsky, Gainesville, FL (US); Joshua Stewart, Gainesville, FL (US); Jonathan Joseph Cho, Gainesville, FL (US)

(73) Assignee: UNIVERSITY OF FLORIDA RESEARCH FOUNDATION, INCORPORATED, Gainesville, FL (US)

( * ) Notice: Subject to any disclaimer, the term of this patent is extended or adjusted under 35 U.S.C. 154(b) by 936 days.

(21) Appl. No.: 17/257,731

(22) PCT Filed: Jul. 3, 2019

(86) PCT No.: PCT/US2019/040534
§ 371 (c)(1),
(2) Date: Jan. 4, 2021

(87) PCT Pub. No.: WO2020/010221
PCT Pub. Date: Jan. 9, 2020

(65) Prior Publication Data
US 2021/0169904 A1    Jun. 10, 2021

Related U.S. Application Data

(60) Provisional application No. 62/693,619, filed on Jul. 3, 2018.

(51) Int. Cl.
| | | |
|---|---|---|
| A61K 47/59 | (2017.01) | |
| A61K 31/203 | (2006.01) | |
| A61K 31/436 | (2006.01) | |
| A61K 31/593 | (2006.01) | |
| A61K 38/18 | (2006.01) | |
| A61K 38/19 | (2006.01) | |
| A61K 38/20 | (2006.01) | |
| A61K 39/00 | (2006.01) | |
| A61P 25/00 | (2006.01) | |

(52) U.S. Cl.
CPC .......... *A61K 47/593* (2017.08); *A61K 31/203* (2013.01); *A61K 31/436* (2013.01); *A61K 31/593* (2013.01); *A61K 38/1841* (2013.01); *A61K 38/1866* (2013.01); *A61K 38/193* (2013.01); *A61K 38/2066* (2013.01); *A61K 39/0008* (2013.01); *A61P 25/00* (2018.01)

(58) Field of Classification Search
CPC ...... A61K 2039/55555; A61K 2300/00; A61K 38/193; A61K 38/2066; A61K 47/593; A61K 9/0019; A61K 9/1647; A61K 45/06; A61K 9/0021; A61K 31/593; A61K 2039/622; A61K 38/18; A61K 38/1841; A61K 9/1635; A61K 31/436; A61K 47/6937; A61P 37/02
See application file for complete search history.

(56) References Cited

U.S. PATENT DOCUMENTS

2021/0169904 A1    6/2021    Avram et al.

FOREIGN PATENT DOCUMENTS

| WO | 2010147484 A1 | 12/2010 |
| WO | 2018013625 A1 | 1/2018 |
| WO | 2020010221 A1 | 1/2020 |

OTHER PUBLICATIONS

PCT/US2019/40534, Search Report and Written Opinion, Mailed Date Jul. 3, 2019, 11 pages.
Arnon, R. et al., "Mechanism of action of glatiramer acetate in multiple sclerosis and its potential for the development of new applications," Proc. Natl. Acad. Sci. U.S.A. 101 (Suppl 2) (2004) 14593e14598.
Bettelli, E. et al., "Loss of T-bet, But Not STAT1, Prevents the Development of Experimental Autoimmune Encephalomyelitis," J. Exp. Med. 200 (1) (2004) 79e87.
Bielekova, B. et al., "Expansion and functional relevance of high-avidity myelin-specific CD4 T cells in multiple sclerosis," J. Immunol. 172(6) (2004) 3893e3904.
Brickshawana, A. et al., "Investigation of Kir4.1 potassium channel as putative antigen of multiple sclerosis: a cohort study," Lancet Neurol. 13, 795-806 (2014).
Califano, D. et al., "Diverting T helper cell trafficking through increased plasticity attenuates autoimmune encephalomyelitis," J. Clin. Invest 124(1) (2014) 174e187.
Califano, D. et al., Transcription factor Bcl11b controls identity and function of mature innate lymphoid cells type II, Immunity 43 (2) (2015) 354e368.

(Continued)

*Primary Examiner* — Bao Q Li
(74) *Attorney, Agent, or Firm* — Timothy H. Van Dyke; Wolter, Van Dyke, Davis, PLLC

(57) ABSTRACT

Provided are a dual microparticle system to treat Multiple Sclerosis, the system comprising phagocytosable and non-phagocytosable microparticles for delivery of at least one antigen, at least one immunomodulatory agent, at least one immunosuppressive agent and at least one chemoattractant to a subject suffering from Multiple Sclerosis to generate tolerogenic dendritic cells in the subject and treat the Multiple Sclerosis.

16 Claims, 18 Drawing Sheets

Specification includes a Sequence Listing.

(56) References Cited

OTHER PUBLICATIONS

Codarri, L. et al., "Communication between pathogenic T cells and myeloid cells in neuroinflammatory disease," Trends Immunol. 34(3) (2013) 114e119.

Codarri, L. et al., "RORyt drives production of the cytokine GM-CSF in helper T cells, which is essential for the effector phase of autoimmune neuroinflammation," Nature Immunology, Apr. 24, 2011, 12(6):560-567.

Cohen, J. MD et al., "Mechanisms of fingolimod's efficacy and adverse effects in multiple sclerosis," Ann. Neurol. 69(5) (2011) 759e777—Abstract Only.

Compston, A. et al., "Multiple sclerosis," Seminar, The Lancet, vol. 372, Issue 9648, P1502-1517, Oct. 25, 2008.

Dendrou, C. et al., "Immunopathology of multiple sclerosis," Nature Reviews Immunology vol. 15, pp. 545-558 (2015).

El-Behi, M. et al., "The encephalitogenicity of TH17 cells is dependent on IL-1- and IL-23-induced production of the cytokine GM-CSF," Nat. Immunol. 12(6) (2011) 568e575.

Fox, R. et al., "Placebo-Controlled Phase 3 Study of Oral BG-12 or Glatiramer in Multiple Sclerosis," N. Engl. J. Med. 367(12) (2012) 1087e1097.

Goodin, D. et al., "Assessment: The use of natalizumab (Tysabri) for the treatment of multiple sclerosis (an evidence-based review) Report of the Therapeutics and Technology Assessment Subcommittee of the American Academy of Neurology," Neurology 71(10) (2008) 766e773.

Goodin, D. et al., "Disease modifying therapies in multiple sclerosis Report of the Therapeutics and Technology Assessment Subcommittee of the American Academy of Neurology and the MS Council for Clinical Practice Guidelines," Neurology 58(2) (2002) 169e178.

Hellings, N. et al., "T-cell reactivity to multiple myelin antigens in multiple sclerosis patients and healthy controls," J. Neurosci. Res. 63(3) (2001) 290e302.

Hirota, K. et al., "Fate mapping of IL-17-producing T cells in inflammatory responses," Nat. Immunol. 12(3) (2011) 255e263.

Hunter, Z. et al., "A Biodegradable Nanoparticle Platform for the Induction of Antigen-Specific Immune Tolerance for Treatment of Autoimmune Disease," ACS nano 8(3) (2014) 2148e2160.

Ivanov, I. et al., "The orphan nuclear receptor RORgammat directs the differentiation program of proinflammatory IL-17 + T helper cells," Cell 126(6) (2006) 1121e1133.

Jaeger, A. et al., "Th1, Th17, and Th9 effector cells induce experimental autoimmune encephalomyelitis with different pathological phenotypes," J. Immunol. 183(11) (2009) 7169e7177.

Kobelt, G. et al., "Costs and quality of life in multiple sclerosis A cross-sectional study in the United States," Neurology 66 (11) (2006) 1696e1702—Abstract Only.

Langrish, C. et al., "IL-23 drives a pathogenic T cell population that induces autoimmune inflammation," J. Exp. Med. 201(2) (2005) 233e240.

Kwiatkowski, A.et al., "Nano and Microparticle Emerging Strategies for Treatment of Autoimmune Diseases: Multiple Sclerosis and Type 1 Diabetes," Adv. Healthcare Mater. 2020, 9, 2000164, 11 pages.

Lee, Y. et al., "Induction and molecular signature of pathogenic TH17 cells," Nat. Immunol. 13(10) (2012) 991e999.

Lewis, J.S. et al., "A combination dual-sized microparticle system modulates dendritic cells and prevents type 1 diabetes in prediabetic NOD mice," Clin. Immunol. 160(1) (2015) 90e102.

Lublin, F.D. et al., "Defining the clinical course of multiple sclerosis: the 2013 revisions," Neurology 83 (3) (2014) 278e286.

Mayuzumi, N. et al., "IL-33 Promotes DC Development in BM Culture by Triggering GM-CSF Production," Eur. J. Immunol. 39(12) (2009) 3331e3342.

Mosser, D.M. et al., "Exploring the full spectrum of macrophage activation," Nat. Rev. Immunol. 8(12) (2008) 958e969.

Nylander, A. et al.,"Multiple sclerosis," J. Clin. Invest 122 (4) (2012) 1180e1188.

Park, H. et al., "A distinct lineage of CD4 T cells regulates tissue inflammation by producing interleukin 17," Nat. Immunol. 6(11) (2005) 1133e1141.

Pino, P. et al., "Isolation of Brain and Spinal Cord Mononuclear Cells Using Percoll Gradients," J. Vis. Exp. (48) (2011).—Abstract Only.

Riedhammer, C. et al., "Antigen presentation, autoantigens, and immune regulation in multiple sclerosis and other autoimmune diseases," Front Immunol, 6: 322 (2015).

VanValkenburgh, J. et al., "Critical role of Bcl11b in suppressor function of T regulatory cells and prevention of inflammatory bowel disease," J. Exp. Med. 208(10) (2011) 2069e2081.

Weiner, "H.L. , Multiple sclerosis is an inflammatory T-cell-mediated autoimmune disease", Arch. Neurol. 61 (10) (2004) 1613e1615.

Wingerchuk, D.M. et al., "Multiple sclerosis: current and emerging disease-modifying therapies and treatment strategies," Mayo Clin. Proc. 89(2) (2014) 225e240.

Xiao, Y. et al., "Peli1 promotes microglia-mediated CNS inflammation by regulating Traf3 degradation," Nat. Med. 19(5) (2013) 595e602.

Yang, Y. et al.,"T-bet is essential for encephalitogenicity of both Th1 and Th17 cells," J. Exp. Med. 206(7) (2009) 1549e1564.

Yeste, A. et al., "Nanoparticle-mediated codelivery of myelin antigen and a tolerogenic small molecule suppresses experimental autoimmune encephalomyelitis," Proc. Natl. Acad. Sci. U.S.A. 109(28) (2012) 11270e11275.

Cho, J. et al., "An antigen-specific semi-therapeutic treatment with local delivery of tolerogenic factors through a dual-sized microparticle system blocks experimental autoimmune encephalomyelitis," Biomaterials 143, pp. 79-82 (2017) 79e92.

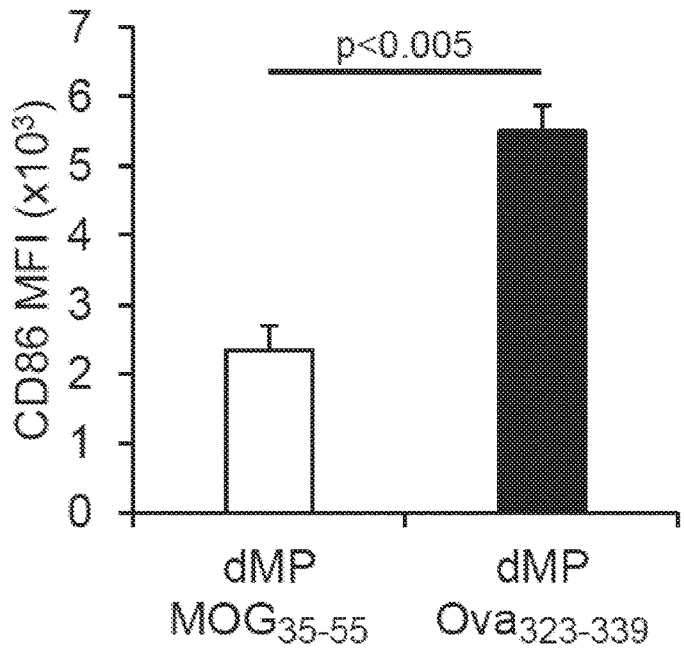

FIG. 10C

| Description | Sequence | aa | $M_r$ |
|---|---|---|---|
| $MBP_{13-32}$ | KYLATASTMDHARHGFLPRH | 20 | 2351.1 |
| $MBP_{83-99}$ | ENPVVHFFKNIVTPRTP | 17 | 2036.3 |
| $MBP_{111-129}$ | LSRFSWGAEGQRPGFYGG | 19 | 2070.6 |
| $MBP_{131-155}$ | ASDYKSAHKGLKGVDAQGTLSKIFK | 25 | 2691.1 |
| $MBP_{146-170}$ | AQGTLSKIFKLGGRDSRSGSPMARR | 25 | 2718.2 |
| $PLP_{40-60}$ | TGTEKLIETYFSKNYQDYEYL | 21 | 2647.0 |
| $PLP_{89-106}$ | GFYTTGAVRQIFGDYKTT | 18 | 2066.5 |
| $PLP_{139-154}$ | HCLGKWLGHPDKFVGI | 16 | 1848.6 |
| $PLP_{178-197}$ | NTWTTCQSIAFPSKTSASIG | 20 | 2141.6 |
| $PLP_{190-208}$ | SKTSASIGSLCADARMYGVLP | 20 | 2071.8 |
| $MOG_{1-20}$ | GQFRVIGPRHPIRALVGDEV | 20 | 2215.8 |
| $MOG_{11-30}$ | PIRALVGDEVELPCRISPGK | 20 | 2190.8 |
| $MOG_{35-55}$ | MEVGWYRPPFSRVVHLYRNGK | 21 | 2633.2 |
| $CNP_{343-373}$ | EVGELSRGKLYSLGNGRWMLTLAKNMEVRAI | 31 | 3534.2 |
| $CNP_{356-388}$ | GNGRWMLTLAKNMEVRAIFTGYYGKGKPVPTQG | 33 | 3683.4 |

FIG. 11

MICROPARTICLE SYSTEMS AND THEIR USE FOR THE TREATMENT OF MULTIPLE SCLEROSIS

GOVERNMENT SUPPORT

The subject invention was made with government support under a research project supported by the National Institutes of Health grant number R01AI133623. The government has certain rights in the invention.

BACKGROUND OF THE INVENTION

Autoimmune diseases are frequently associated with a reduction in the number and function of regulatory T cells. These cells are known to suppress the levels of physiologic auto-reactive T cells. When the levels of auto-reactive T cells are elevated pathological destruction of desirable cells can result.

Dendritic cells (DCs) play a critical role in the maintenance of peripheral tolerance. DCs promote $T_{reg}$ induction, thereby suppressing excessive immune responses. Dendritic cell-based vaccines have been demonstrated to promote tolerance through antigen-presenting cells (APCs). APCs process and present self-peptides in a tolerogenic manner to T-cells, and induce $T_{reg}$ proliferation. Apoptotic cells express surface ligands recognized by APCs via surface molecules such as the phosphatidyl serine (PS) receptor, CD 47, CD 36, and $\alpha v\beta_3$. Recent studies imply that these receptors could inhibit DC maturation and induce tolerance.

The present use of dendritic cell-based vaccines, however, suffers from several limitations. For instance, the present approach typically requires ex-vivo manipulation of patients' cells, which can adversely affect patient safety, and is associated with high cost.

The incidence rates of immune-mediated diseases are reaching epidemic proportions in the US, with millions of individuals suffering from autoimmune disorders such as multiple sclerosis (MS), type 1 diabetes, rheumatoid arthritis, and systemic lupus erythematosus, amongst others. No true cure exists for these conditions, posing a significant long-term risk to the affected individual and increasing our society's healthcare burden.

While non-specific immune-suppressive agents remain the current standard-of-care for many autoimmune disorders, such therapies are often associated with significant off-target actions as well as side-effects resulting from their targeting complex pathways. As a result, the biomedical research community has increasingly sought to identify an improved means for inducing specific "immune tolerance" (i.e., failure to respond to self) as an approach to overcome autoimmune disease.

Recently, it has become increasingly clear that changes in the approach to autoimmune disease therapy need to be developed, capitalizing on how the body normally maintains self-tolerance, by harnessing an individual's own immune system. Key to implementing this paradigm shift will be to take advantage of the immune system's reliance on DCs, the professional antigen presenting cell and master-regulator of the immune response.

Tolerogenic DCs maintain antigen-specific T-cell tolerance either directly by inducing anergy, apoptosis, or phenotype skewing or indirectly by induction of regulatory T cells (Tregs). Therefore, therapeutic vaccination approaches for MS utilizing DCs holds great promise to correct antigen-specific autoimmune responses; yet therapies involving exogenous generation and manipulation of DCs possess numerous shortcomings including unsustainable antigen presentation, inefficient homing of DCs to the lymphatic system, and critically high treatment costs from the isolation and storage of DCs.

Multiple sclerosis (MS) is an immune-mediated neurological disease that typically affects young adults with higher prevalence in females [1-3]. MS is a complex inflammatory disease of the central nervous system (CNS) where immune cells target and destroy oligodendrocytes and myelin sheath on nerve cells causing auto-immune demyelination [4,5]. The precise instigating factor(s) that initiates MS remains unknown [4], but it is well established that proinflammatory CD4[+] T cells are important in mediating MS pathogenesis, as well as that of experimental autoimmune encephalomyelitis (EAE), an animal model of MS [6]. Blood circulating CD4[+] T cells from MS patients have been shown to recognize myelin oligodendrocyte glycoprotein (MOG) and myelin basic protein (MBP), two myelin-associated proteins shown to play a role in MS pathogenesis and used as basis for EAE induction [7-9]. Several subsets of proinflammatory CD4[+] T cells have been implicated as crucial drivers of EAE, namely Th17 and Th1 cells. Th17 cells are CD4[+] T cells that express the lineage transcription factor Rorγt and produce the proinflammatory cytokines IL-17A, IL-17F, and, in the setting of EAE, GM-CSF [10-14], while Th1 cells express the lineage transcription factor T-bet and produce the proinflammatory cytokine IFNγ, and were also demonstrated to be important in EAE disease pathogenesis [15]. Defects in Th17 and Th1 cells or GM-CSF production prevented disease in EAE, thus solidifying the central role of proinflammatory CD4[+] T cells and the corresponding cytokines IL-17A, IFNγ, and GM-CSF in EAE [13, 15].

MS does not have a cure and current therapeutic options are limited. In the acute setting of MS exacerbation/relapse, methyl-prednisolone or other corticosteroids are used to provide immunosuppression [16]. Long-term management of MS involves disease-modifying therapies that may be poorly tolerated, inadequate in controlling disease, or incur life-threatening side effects and opportunistic infections [17].

Thus, there is a need for developing alternative vaccine compositions that are effectively delivered to target cells to treat diseases like MS.

SUMMARY

The present invention provides antigen-specific, tolerance-inducing microparticle systems for targeted delivery to immune system cells in order to treat multiple sclerosis (MS).

Antigen-specific treatments are highly desirable for autoimmune diseases in contrast to treatments that induce systemic immunosuppression. The subject invention provides an antigen-specific therapy for the treatment of multiple sclerosis.

The treatment uses dual-sized, polymeric microparticles (dMPs) loaded with specific antigen and tolerizing factors for intra- and extra-cellular delivery, designed to recruit and modulate dendritic cells toward a tolerogenic phenotype without systemic release. This approach demonstrates robust efficacy and provides protection against disease.

In one embodiment, the invention provides a method of inducing antigen-specific immune tolerance in a subject who has MS. The method involves administering a dual microparticle system that targets antigen-presenting immune cells in the subject. One set of microparticles is phagocytosable by the antigen-presenting immune cell of interest, and the other set of microparticles is non-phagocytosable by the antigen-presenting immune cell.

The phagocytosable microparticles together comprise at least one antigen and at least one immunomodulatory agent. The non-phagocytosable microparticles together comprise at least one immunosuppressive tolerogenic agent and at least one agent that recruits the antigen-presenting immune cell of interest.

The immunosuppressive tolerogenic agent can be for example, IL-10, TGF-β, or a nonsteroidal anti-inflammatory drug (NSAID). The recruiting agent can be, for example, GM-CSF, G-CFS, M-CSF, CCL19, CCL20, CCL 21 or VEGF-C.

The composition of the subject invention can further comprise a remyelinating agent selected from clemastine, clobetasol, digoxin, miconazole, phenytoin, and quetiapine; wherein the remyelinating agent is administered in soluble form by intravenous injection or is incorporated into the non-phagocytosable microparticles.

The phagocytosable microparticle and the non-phagocytosable microparticles are made of a biodegradable material.

The therapeutic efficacy of the compositions of the subject invention is improved by encapsulation of the factors in controlled-release microparticles.

BRIEF DESCRIPTION OF THE DRAWINGS

FIG. 1A shows the quantification of microparticle sizes by dynamic light scattering analyses with average sizes of ~0.8 μm for vitamin D3, $MOG_{35-55}$, and $OVA_{323-339}$ MPs, and average ~55 m for TGF-β1 and GM-CSF MPs. FIG. 1B shows the loading amount, encapsulation efficiency, and dose per injection for MPs containing each biological/pharmacological agent.

FIG. 2A shows the subcutaneous dMP injection sites (nodules) in B6 mice excised 8 days after administration and the evaluation for cellular infiltration by hematoxylin and eosin staining; scale bar represents 400 μm. FIG. 2B shows representative flow cytometry analysis of DC recruitment in dMP or unloaded MP nodules. A fluorescence minus one (FMO) control, containing all antibodies except CD11c, was assessed to determine gating of DCs. FIG. 2C shows the total frequency of DCs in respective nodules as a percent of live $CD45^+$ cells. FIG. 2D shows a representative flow cytometry analysis for DC surface expression of co-stimulatory molecule CD86. FIG. 2E shows the total frequency of $CD86^+$ expression on DCs isolated from respective nodules. FIG. 2F shows DC (Lyg6-$CD11c^+$), macrophage (Lyg6-CD11c-$CD11b^+$), and neutrophil ($Lyg6^+$) MP uptake in dMP or unloaded MP nodules as a percentage of total phagocytosed MPs ($CD45^+DiO^+$). FIG. 2G shows inguinal lymph nodes (ILNs) that were excised at 24 and 48 h after dMP injection and analyzed for $dMP^+$ phagocyte populations. FIG. 2H shows PD-L1 expression of DCs isolated from ILNs 24 h after MP injection and analyzed according to dMP or unloaded MP phagocytosis. FIG. 2I shows MHC-II expression of DCs isolated from ILNs 48 h after MP injection and analyzed according to dMP or unloaded MP phagocytosis. FIG. 2J shows the proximal draining lymph nodes (axillary [ALN] and inguinal [ILN]) and distal lymphoid organs (mesenteric lymph nodes [MLN] and spleen) that were excised eight days after dMP injection and analyzed via flow cytometry for MP trafficking. The frequency of $dMP^+$ DCs as a percent of total DCs is characterized in mice that received either no MPs (No Treatment) or the dMP. FIG. 2K shows dMP distribution across phagocyte populations at the eight day time point in proximal draining lymph nodes as a percent of total $dMP^+$ cells. FIG. 2L shows serum TGF-β1 and FIG. 2M shows GM-CSF levels (pg/mL) measured by ELISA from mice without treatment, mice days 2, 4, and 7 after subcutaneous dMP treatment, and mice with intravenous injection of TGF-β1 and GM-CSF immediately prior to blood collection. n=3-5 per group. p values were obtained from Student's t tests (C, E, F, G, and J) or one-way ANOVA with Tukey's post-hoc analysis (H, I, K, L, and M), *=p<0.05, =p<0.01, *=p<0.001, n.s.=p>0.05 (not significant), ND (not detectable).

FIG. 3A shows the EAE disease score (mean±SEM) of B6 mice treated with either dMP $MOG_{35-55}$ (filled circle) or dMP formulation without $MOG_{35-55}$ (unloaded 0.8 μm MP were substituted) (open square) on days 4, 7, and 10 (filled arrows) following EAE induction; n=10 per group. p value was obtained from Student's t-test. FIG. 3B shows the EAE disease score trend of B6 mice treated with either dMP $MOG_{35-55}$ formulation (filled circle) or dMP formulation without $MOG_{35-55}$ (open square) on days 4, 7, and 10 following EAE induction; n=10 per group. p value was obtained from ANOVA.

FIG. 4A shows a representative hematoxylin and eosin staining of spinal cord section from B6 EAE mice treated either with dMP $MOG_{35-55}$ or soluble factors co-administered with empty MPs (S+U MPs); scale bar represents 200 m; n=10 per group. FIG. 4B shows a representative flow cytometry analysis performed on day 21 following EAE induction of live $CD4^+$ and $CD8^+$ T cell frequencies from CNS of mice treated on day 4 following EAE induction either with dMP $MOG_{35-55}$ or S+U MPs; n=5 per group. FIG. 4C shows the absolute numbers of $CD4^+$ T cells in CNS of healthy naïve mice, or on day 21 following EAE induction of mice treated on day 4 following EAE induction either with dMP $MOG_{35-55}$ or S+U MPs. p value was obtained from Student's t-test.

FIG. 5A shows the representative frequencies of $CD4^+$ T cells positive for IL-17A, GM-CSF, IFNγ, and dual cytokines analyzed by intracellular cytokine staining and flow cytometry on day 21 following EAE induction in the brain of EAE mice treated on day 4 following EAE induction either with dMP $MOG_{35-55}$ or S+U MPs; n=5 per group. FIG. 5B shows the absolute numbers of the CNS-infiltrating $CD4^+$ T cells producing the indicated cytokines on day 21 following EAE induction in the brain of EAE mice treated on day 4 following EAE induction either with dMP $MOG_{35-55}$ or S+U MPs; n=5 per group. p value was obtained from Student's t-test.

FIG. 6A shows a representative intranuclear flow cytometry analysis of frequencies of $Rorγt^+$, $T-bet^+$, and $Rorγt^+T-bet+$ $CD4^+$ T cells on day 21 following EAE induction in the brain of EAE mice treated on day 4 following EAE induction either with dMP $MOG_{35-55}$ or S+U MPs; n=5 per group. FIG. 6B shows the absolute numbers of the CNS-infiltrating Rorγt+, T-bet+, and Rorγt+T-bet+CD4+ T cells on day 21 following EAE induction of EAE mice treated on day 4 following EAE induction either with dMP MOG$_{35-55}$ or S+U MPs; n=5 per group. p value was obtained from Student's t-test.

FIG. 7A shows a representative flow cytometry analysis performed on day 21 following EAE induction of leukocytes isolated from CNS of mice treated on day 4 following EAE induction either with dMP MOG$_{35-55}$ or S+U MPs; n=5 per group. FIG. 7B shows the absolute numbers of activated microglia/macrophages on day 21 following EAE induction in CNS of mice treated on day 4 following EAE induction either with dMP MOG$_{35-55}$ or S+U MPs; n=5 per group. Live leukocytes were gated on CD11b+CD11c+CD68+CD45+ and further on F4/80 and CD80 high. p value was obtained from Student's t-test.

FIG. 8A shows the EAE disease score (mean±SEM) of B6 mice treated with either dMP MOG$_{35-55}$ (filled circle) or dMP Ova$_{323-339}$ (open square) on days 4 and 7 (filled arrows) following EAE induction; n=10 per group. p value was obtained from Student's t-test. FIG. 8B shows the EAE disease score trend of B6 mice treated with either dMP MOG$_{35-55}$ (filled circle) or dMP Ova$_{323-339}$ (open square) on days 4 and 7 following EAE induction; n=10 per group. p value was obtained from ANOVA.

FIG. 9A shows a representative flow cytometry analysis of CFSE level in CD4+ T cells isolated on day 21 following EAE induction from draining lymph nodes of B6 mice treated with either dMP MOG$_{35-55}$ (dash line) or dMP Ova$_{35-55}$ (solid line) on days 4 and 7 (filled arrows) following EAE induction after 72 h co-culture with T-cell depleted splenocytes loaded with MOG$_{35-55}$. FIG. 9B shows the frequencies of CFSE negative CD4+ T cells isolated on day 21 following EAE induction from draining lymph nodes of B6 mice treated with either dMP MOG$_{35-55}$ (dash line) or dMP Ova$_{323-339}$ (solid line) on days 4 and 7 (filled arrows) following EAE induction after 72 h co-culture with T-cell depleted splenocytes loaded with MOG$_{35-55}$. p value was obtained from Student's t-test.

FIGS. 10A-10C show that dendritic cells from draining lymph nodes of EAE mice treated with dMP-MOG$_{35-55}$ displayed a tolerized phenotype. FIG. 10A shows a representative flow cytometry analysis of CD86 and MHCII expression on CD11b+CD11c+ dendritic cells isolated on days 13 and 25 from draining lymph nodes of mice treated on day 4 and 7 following EAE induction either with dMP MOG$_{35-55}$ or dMP Ova$_{323-339}$; n=4 per group. FIG. 10B shows the frequency of CD86$^{hi}$MHCII$^{hi}$CD11b+CD11c+ dendritic cells isolated on days 13 and 25 from draining lymph nodes of mice treated on day 4 and 7 following EAE induction either with dMP MOG$_{35-55}$ or dMP Ova$_{323-339}$; n=4 per group.

FIG. 10C shows the mean fluorescence intensity of CD86 in CD11b+CD11c+ dendritic cells isolated on days 13 and 25 from draining lymph nodes of mice treated on day 4 and 7 following EAE induction either with dMP MOG$_{35-55}$ or dMP Ova$_{323-339}$; n=4 per group. p value was obtained from Student's t-test.

FIG. 11 shows sequences of antigens included in the microparticles of the subject invention.

BRIEF DESCRIPTION OF SEQUENCES

Figures 1A, 1B:
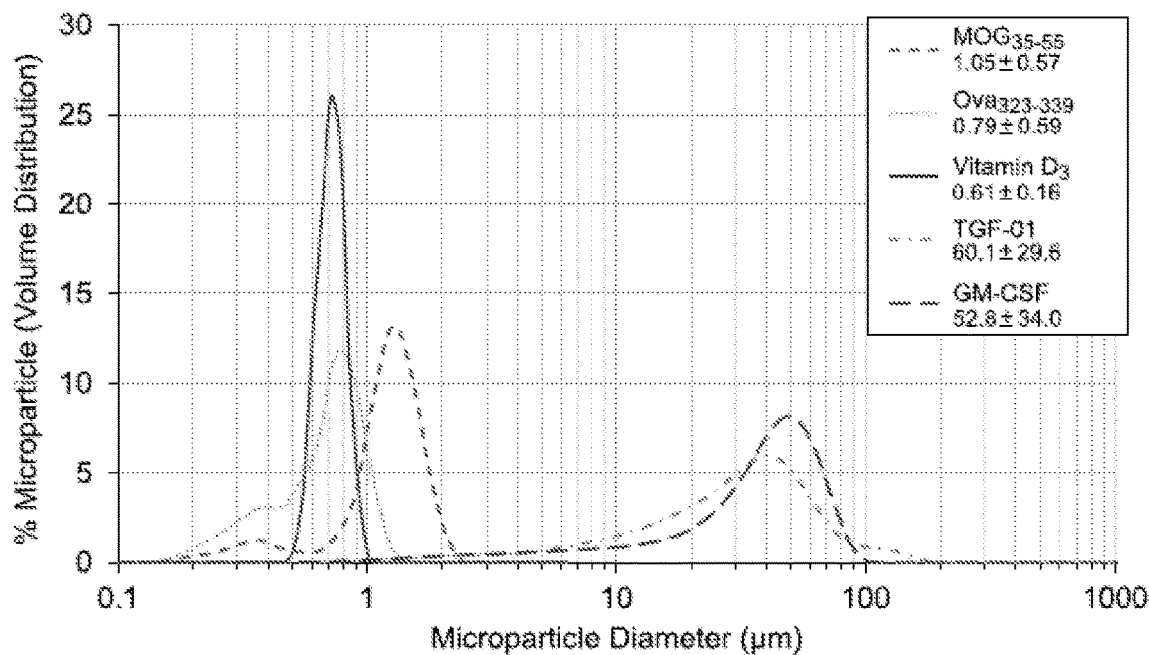
FIGS. 1A-1B show dual microparticle (dMP) fabrication and characterization.

SEQ ID NO: 1 shows the amino acid sequence of human myelin oligodendrocyte glycoprotein (MOG) protein (GenBank: AQY76934.1)

SEQ ID NO: 2 shows the amino acid sequence of human myelin basic protein (MBP) (GenBank: NP_001020252.1)

SEQ ID NO: 3 shows the amino acid sequence of human proteolipid protein (PLP) (GenBank: P60201)

SEQ ID NO: 4 shows the amino acid sequence of human 2',3'-cyclic-nucleotide 3'-phosphodiesterase (CNP) (GenBank: NP_149124.3)

SEQ ID NO: 5 shows the amino acids sequence of human myelin-associated glycoprotein (MAG) (GenBank: NP_002352)

SEQ ID NO: 6 shows the amino acid sequence of human myelin-associated oligodendrocyte basic protein (MOBP) (GenBank: Q13875.2.1)

SEQ ID NO: 7 shows the amino acid sequence of human S100 calcium binding protein B (S100) (GenBank: AAH01766.1)

SEQ ID NO: 8 shows the amino acid sequence of human transaldolase (GenBank: NP_006746.1)

SEQ ID NO: 9 shows the amino acids sequence of human neurofascin (GenBank: O94856.4)

SEQ ID NO: 10 shows the amino acids sequence of human contactin (GenBank: CAA79696.1)

SEQ ID NO: 11 shows the amino acids sequence of human potassium-dependent channel KIR4.1 (GenBank: AAB07046.1)

SEQ ID NO: 12 shows the amino acid sequence portion of MBP pertaining to MBP$_{13-32}$ SEQ ID NO: 13 shows the amino acid sequence portion of MBP pertaining to MBP$_{83-99}$ SEQ ID NO: 14 shows the amino acid sequence portion of MBP pertaining to MBP$_{131-55}$ SEQ ID NO: 15 shows the amino acid sequence portion of MBP pertaining to MBP$_{146-170}$ SEQ ID NO: 16 shows the amino acid sequence portion of PLP pertaining to PLP$_{40-60}$ SEQ ID NO: 17 shows the amino acid sequence portion of PLP pertaining to PLP$_{89-106}$ SEQ ID NO: 18 shows the amino acid sequence portion of PLP pertaining to $PLP_{139-154}$ SEQ ID NO: 19 shows the amino acid sequence portion of PLP pertaining to $PLP_{178-197}$ SEQ ID NO: 20 shows the amino acid sequence portion of PLP pertaining to $PLP_{190-208}$ SEQ ID NO: 21 shows the amino acid sequence portion of MOG pertaining to $MOG_{1-20}$ SEQ ID NO: 22 shows the amino acid sequence portion of MOG pertaining to $MOG_{11-30}$ SEQ ID NO: 23 shows the amino acid sequence portion of MOG pertaining to $MOG_{35-55}$ SEQ ID NO: 24 shows the amino acid sequence portion of CNP pertaining to $CNP_{343-373}$ SEQ ID NO: 25 shows the amino acid sequence portion of CNP pertaining to $CNP_{356-388}$

DETAILED DESCRIPTION OF THE INVENTION

The present disclosure provides antigen-specific, tolerance-inducing microparticles and therapeutic compositions comprising the microparticles. Advantageously, the present disclosure allows for the targeted delivery of therapeutic agents to immune cells. In addition, certain embodiments facilitate sustained release of therapeutic agents. Advantageously, the microparticle delivery system of the present disclosure has antigen-specificity and ex vivo stability.

In one embodiment, provided is a microparticle for targeted delivery of one or more antigens along with immunomodulatory molecules to antigen-presenting cells (e.g., dendritic cells or macrophages).

Delivered immunomodulatory molecules (e.g., transforming growth factor beta 1 (TGF-β1), rapamycin, vitamin D and retinoic acid) can provide immunosuppressant/tolerogenic conditioning of antigen-presenting cells along with delivering an antigen depot for antigen-presenting cells to internalize and present to lymphocytes. Vaccine particles thus modulate antigen-presenting cell function to effect specific tolerance, suitable for the treatment of MS.

Also provided are therapeutic uses of composition embodiments for the prevention and/or treatment of MS.

Multiple sclerosis-like encephalomyelitis can be blocked using disclosed compositions by inducing tolerogenic dendritic cells, reducing infiltrating CD4+ T cells, inflammatory cytokine-producing pathogenic CD4+ T cells, and reducing macrophage and microglia activation in the central nervous system. Furthermore, CD4+ T cells isolated from dMP-treated mice were anergic in response to disease-specific, antigen-loaded splenocytes.

The choice of TGF-β1, GM-CSF, and vitamin D3 for the current dMP system was based on the immunomodulatory and tolerogenic profiles of these compounds, which minimize the risk for global immunosuppression, unlike potent immunosuppressive agents like IL-10 or rapamycin.

Subcutaneously administered $dMP-MOG_{35-55}$ treatment suppressed EAE through reduction of total leukocytes, CD4+ T cells, including those expressing inflammatory cytokine, and activated macrophages/microglia in the CNS. The relative strength of tolerance achieved according to the current invention is superior to the preventative/prophylactic and therapeutic regimen utilized for nanoparticle platforms described previously [18,19], in that the subject invention achieved total suppression of EAE clinical disease and drastic reduction of CD4+ T cell infiltration into CNS.

The quality and timing of tolerance achieved herein with the dMP administered in semi-therapeutic regimen is superior compared to the preventative/prophylactic and therapeutic regimen reported previously for nanoparticle platforms, as it can be used after disease initiation, which has clinical implication for further development into a therapeutic to be administered after disease clinical sign onset.

Controlled-release platforms for immunomodulatory applications are advantageous versus soluble administration. In addition to mitigating the risk for systemic immunosuppression, soluble drugs are rapidly cleared from the body. Thus, pharmacokinetics may prevent soluble administration to effectively restore homeostatic immunity or require more frequent or higher dosing. The impact of biomaterial encapsulation in the subject invention was demonstrated by the requirement for encapsulation of drugs in MPs, as soluble injections of the factors along with unloaded MPs did not prevent T cell infiltration in the CNS. Importantly, the encapsulated drugs could not be detected in the blood, thus preventing global immune suppression following dMP administration.

Induction of antigen-specific tolerance is crucial to developing a safe, translatable therapy for EAE/MS, with the goal to achieve therapeutic efficacy without inducing broad immunosuppression.

By utilizing multiple control groups, it was demonstrated that the $dMP-MOG_{35-55}$ treatment specifically suppressed EAE in an antigen-dependent manner. Comparing the $dMP-MOG_{35-55}$ to a similar formulation without antigen-loaded MPs, it was demonstrated that omission of the antigen resulted in mice developing disease. Similarly, disease was only blocked with $dMP-MOG_{35-55}$ treatment, but not by treatment with an irrelevant antigen, $dMP-Ova_{323-339}$.

The antigen-specificity in the newly developed microparticle-based immunotherapy is especially important because, e.g., the safety profile of an MS antigen-specific tolerogenic regimen is significantly superior to that of other immunotherapies that do not rely on antigen-specificity [20-23]. The observation that CD4+ T cells isolated from EAE mice treated with $dMP-MOG_{35-55}$ were not responsive to stimulation by $MOG_{35-55}$-loaded splenocytes whereas EAE mice treated with $dMP Ova_{323-339}$ proliferated, showed that T cell anergy is effectively induced by the $dMP-MOG_{35-55}$ therapy in an antigen-specific manner.

Together, these results highlight an exciting combinatorial, controlled release, and immunologically-driven approach that operates through a dMP system that delivers local sustained release of multiple immunomodulatory factors, and targets both intra- and extracellular tolerogenic receptors. Using the dMP system of the subject invention, robust and durable antigen-specific autoimmune protection was achieved, which protection was superior to soluble factors or irrelevant antigen formulations. Additionally, the dMP system of the subject invention is versatile because substitutions of antigen and/or factors have the potential to elicit tolerogenic or immunogenic responses in a tailored, disease-specific fashion.

Antigen-Specific Tolerogenic Compositions

Preferably, the microparticle matrix is made of, primarily, substantially biologically inert or biologically compatible materials. The terms "inert," "biologically inert" or "biologically compatible," as used herein, refer to a substance or material that, after the normal healing period when administered into living tissues, does not elicit substantially adverse biochemical, allergic, or unwanted immune responses.

Preferably, the present microparticle matrix is biodegradable. The term "biodegradable," as used herein, refers to the ability of materials to be broken down by normal chemical, biochemical and/or physical processes such as erosion, dissolution, corrosion, degradation, hydrolysis, abrasion, etc, and their combinations.

Biologically compatible materials useful for making the microparticles include, but are not limited to, bio-degradable polymeric materials including, but not limited to, hydrogels, collagen, alginate, poly(glycolic acid) (PGA), poly(L-lactic acid) (PLA), poly(DL-lactic-co-glycolic acid) (PLGA), polyethylene glycol (PEG), polyesters, polyanhydrides, polyorthoesters, polyamides; non-polymeric biodegradable ceramic materials including, but not limited to, calcium phosphate, hydroxyapatite, tricalcium phosphate; and combinations thereof. In preferred embodiments, microparticles are fabricated from poly(lactic-co-glycolic acid) (PLGA), which is FDA approved for delivery of therapeutics. Low molecular weight oligomeric forms of lactide and/or glycolide polymers have several advantages such as good mechanical properties, low immunogenicity and toxicity, excellent biocompatibility, and predictable biodegradation kinetics. Lactide/glycolide polymers are widely accepted for biomedical applications. The mechanical strength, swelling behavior, capacity to undergo hydrolysis, and subsequently the biodegradation rate are directly influenced by the crystallinity of the PLGA polymer and the crystallinity of the PLGA copolymer is dependent on the type and the molar ratio of the individual monomer components (lactide and glycolide) in the copolymer chain. For example, PLGA polymers containing a 50:50 ratio of lactic and glycolic acids are hydrolyzed much faster than those containing higher proportion of either of the two monomers.

The PLGA copolymers of the microparticles of the subject invention are designed in such a ratio that they allow the microparticle degradation to proceed over a period of at least 15 days to about 80 days. In some embodiments, the polymers degrade within 16 days to 79 days; 18 days to 77 days; 20 days to 75 days; 22 days to 73 days; 24 days to 71 days; 26 days to 69 days; 28 days to 67 days; 30 days to 65 days; 32 days to 67 days; 34 days to 65 days; 36 days to 63 days; 38 days to 61 days; 40 days to 59 days; 42 days to 57 days; 44 days to 55 days; 46 days to 53 days; or 48 days to 51 days.

In specific embodiments, the non-phagocytosable microparticles are fabricated such that the PGLA degrades at between 20 days and 60 days. In other specific embodiments, the phagocytosable microparticles are fabricated such that they degrade readily in the endocytic compartment of a phagocyte.

In some embodiments, the subject invention provides an injectable hydrogel composition, wherein the hydrogel comprises or encapsulates therein non-phagocytosable microparticles comprising at least one agent for recruiting the immune cell of interest (e.g., GM-CSF); and at least one immunosuppressive agent (e.g., TGF-β1) and phagocytosable microparticles comprising at least one antigen (which can be an auto-antigen and/or allergen) and at least one immunomodulatory agent (e.g., vitamin D3). In specific embodiments, the injectable, biodegradable hydrogel is fabricated via in situ gelling, and facilitates sustained-release of its ingredients for a prolong period of time (e.g., several days).

In specific embodiments, the microparticles are fabricated of PGLA using single or double emulsions. In certain embodiments, the different factors including at least one antigen, at least one immunoregulatory agent, at least one immunosuppressive agent and at least one chemoattractant are encapsulated into PGLA microparticles separately to control encapsulation efficiency. In other embodiments, the several components are encapsulated together or in different mixtures into the microparticles. For example, in some microparticles at least one antigen and at least one immunomodulatory agent are encapsulated in the same microparticles. In other microparticles, at least one immunosuppressive agent and at least one chemoattractant are encapsulated in the same microparticles.

In some embodiments, the at least one antigen and the at least one immunomodulatory agent encapsulated into the same microparticles are present within the microparticles at a specified ratio to ensure optimal antigen stimulation and immune modulation of the antigen presenting cells. In other embodiments, the at least one antigen and the at least one immunomodulatory agent are encapsulated into separate phagocytosable microparticles and are administered at a ratio that ensures optimal antigen stimulation and immune modulation of antigen presenting cells.

In specific embodiments, at least one antigen is encapsulated with at least one immunomodulatory agent into the same microparticle or at least one antigen is encapsulated in one microparticle and at least one immunomodulatory agent is encapsulated in a separate microparticle and both microparticles are administered such that the at least one antigen and the at least one immunomodulatory agent are administered at a ratio of a low of 1:20 to a high of 1:1; and any ratio therebetween, such as about 1:19; about 1:18; about 1:17; about 1:16; about 1:15; about 1:14; about 1:13; about 1:12; about 1:11; about 1:10; about 1:9; about 1:8; about 1:7; about 1:6; about 1:5; about 1:4; about 1:3; and about 1:2.

In some embodiments, at least one immune suppressive agent and at least one chemoattractant are encapsulated into the same non-phagocytosable microparticles at a specified ratio to facilitate immunosuppression and chemoattraction of immune cells. In other embodiments, at least one immune suppressive agent and at least one chemoattractant are encapsulated into separate non-phagocytosable microparticles and are administered at a specified ratio to ensure optimal immunosuppression and chemoattraction of immune cells.

In specific embodiments, at least one immune suppressive agent is encapsulated with at least one chemoattractant into the same microparticles or at least one immune suppressive agent is encapsulated in one microparticle and at least one chemoattractant is encapsulated in a separate microparticle and both microparticles are administered such that the at least one immunosuppressive agent and the at least one chemoattractant are administered at a ratio of a low of 1:5 to a high of 5:1; and any ratio therebetween, such as about 1:4; about 1:3; about 1:2; about 1:1; about 2:1; about 3:1; and about 4:1.

For example, in a specific embodiment, phagocytosable microparticles comprising a myelin-derived antigen and phagocytosable microparticles comprising the immunomodulatory agent vitamin D3 are injected together subcutaneously into a subject such that about 30 to 50 mcg of the myelin-derived antigen per mg PGLA are administered together with about 60 to 70 ng of the immunomodulatory vitamin D3 per mg PGLA.

Further, together with the above phagocytosable microparticles are injected non-phagocytosable microparticles comprising the immunosuppressive agent TGF-β1 and non-phagocytosable microparticles comprising the chemoattractant agent GM-CSF subcutaneously into the subject together with the phagocytosable microparticles described above such that about 20 to 25 ng of the immunosuppressive agent TGF-β1 per mg PGLA of the non-phagocytosable microparticles are administered together with about 40 to 55 ng of the chemoattractant GM-CSF per mg PGLA of the other non-phagocytosable microparticles.

Advantageously, the co-administration of the two types of phagocytosable microparticles and the two types of non-phagocytosable microparticles together subcutaneously into a subject in the described ratios of myelin-derived antigen, immunomodulatory agent, immunosuppressive agent and chemoattractant allows the optimized stimulation and priming of immune cells in the subject to induce an efficient amount of antigen-specific tolerogenic dendritic cells to treat, for example, MS in the subject.

In a preferred embodiment, the antigen is a myelin-derived antigen. The at least one myelin-derived antigen of the subject invention can be derived from a myelin-specific protein including, but not limited to, a myelin oligodendrocyte glycoprotein (MOG), a proteolipid protein (PLP), a myelin basic protein (MBP), a myelin-associated oligodendrocyte basic protein (MOBP), myelin-associated glycoprotein (MAG), a glatiramer acetate (a random polymer of L-alanine, L-glutamic acid, L-lysine, and L-tyrpsine), a 2',3'-cyclic-nucleotide 3'-phosphodiesterase (CNP), a $S100\beta$ protein, a transaldolase H, a neurofascin, a contactin, a potassium-dependent channel KIR4.1 or any protein linked to the pathogenesis of multiple sclerosis in humans [25, 25]. In preferred embodiments, the myelin-derived antigen is an antigen involved in the pathogenesis of multiple sclerosis. In further preferred embodiments, the myelin-derived antigen is $MOG_{35-55}$.

Other examples of antigens include, but are not limited to, $MOG_{1-20}$, $MOG_{11-30}$, $MOG_{35-55}$, $MBP_{13-32}$, $MBP_{83-99}$, $MBP_{111-129}$, $MBP_{146-170}$, $PLP_{40-60}$, peptide $PLP_{89-106}$, $PLP_{139-154}$, $PLP_{178-197}$, $PLP_{190-208}$, $CNP_{343-373}$, and $CNP_{356-388}$.

For example, a composition of the subject invention can comprise phagocytosable microparticles comprising 400-700 mcg/kg MOG and/or 8-12 mcg/kg Vitamin D3 and non-phagocytosable microparticles comprising 2-5 mcg/kg TGF-β1 and/or 5-9 mcg/kg GM-CSF.

The at least one antigen to be used in the composition of the subject invention can be a peptide of any length comprising a low of 5 amino acids (aa) to a high of 100 aa of a myelin-related protein and any length in between, such as about 5 aa to about 95 aa; about 5 aa to about 90 aa; about 5 aa to about 85 aa; about 5 aa to about 80 aa; about 5 aa to about 75 aa; about 5 aa to about 70 aa; about 5 aa to about 65 aa; about 5 aa to about 60 aa; about 5 aa to about 55 aa; about 5 aa to about 50; about 5 aa to about 45 aa; about 5 aa to about 40; about 5 aa to about 35 aa; about 5 aa to about 30 aa; about 5 aa to about 25 aa; about 5 aa to about 20 aa; about 5 aa to about 15 aa; about 5 aa to about 14 aa; about 5 aa to about 13 aa; about 5 aa to about 12 aa; about 5 aa to about 11 aa; about 5 aa to about 10 aa; about 5 aa to about 9 aa; about 5 aa to about 8; about 5 aa to about 7 aa; and about 5 aa to about 6 aa.

In preferred embodiments, the antigen is a peptide of about 5 aa to about 12 aa. In more preferred embodiment, the antigen is a peptide of about 5 aa to about 10 aa. In most preferred embodiments, the antigen is a peptide of about 5 aa to about 9 aa.

In some embodiments, the immunomodulatory agent used in the composition of the subject invention is selected from vitamin D3, vitamin D3 analogs, glucocorticoids, estrogens, rapamycin, and retinoic acid. In preferred embodiments, the immunomodulatory agent is vitamin D3 or a vitamin D3 analog, a glucocorticoid, an estrogen, or retinoic acid. In more preferred embodiments, the immunomodulatory agent is vitamin D3 or a vitamin D3 analog.

Anti-inflammatory or immunosuppressive agents useful according to the present invention include TGF-β1, IL-10, INF-γ and INF-λ and nonsteroidal anti-inflammatory drugs (NSAIDs) such as aspirin and ibuprofen; naproxen; and triterpinoids such as betulinic acid, bardoxolone methyl, and triterpenoid saponins.

In some embodiments, the immunosuppressive agent used in the composition of the subject invention is selected from TGF-β1, IL-10, INF-γ, INF-λ, and nonsteroidal anti-inflammatory drugs. In specific embodiments, the immunosuppressive agent is TGF-β1, IL-10 or IFN-γ. In more specific embodiments, the immunosuppressive agent is TGF-β1.

A variety of agents that recruit or attract immune cells are also known. For example, chemoattractants that recruit dendritic cells include granulocyte macrophage colony stimulating factor (GM-CSF), granulocyte-colony stimulating factor (G-CSF), macrophage colony-stimulating factor (M-CSF), C—C motif chemokine ligand 19 (CCL19), C—C motif chemokine ligand 20 (CCL 20), C—C motif chemokine ligand 21 (CCL21) and vascular endothelial growth factor C (VEGF-C). Preferably, GM-CSF, which selectively attracts immature dendritic cells, is used in the present invention.

In some embodiments, the composition of the subject invention comprises a remyelinating agent selected from clemastine, clobetasol, digoxin, miconazole, phenytoin, and quetiapine. Said remyelinating agent can be administered in soluble form by intravenous injection or can be incorporated into the non-phagocytosable microparticles.

Advantageously, the compositions disclosed herein comprising a dual microparticle system in a liquid formulation provide spatial and temporal control of the release of the cargo, e.g., antigen, immunomodulatory, immunosuppressive, and chemoattractive agents after administration to a subject in such a manner that tolerogenic dendritic cells are generated in the subject. Importantly, the composition ensures that the respective components are provided in the amounts and/or ratios such that antigen presenting cells are recruited within the subject from a large area surrounding the administration site and stimulated with antigen and immunomodulatory agents to ensure the induction of a tolerogenic phenotype in antigen presenting cells. Antigen presenting cells primed by the phagocytosed microparticles are then attracted to the site close to the administration site by chemoattractants released by the non-phagocytosable microparticles and the attracted cells are exposed to sufficient amounts of immune suppressive agents to ensure the generation of tolergenic dendritic cells. Such induced tolerogenic dendritic cells, in turn, promote the induction of regulatory T cells and suppress auto-reactive T-cells.

Advantageously, certain embodiments provide a means to improve the generation of antigen-specific tolerogenic dendritic cells. In specific embodiments, an immunological pathomechanism in the brain, e.g., in MS, can be effectively treated using the compositions of the subject invention.

The phagocytosable microparticles disclosed herein are designed to deliver their cargo into antigen presenting cells. Therefore, the phagocytosable microparticles have a size that avoids pinocytosis, i.e., uptake into fluid vesicles of non-antigen presenting cells because such pinocytotic uptake reduces the amount of microparticles administered that can be taken up by antigen presenting cells. Phagocytosis allows for endosomal release of encapsulated antigens and therapeutic agents from a polymeric matrix such as PLGA to intracellular targets. In specific embodiments, the microparticles disclosed herein generate both MHC-II-directed and MHC-I-directed immune responses through cross-presentation.

The phagocytosable microparticles are designed to be of a size that facilitates farther distribution of these particles from the site of administration in a subject allowing for a larger area to receive phagocytosable microparticles delivering at least one antigen and at least one immunomodulatory agent.

The non-phagocytosable microparticles are designed to avoid any cellular uptake and allow extracellular release of their cargo over a desired period of time. Furthermore, the non-phagocytosable microparticles are designed in such a size that the particles are prevented from moving over a far distance from the administration site in the subject to allow a localized release and, thus, high concentration of the at least one immunosuppressive agent and the at least one chemoattractant encapsulated in the non-phagocytosable microparticles.

In specific embodiments, the microparticles phagocytosable by dendritic cells have a diameter in the range of 0.1 m to 10.0 m, or any range therebetween, such as 0.2 m to 8.0 m; 0.3 m to 5.0 m; 0.4 m to 3.0 m; 0.5 m to 2.0 m; 0.6 m to 1.0 m. In certain embodiments, the microparticle has a diameter of about 0.2 m to 3.0 m. In preferred embodiments, the phagocytosable microparticles are 0.2 m to 5.0 m or 0.3 m to 2.0 m. In more specific embodiments, the phagocytosable microparticles are 0.6 m to 1.0 m in diameter.

In certain embodiments, the microparticles are non-phagocytosable by dendritic cells and have a diameter in the range of about 15 μm to 200 μm; or any range therebetween, such as 15 μm to 180 μm; 15 μm to 150 μm; 15 μm to 120 μm; 15 μm to 100 μm; 15 μm to 80 μm; 15 μm to 60 μm; 15 μm to 50 μm; 15 μm to 40 μm; 15 μm to 30 μm; 15 μm to 20 μm; 20 μm to 200 μm; 20 μm to 180 μm; 20 μm to 150 μm; 20 μm to 120 μm; 20 μm to 100 μm; 20 μm to 80 μm; 20 μm to 60 μm; 20 μm to 50 μm; 20 μm to 40 μm; 20 μm to 30 μm; 30 μm to 200 μm; 30 μm to 180 μm; 30 μm to 150 μm; 30 μm to 120 μm; 30 μm to 100 μm; 30 μm to 80 μm; 30 μm to 60 μm; 30 μm to 40 μm; 40 μm to 180 μm; 40 μm to 150 μm; 40 μm to 120 μm; 40 μm to 100 μm; 40 μm to 80 μm; 40 μm to 70 μm; 40 μm to 60 μm; 40 μm to 50 μm; 50 μm to 200 μm; 50 μm to 180 μm; 50 μm to 150 μm; 50 μm to 120 μm; 50 μm to 100 μm; 50 μm to 80 μm; 50 μm to 70 μm; 50 μm to 60 μm; 60 μm to 180 μm; 60 μm to 150 μm; 60 μm to 120 μm; 60 μm to 100 μm; 60 μm to 80 μm; 60 μm to 70 μm; 70 μm to 180 μm; 70 μm to 150 μm; 70 μm to 120 μm; 70 μm to 100 μm; 70 μm to 80 μm; 80 μm to 200 μm; 80 μm to 180 μm; 80 μm to 150 μm; 80 μm to 120 μm; 80 μm to 100 μm; 80 μm to 90 μm; 90 μm to 200 μm; 90 μm to 180 μm; 90 μm to 150 μm; 90 μm to 120 μm; 90 μm to 100 μm; 100 μm to 200 μm; 100 μm to 180 μm; 100 μm to 150 μm; 100 μm to 120 μm; 100 μm to 110 μm; 120 μm to 200 μm; 120 μm to 180 μm; 120 μm to 150 μm; 120 μm to 140 μm; 120 μm to 130 μm.

The size of the microparticles can be optimized by those skilled in the art having the benefit of the subject disclosure to achieve optimal delivery effects, depending on various parameters, such as for example, the cell type, the amount of therapeutics encapsulated, the site of delivery, and the host species.

Immune cells that can be targeted according to the present invention include, but are not limited to, dendritic cells, macrophages, lymphocytes, monocytes, neutrophils, mast cells, B cells, T cells, and T helper cells. In certain embodiments, professional antigen-presenting cells, such as dendritic cells, macrophages, T cells, and B cells, are targeted. In certain embodiments, dendritic cell and/or Treg cells are targeted.

In some embodiments, the outer surface of the microparticles comprise one or more surface ligands, such as antibodies, that target specific immune cells. In certain embodiments, the surface ligands are chemically fixed, or covalently linked, to the microparticles. In specific embodiments, the microparticles target dendritic cells. In specific embodiments, the microparticles specifically and selectively target immature dendritic cells, when compared to mature dendritic cells. Preferably, the surface ligands or antibodies also induce apoptotic and/or tolerance-inducing pathways in immune cells.

Exemplified surface ligands for dendritic cells include, but are not limited to, antibodies, aptamers and binding partners that bind specifically to cell surface ligands/receptors of dendritic cells, such as anti-CD 11 antibodies and anti-Dec205 antibodies; phosphatidyl serine (PS){PS receptor}; 4N1K{CD36/CD47}; PD2{CD11c}; P2{CD11b}; RGD{$\alpha_v\beta_3$}; and CS1{$\alpha_4\beta_7$}. In a specific embodiment, the surface antibody is an anti-DEC-205 antibody, which recognizes dendritic cells. In a further specific embodiment, the microparticle matrix is surface modified with PD2 for targeting dendritic cells. Preferably, the therapeutic compositions do not contain any maturation stimuli such as prostaglandin E2.

Adjuvants useful in accordance with the subject invention include, but are not limited to, CpG, poly I:C, and mPLA.

In certain specific embodiments, further therapeutic agents useful according to the teachings herein include, but are not limited to, T cell inhibitory agents such as cytotoxic T-lymphocyte antigen 4 (CTLA-4) and indoleamine 2,3 dioxygenase (IDO); Treg selective growth factors, such as IL-2, rapamycin, or a phosphodiesterase 3B (PDE3b) inhibitor, such as cilostamide; and agents that inhibit maturation of dendritic cells, such as vascular endothelial growth factor (VEGF) and transcription factor E2F1.

Induction of Antigen-Specific Immune Tolerance

In particular aspects, provided are therapeutic methods for inducing antigen-specific immune tolerance for the treatment of MS. Preferably, the methods comprise administering, to a subject to which the induction of antigen-specific immune tolerance is needed, an effective amount of the microparticles and therapeutic compositions of the subject invention. In specific embodiments, the therapeutic compositions specifically target dendritic cells, induce dendritic cells with a tolerogenic phenotype, promote induction of Treg cells, and/or suppress T cell proliferation.

The term "tolerance," as used herein, refers to a failure to respond, or a reduced response, to an antigen, including auto-antigens.

The term "tolerogenic" or "tolerance-inducing," as used herein, refers to a phenotype that induces tolerance to an antigen directly or indirectly, or is capable of silencing or down-regulating an adaptive immunological response to an antigen. Tolerogenic dendritic cells have a low ability to activate effector T cells, but have a high ability to induce and activate regulatory T cells. In some embodiments, tolerogenic dendritic cells typically have reduced MHCII, CD80, CD86 levels and express tolerogenic markers such as CD103 and indoleamine 2,3 dioxygenase.

Preferably, the microparticles of the subject invention target immature dendritic cells, and do not target mature dendritic cells. Immature dendritic cells have a very dendritic morphology and have a low T cell activation potential. Immature dendritic cells undergo an irreversible maturation process upon activation of maturation stimuli. Mature dendritic cells have an enhanced ability to process antigens and activate T cells.

As demonstrated in the examples, the microparticles disclosed herein can have improved dendritic cell-targeting specificity and increased uptake by dendritic cells; result in functional antigen processing and presentation in dendritic cells; facilitate the maintenance of immature dendritic cell phenotype, and prevent or delay the maturation and expression of tolerogenic dendritic cell markers (e.g., indoleamine 2,3 dioxygenase) following particle uptake; facilitate the suppression of allogeneic mixed lymphocyte reactions; and induce FoxP3$^+$ Treg cells.

In some embodiments, the administration of the microparticle composition results in downregulation of MHC-II, CD 86, and CD 80. In addition, microparticles surface modified with ligands 4N1K, RGD and/or CS1 show reduced T-cell proliferation in mixed-lymphocyte reaction tests compared to immature dendritic cell controls. In addition, the microparticles suppress auto-reactive T-cells through the induction of regulatory T-cells.

Advantageously, the present microparticle-encapsulated vaccine can be easily administered with simultaneous delivery of both prime and boost doses using time-release materials (e.g., poly lactide-co-glycolide).

Treatment of Multiple Sclerosis (MS)

According to certain embodiments, methods are provided for the prevention and/or treatment of MS. Preferably, the methods comprise administering, to a subject, who has been diagnosed to be in need of such treatment, an effective amount of microparticles or a composition of the present invention. The disease and disease state are typically diagnosed based on MS symptoms.

The term "treatment" or any grammatical variation thereof (e.g., treat, treating, and treatment etc.), as used herein, includes but is not limited to, ameliorating or alleviating a symptom of a disease or condition, reducing, suppressing, inhibiting, lessening, or affecting the progression, severity, and/or scope of a condition.

The term "prevention" or any grammatical variation thereof (e.g., prevent, preventing, and prevention etc.), as used herein, includes but is not limited to, delaying the onset of symptoms, preventing relapse to a disease, decreasing the number or frequency of relapse episodes, increasing latency between symptomatic episodes, or a combination thereof. Prevention, as used herein, does not require complete inhibition or elimination of the condition or its symptoms. Symptoms of multiple sclerosis include the following.

vision problems (included blurred vision, double vision or loss of vision);
tingling and numbness (common sites of numbness include the face, arms, legs and fingers);
pains and spasms (commonly observed in back and legs);
weakness or fatigue (typically first observed in legs);
balance problems or dizziness;
bladder issues (including frequent urination, strong urges to urinate or incontinence);
sexual dysfunction; or
cognitive problems (including memory problems, shortened attention span, and language problems).

The term "effective amount," as used herein, refers to an amount that is capable of treating or preventing a disease or condition or otherwise capable of producing an intended therapeutic effect. In one embodiment, an effective amount is a tolerogenic amount. For instance, an effective amount of an antigen is capable of inducing antigen-specific immune tolerance, but is incapable of generating an immunogenic reaction.

In some embodiments, the therapeutically effective amount can be an amount of a composition of the subject invention that is effective in inducing a regulatory immune response including, but is not limited to, reducing levels of pro-inflammatory cytokines including, but not limited to, IL-1β, TNF-α, IL-6, INF-γ, Cxcl2, GM-CSF and IL-17A; decreasing the frequency of IL-1β', CD86$^+$ and MHC II expressing dendritic cells; increasing the frequency of regulatory dendritic cells such as IL-10$^+$ dendritic cells; increasing the frequency of dendritic cells expressing programmed death-ligand1 (PD-L1); decreasing the frequency of CD4$^+$ and/or CD8$^+$ T cells expressing IFNγ; decreasing the frequency of pathogenic CD4$^+$ T cells expressing the transcription factors Rorγt and T-bet; increasing the frequency of regulatory T cells (Tregs); increasing FoxP3$^+$ Tregs; and decreasing the frequency of activated macrophages and microglia in the CNS.

The term "administering" as used herein, describes the delivery of a composition of the subject invention comprising a dual microparticle system to tissues, e.g., skin, muscle, an organ, etc. or other localized sites, e.g., lymph nodes, Peyer's patches etc. Administration includes, but is not limited to, subcutaneous, subdermally, intradermal, intramuscular, intravenous, intraarticular, intracranial, intracerebral, intraspinal, intravaginal, intrauterine, transdermal, transmucosal, rectal, oral or by inhalation.

The term "subject," as used herein, describes an organism, including mammals such as primates, to which treatment with the compositions according to the present invention can be provided. Mammalian species that can benefit from the disclosed methods of treatment include, but are not limited to, primates such as apes, chimpanzees, orangutans, humans, monkeys; and non-primates such as dogs, cats, horses, cattle, pigs, sheep, goats, chickens, mice, rats, guinea pigs, and hamsters.

In certain embodiments, subjects treated in accordance with the present invention have been diagnosed with MS. In other embodiments, subjects treated are diagnosed as susceptible to, or predisposed to, developing MS, where predisposition or susceptibility to MS can be determined by a combination of factors, such as presence of a personal and family history of autoimmune disease, presence of genetic markers associated with autoimmunity, and/or living and/or working in conditions with a high chance of exposure to toxin or infection. A skilled physician can readily determine whether a subject is predisposed to, susceptible to, or has, MS.

In some embodiments, the prevention and treatment methods comprise, prior to administration of the microparticles and compositions of the invention, a step of diagnosing whether the subject has, or is predisposed to, MS.

Further, the present invention can also be used to inhibit macrophage or T cell associated aspects of an immune response and inhibit macrophage or T cell activities including, but not limited to, macrophage antigen-presenting activity, macrophage-associated cytokine production, T cell cytokine production, T cell adhesion, and T cell proliferative activities. Thus, the present invention is also useful to suppress or inhibit humoral and/or cellular immune responses.

Advantageously, embodiments can be used for antigen-specific tolerizing treatments for MS. Compared to the current treatments, which induce systemic suppression, the treatment of the subject invention is antigen-specific, delivers optimized amounts and/or ratios of antigen, immmunomodulatory, immunosuppressive, and chemoattractive agents and leads to efficient induction of tolerogenic dendritic cells to treat MS, which induction of tolerogenic dendritic cells is more efficient and superior to previously used methods in the art.

Therefore, the dMP system combines the attractive notion of antigen-specificity and combination therapy with a dual-sized controlled release scheme to provide immune modulation without systemic delivery. The dMP system vaccine of the subject invention can be easily administered via subcutaneous injection and provides for sustained delivery using biodegradable, controlled-release materials. Additionally, biomaterial encapsulation provides vaccine stability and extended shelf life, thereby simplifying manufacturing, storage and shipping.

Animal models useful to test therapeutic approaches are available in the art. For example, treatment approaches for animal models of encephalomyelitis-associated diseases are defined as follows: (a) preventative/prophylactic treatment is when factors are administered before disease induction, (b) therapeutic treatment is applied when agents are delivered after appearance of clinical disease signs, and (c) semi-therapeutic regimen is used when agents are administered after disease induction but before clinical disease signs [51, 53].

Formulations and Administration

According to certain embodiments, provided are therapeutic or pharmaceutical compositions. In some embodiments, the compositions comprise a therapeutically effective amount of microparticles of the present invention and, optionally, a pharmaceutically acceptable carrier.

Suitable non-toxic pharmaceutically acceptable carriers for use with the agent will be apparent to those skilled in the art of pharmaceutical formulation. See, for example, Remington's Pharmaceutical Sciences, seventeenth edition, ed. Alfonso R. Gennaro, Mack Publishing Company, Easton, Pa. (1985).

The microparticles and therapeutic compositions of the subject invention may be delivered to tissues, e.g., skin, muscle, organ, etc or other localized sites, e.g., lymph nodes, Peyer's patches, etc.

In some embodiments, the microparticles of the subject invention are formulated into a vaccine composition for administration to subjects having certain risks of developing inflammatory and/or autoimmune-related disorders. In addition, the compositions disclosed herein can be administered to a subject with existing symptoms of inflammatory and autoimmune-related disorders, and provides for customized vaccine schedules and compositions to prevent or minimize worsening of the diseases.

The therapeutic dosage range can be determined by one skilled in the art having the benefit of the current disclosure. Naturally, such therapeutic dosage ranges will vary with the size, species and physical condition of the patient, the severity of the patient's medical condition, the particular dosage form employed, the route of administration and the like.

The composition can be administered in a single dose or in more than one dose over a period of time to confer the desired effect.

In preferred embodiments, the microparticles can be formulated for parenteral administration. The preparation of an aqueous composition that contains one or more agents, will be known to those of skill in the art in light of the present disclosure. Typically, such compositions can be prepared as injectables, either as liquid solutions or suspensions; solid forms suitable for using to prepare solutions or suspensions upon the addition of a liquid prior to injection can also be prepared; and the preparations can also be emulsified.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi.

Compositions comprising the microparticles disclosed herein can be formulated into a composition in a neutral or salt form. Pharmaceutically acceptable salts include the acid addition salts and those formed with inorganic acids such as, for example, hydrochloric or phosphoric acids, or such organic acids as acetic, oxalic, tartaric, mandelic, and the like. Salts can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), dimethylsulfoxide (DMSO), suitable mixtures thereof, and vegetable oils. The proper fluidity can be maintained, for example, by the use of a coating, such as lecithin, by the maintenance of the required particle size in the case of dispersion and by the use of surfactants. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum drying and freeze-drying techniques, which yield a powder of the active ingredient, plus any additional desired ingredient from a previously sterile-filtered solution thereof.

The compositions disclosed herein can be administered to the subject being treated by standard routes, including the topical, transdermal, intraarticular, parenteral (e.g., intravenous, intraperitoneal, intradermal, subcutaneous or intramuscular), intracranial, intracerebral, intraspinal, intravaginal, or intrauterine. Depending on the condition being treated, one route may be preferred over others, which can be determined by those skilled in the art. In preferred embodiments, the compositions of the present invention are formulated for parental administration. In another embodiment, the peptides and compositions of the present invention are formulated as a sustained-release formulation.

A further embodiment provides for the administration of microparticles in combination with other pharmacological therapies. Combination therapies with other medicaments targeting similar or distinct disease mechanisms have advantages of greater efficacy and safety relative to respective monotherapies with either specific medicament.

When administering more than one, the administration of the agents can occur simultaneously or sequentially in time. The agents can be administered before and after one another, or at the same time. The methods also include co-administration with other drugs that are used to treat retinopathy or other diseases described herein.

Desirable key features of particle vaccines for immunotherapy include control over phagocytosability, delivery of antigen to DCs, and local release of desired agents.

Therefore, the multi-factor dMP treatment disclosed herein offers the advantage of a subcutaneous localized administration, as opposed to systemic administration, with low-dose, localized, controlled release of specific factors designed to be retained at the injection site. This dMP approach does not result in an increase of the tolerogenic factors systemically, efficiently treats EAE, and is antigen-specific.

Following are examples which illustrate procedures for practicing the invention. These examples should not be construed as limiting. All percentages are by weight and all solvent mixture proportions are by volume unless otherwise noted.

Materials and Methods

Isolation of Mononuclear Cells from CNS

Mononuclear cells were isolated from CNS as described previously [26, 27]. Briefly, cold PBS was used to perfuse CNS. Brain and spinal cord were homogenized with gentle MACS dissociator (Miltenyi Biotec), pressed through a 70 µm mesh, then suspended in 30% isotonic Percoll (GE Healthcare). The 30% isotonic Percoll solution containing homogenized CNS was then layered on top of 70% isotonic Percoll and centrifuged for 30 min at 500 g. The 70%-30% interphase containing CNS mononuclear cells was collected then washed with 1×HBSS. Isolated mononuclear cells from CNS were subjected to fluorophore-conjugated antibody staining and flow cytometry analysis.

In Vitro Antigen Re-Stimulation Assay

Total cells were isolated from draining lymph nodes of EAE mice treated with dMP $MOG_{35-55}$ or dMP $Ova_{323-339}$ then loaded with CFSE as described previously [28]. CFSE-loaded cells were then co-cultured with $MOG_{35-55}$-loaded splenocytes isolated from congenic $Rag1^{-/-}$ mice for 72 h. After 72 h, cells were washed and surface stained with CD4, CD8, CD3, and analyzed by flow cytometry.

Antibodies

Cells were stained with the following antibodies: CD11b (APC, APC-eFluor 780, AF647, clone: M1/70), CD11c (Brilliant violet 650, PE-cyanine7, clone: N418, HL3), PD-L1 (CD274, B7-H1, Brilliant Violet 711, clone: 10F.9G2), B7-H2 (ICOS-L, CD275, eFluor 660, clone: HK5.3), CD272 (BTLA, PE, clone: 6A6), Fixable viability dye (eFluor 520, eFluor 780, FITC), IL-1β(PerCP-Cyanine5.5, clone: JES5-16E3), IL-27 p28 (PE-cyanine7, clone: MM27-7B1), Galectin-9 (Brilliant violet 421, clone: RG9-35), CD4 (Brilliant violet 711, clone: GK1.5), PD-1 (CD279, Brilliant violet 605, clone: 29F.1A12), Rorγt (APC, clone: AFKJS-9), T-bet (PE-cyanine7, clone: 4B10), IL-17a (eFluor 450, clone: eBio17B7), GM-CSF (PE, clone: MP1-22E9), IFNγ (FITC, clone: XMG1.2), Ly6C (eFluor 450, clone: HK1.4), Ly6G (GR-1, FITC, AF700, clone: 1A8-Ly6g), F4/80 (PE, clone: BM8), CD80 (Brilliant violet 605, clone: 16-10A1), CD86 (PE-cyanine7, Brilliant violet 605, clone: GL-1), MHC class II (I-A/I-E, PerCP-eFluor 710, clone: M5/114.15.2), CD25 (Brilliant violet 605, clone: PC61), HVEM (CD270, PE, clone: LH1), CD39 (PE-cyanine7, clone: 24DMS1), CD73 (eFluor 450, clone: TY/11.8), Foxp3 (eFluor 450, FITC, clone: FJK-16s), CTLA4 (CD152, APC, clone: UC10-4B9), GITR (CD357, PE-cyanine7, clone: DTA-1), CD103 (Integrin alpha E, APC, clone: 2E7), Lag-3 (CD223, PE, clone: eBioC9B7W), Granzyme B (FITC, clone: GB11), CD8a (PE, clone: 53e6.7), TCRb (APC, clone: H57-597), CD3e (APC-cy7, clone: 145-2C11), CD45 (PE, APC-cyanine7, clone: 30-F11), and CD16/32 (FCγ III/II receptor, clone 2.4G2).

Intracellular/Intranuclear Staining

PMA/Ionomycin stimulation with Brefeldin A and intracellular/intranuclear staining were performed as described previously [29, 30]. Briefly, for detection of cytokines and transcription factors by intracellular/intranuclear flow cytometry, cells were cultured at 37° C. and 5% CO2 for 4 h in IMDM media (Gibco, Life Technologies) containing PMA (20 ng/mL) (Sigma) and Ionomycin (1 mg/mL) (Sigma). Brefeldin A (10 mg/mL) was added 1 h following PMA/Ionomycin addition. Cells were washed and stained with Fixable Viability Dye (Affymetrix, Life Technologies) and surface markers following stimulation. Surface marker stained cells were fixed and permeabilized with Foxp3 Fix/Perm Kit (Affymetrix, Life Technologies) followed by cytokine and transcription factor staining.

Flow Cytometry

Flow cytometry was performed on a BD LSR II with BD FACS DIVA software for data acquisition (BD Biosciences). All flow cytometry data were analyzed with FlowJo software (Tree Star).

Statistical Analysis

GraphPad Prism software version 5 was used for statistical analysis. Statistical significance was assessed by two-tailed un-paired Student's t tests for all analyses except FIGS. 2H, 2I, 2K, 2L, 2M, 3B, and 8B where a one-way analysis of variance (ANOVA) with Tukey's post-hoc analysis was used. Statistical significance between groups was defined at $p<0.05$.

EXAMPLES

Example 1: Dual-Sized MP System for the Treatment of Multiple Sclerosis

Microparticles (MPs) were fabricated from poly (lactic-co-glycolic acid) (PLGA) for delivering immunotherapeutics.

Specifically two sizes of MPs were used in the dual MP (dMP) system (FIG. 1): (1) phagocytosable ~1 µm MP for delivery of antigen (Ag) and drugs to intracellular targets within phagocytes, and (2) non-phagocytosable ~50 µm MP for controlled release of factors targeted to cell surface receptors in a localized microenvironment. Two phagocytosable MPs were used: (a) MPs encapsulating MS-specific antigens, myelin oligodendrocyte glycoprotein peptide ($MOG_{35-55}$), or as a control, the irrelevant $OVA_{323-339}$ peptide, and (b) MPs loaded with vitamin D3 (VitD3). Further, two non-phagocytosable MPs were used: (c) MPs encapsulating TGF-β1, and (d) MPs encapsulating GM-CSF. These four MPs were mixed in equal mass and administered subcutaneously.

Transforming growth factor-beta 1 (TGF-β1) is loaded into the 50 µm MP to provide extracellular release to target its receptor on the DC surface. Granulocyte-macrophage colony-stimulating factor (GM-CSF) is also separately loaded into a 50 µm MP for extracellular release, to locally attract and sustain DCs. Because the MPs of the subject invention advantageously provide GM-CSF locally for the select stimulation of APC in the context of immunosuppressive agents, the MPs of the subject invention allow the induction of tolerogenic DC in a localized environment providing exposure to antigen and immunosuppressive cytokines to treat MS while avoiding generalized effects of the cytokine.

In sum, the four factors are loaded into separate MPs, with those targeting intracellular pathways in phagocytosable MPs and those targeting surface receptors in non-phagocytosable MPs, which targeting is cheived through the dual size MPs.

Example 2: Microparticle Fabrication

Microparticles (MPs) were fabricated by standard oil-in-water single emulsion or water-in-oil-in-water double emulsion methods, as described previously [31]. All drugs were encapsulated in distinct MPs, as no two factors were loaded simultaneously. A 50:50 copolymer of poly (lactic-co-glycolic acid) (PLGA; MW~44,000 g/mol; Corbion Purac, Gorinchem, Netherlands) in methylene chloride (Themo Fisher Scientific, NJ, USA) was used to generate MPs. Ultrapure water (Barnstead GenPure, Thermo Fisher Scientific) was used as the aqueous phase, with dissolved surfactant, poly-vinyl alcohol (PVA; MW~15,000 g/mol; Themo Fisher Scientific), to stabilize the emulsions.

Phagocytosable MPs were fabricated by dissolving 500 mg of PLGA in methylene chloride at a 5% w/v ratio. 50 mg of vitamin D3 (Cayman Chemical) in 1 mL of methanol (Thermo Fisher Scientific) was loaded directly into the methylene chloride/PLGA solution and set to shake at 150 rpm for 10 min. This solution was then added to 50 mL of 5% w/v PVA and homogenized at 35,000 rpm for 180 s using a tissue-miser homogenizer (Thermo Fisher Scientific) to form an oil-in-water emulsion. The microparticle solution was subsequently added to a beaker of 100 mL 1% PVA and set to stir for 4e6 h for solvent evaporation and microparticle hardening to occur. For water-soluble $MOG_{35-55}$- (Mimotopes, Victoria, Australia) and $OVA_{323-339}$-encapsulated (Mimotopes) MPs, 4 mg of peptide in 200 mL PBS was added to the 5% methylene chloride/PLGA solution and homogenized at 35,000 rpm for 120 s to form a primary emulsion. This emulsion was added to 50 mL of 5% PVA and homogenized again at 35,000 rpm for 180 s to form the secondary emulsion, and added to 100 mL of stirring 1% PVA.

Non-phagocytosable MPs encapsulating TGF-β1 and GM-CSF were fabricated by first dissolving 500 mg of PLGA in methylene chloride at a 20% w/v ratio. Human TGF-β1 (Peprotech) was reconstituted in 10 mM hydrochloric acid and 2 mg/mL bovine serum albumin in 250 mL PBS and recombinant mouse GM-CSF (Biolegend) was reconstituted in 400 mL PBS. Protein solutions were added to the methylene chloride/PLGA solution and vortexed (Thermo Fisher Scientific) at the highest setting (~3200 rpm) for 30 s to generate the primary emulsion. This emulsion was added to 5 mL of 2.5% PVA and vortexed again at 3200 rpm for 60 s to form the secondary emulsion, and finally added to 100 mL of stirring 1% PVA. Either methanol or PBS was used to generate unloaded MPs, depending on the control group being fabricated. After 4-6 h, solutions were centrifuged at 10,000 g for 10 min to collect MPs and washed three times with ultrapure water. The resultant MPs were then flash-frozen in liquid nitrogen and lyophilized for 24 h. The MPs were stored at −20° C. until their use.

Example 3: Microparticle Characterization

The size distributions of MPs were measured by the Beckman Coulter LS13320 (Beckman Coulter Inc., Brea, CA) and the Microtrac Nanotrac Dynamic Light Scattering Particle Analyzer (Microtrac, Montgomery, PA). The MP diameter is reported as mean±standard deviation and displayed as a volume percentage.

Encapsulation efficiencies of proteins/peptides was assessed by μBCA (Thermo Fisher Scientific). Briefly, a known mass of MPs, as determined by the working range of the μBCA assay, was dissolved in a 0.2 M NaOH/5% sodium dodecyl sulfate (SDS) solution. An analogous process with unloaded MPs and soluble drug was performed. The pH of solutions was neutralized with a small volume of HCl and protein/peptide concentration measured by μBCA assay. Serial dilutions of the unloaded MP/soluble drug solution determined the encapsulation efficiency. Vitamin D3 MPs were measured by dissolving 100 mg of MPs into 2 mL MC and re-precipitating the PLGA with a known volume of methanol. The suspension was centrifuged and the supernatant removed to a new tube. Following evaporation, residue remaining in the tube was concentrated in a known, small quantity of DMSO and the solution concentration measured by spectrophotometer.

Advantageously, compared to prior formulations, the MP formulations used in the instant invention have been modified by increasing the loading of immunomodulatory factors.

Consistent sizing of phagocytosable MPs, ~0.8 μm-diameter, and non-phagocytosable MPs, ~55 m-diameter, irrespective of the drug loaded was demonstrated, highlighting the dual-sized nature of the dMP system (FIG. 1A). The encapsulation efficiencies for the small phagocytosable MPs were 48.6±9.0%, 65.5±3.0%, and 49.9±2.8% for $MOG_{35-55}$, vitamin D3, and $Ova_{323-339}$ MPs, respectively (FIG. 1B). Comparable encapsulation efficiencies for the large non-phagocytosable MPs were observed, with 44.2±12.1% and 58.3±9.4% for TGF-b1 and GM-CSF MPs, respectively (FIG. 1B).

Example 4: Site of Injection Analysis and Microparticle Trafficking

C57BL/6 mice (B6NTac) were purchased from Taconic Biosciences. All animals were housed in specific pathogen free conditions. All experiments were conducted on 8-20-week old male or female mice.

Characterization of nodules at the site of injection was carried out via flow cytometry and H&E staining. Initial studies characterizing DC recruitment and phenotype used a mixed cohort of 8-20-week-old male and female C57BL/6 mice. Animals were injected subcutaneously in the abdominal region using 20 G needles (BD Biosciences). MP injections consisted of 10 mg of MPs total (1:1:1:1 MP mass ratio) in 0.2 mL PBS. Nodules were excised 8 days after injection, enzymatically digested with 2 mg/mL collagenase type XI (Sigma-Aldrich, St. Louis, MO, USA) at 37° C. for 30 min, filtered through a 30 μm filter to remove large particulates, and isolated cells stained for flow cytometry. For immunohistochemistry, nodules were fixed in 10% formalin overnight at 4° C., processed and embedded in paraffin blocks and stained.

Microparticle uptake in the nodule and trafficking to secondary lymphoid organs was assessed by loading the phagocytosable MPs concomitantly with Vybrant DiO (Invitrogen) fluorescent labelling dye and vitamin D3 or an irrelevant protein (denatured insulin). Non-drug loaded (unloaded) phagocytostable fluorescent MPs were also fabricated. Large, non-phagocytosable MPs were fabricated in the standard fashion without the addition of fluorescent dye.

At various time points (24 h, 48 h, and 8 d) after subcutaneous injection in the abdominal region mice were euthanized and cells were isolated from various secondary lymphoid organs. Cells were stained with primary conjugated antibodies and analyzed via flow cytometry.

Example 5: Evaluation of Tolerogenic Factors in the Blood

A mixed cohort of 10-week old male and female C57BL/6 mice were injected subcutaneously in the mid-dorsal region with the dual-sized microparticle (dMP) formulation using 20 G needles (BD Biosciences). Blood was collected from submandibular vein of animals on days 2, 4, and 7 after subcutaneous dMP injection, processed for serum, and GM-CSF and TGF-$\beta$1 serum concentrations were measured using enzyme linked immunosorbent assay (ELISA) following the manufacturer's protocol (BD Biosciences, cat #555167, 559119). A negative control group of C57BL/6 mice received no treatment. Conversely, a positive control group of C57BL/6 mice were injected intravenously with GM-CSF and TGF-$\beta$1 at a dose 1/10th of that delivered in the dMP immediately prior to blood collection. Absorbance was read at 450 nm using a SpectraMax M3 microplate reader (Molecular Devices) and serum concentrations of GM-CSF and TGF-$\beta$1 was calculated using a standard curve performed following manufacturer's protocol (BD Biosciences).

Example 6: EAE Induction

EAE was induced in 10-11-week old female C57BL/6 mice from Taconic Biosciences with Hooke Kit™ (Hooke Laboratories Inc., Cat #EK-2110). Briefly, 100 mL of $MOG_{35-55}$/CFA emulsion was injected subcutaneously in the anterior and posterior dorsal regions for a total of 200 mL emulsion per mouse, according to manufacturer's protocol. Pertussis toxin (100 mL of 4 mg/mL) was injected intraperitoneally 2 h and 24 h following $MOG_{35-55}$/CFA emulsion injection, according to manufacturer's protocol. Clinical scoring was established as follows: score 1: flaccid tail, score 2: weak hind limbs, score 3: hind limb paralysis, score 4: quadriplegia, score 5: moribund, euthanasia.

Example 7: Dual MP Treatment in EAE Mice

For a total of 10 mg of dMP formulation per EAE mouse, 2.5 mg of each of the four MPs described in EXAMPLE 1 were mixed. Dual MPs were resuspended in 200 mL PBS per 10 mg of dMP. EAE mice were injected subcutaneously in the mid-dorsal region between the two $MOG_{35-55}$/CFA emulsion injection sites on the indicated days following EAE induction.

Figure 2A:
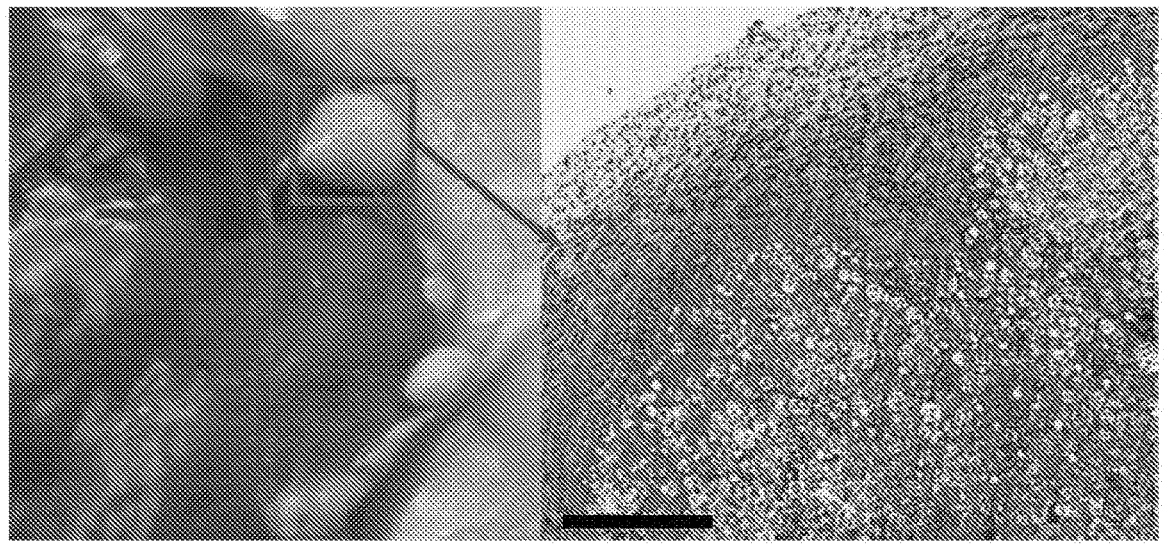
FIGS. 2A-2M show subcutaneous DC recruitment and tolerization, and microparticle-associated cell trafficking to local lymph nodes in vivo.

Example 8: Subcutaneous DMP Administration Causes DC Recruitment and Tolerization and Microparticle-Associated Cell Trafficking to Local Lymph Nodes without Systemic Release The capacity of the dMP formulation to recruit and tolerize DCs at the local injection site was evaluated and the ability of the cells that phagocytosed MPs to subsequently traffic to draining lymph nodes. Mice that received the dMP developed palpable nodules at the subcutaneous injection site a day after a single dMP injection. Surgical and histopathological analysis of the dMP nodules eight days after administration demonstrated high levels of proteinaceous deposition with significant nucleated cell infiltration surrounding the readily visible non-phagocytosable MPs (large white spheres) (FIG. 2A). Importantly, these nodules were resorbed within a month of injection as determined by palpation and surgical examination, approximately by the time the administered PLGA bolus completely degraded.

Figure 2B:
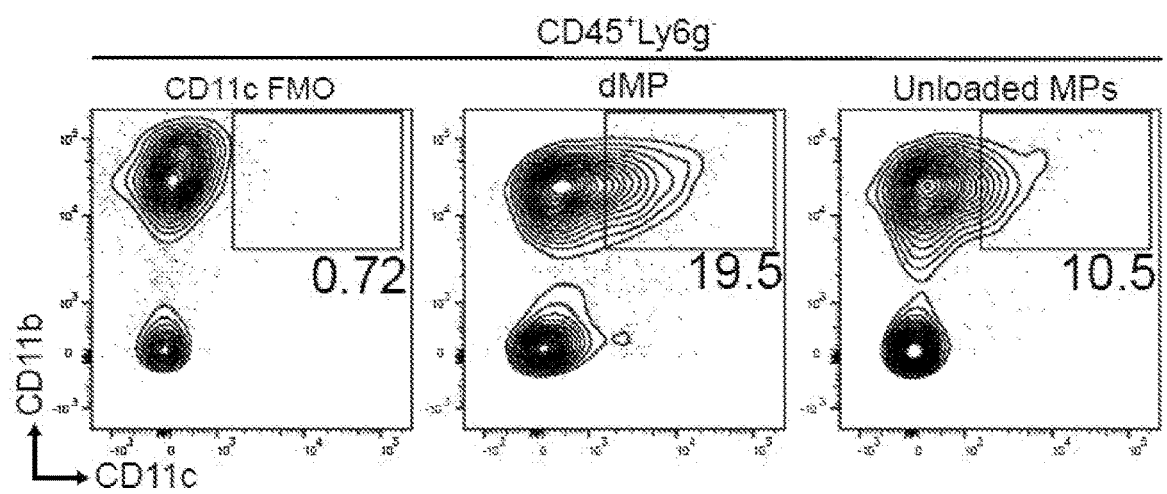
Figure 2C:
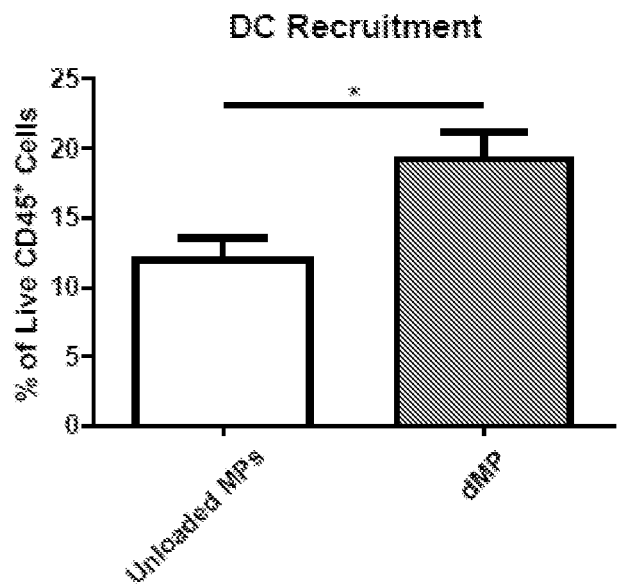
Figure 2D:
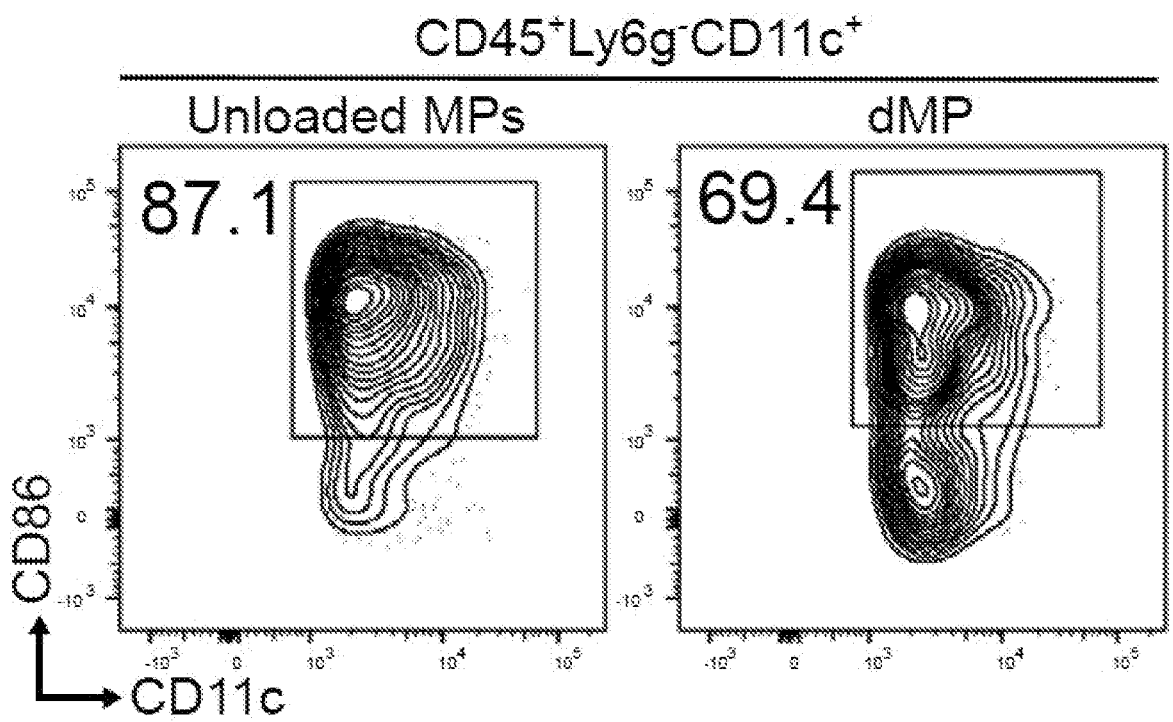
Figure 2E:
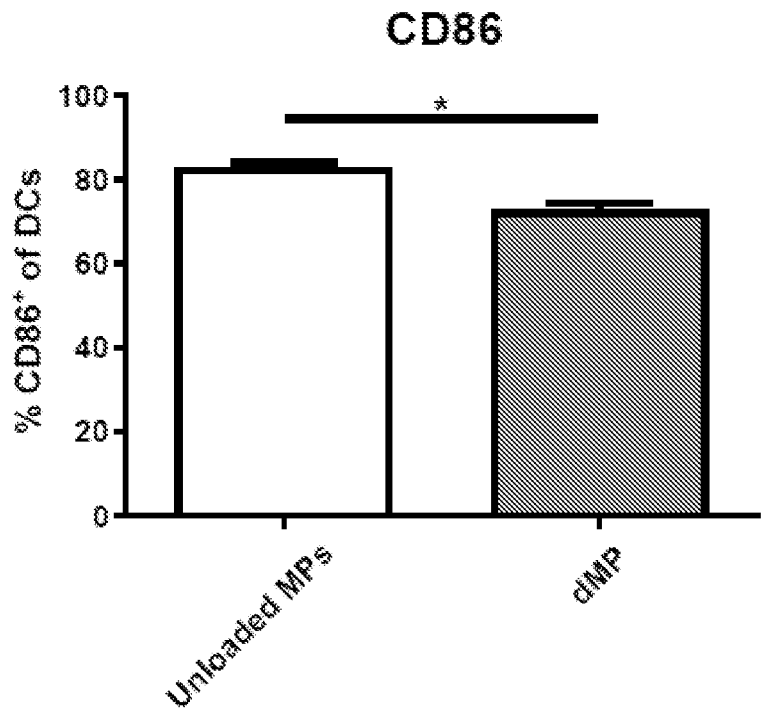

The composition of nodule-recruited cells was assessed by digestion of the nodule and flow cytometry analysis. DC recruitment to the local subcutaneous MP nodule was improved when MPs were loaded with bioactive factors compared to unloaded MPs, with the total frequency of infiltrating DCs rising from 11.9% to 19.2% of total $CD45^+$ cells (FIG. 2B-C). Furthermore, recruited DCs demonstrated characteristics of a non-activated phenotype, with decreased frequency of $CD86^+$ DCs in the case of loaded MPs versus unloaded (FIG. 2D-E).

Figure 2F:
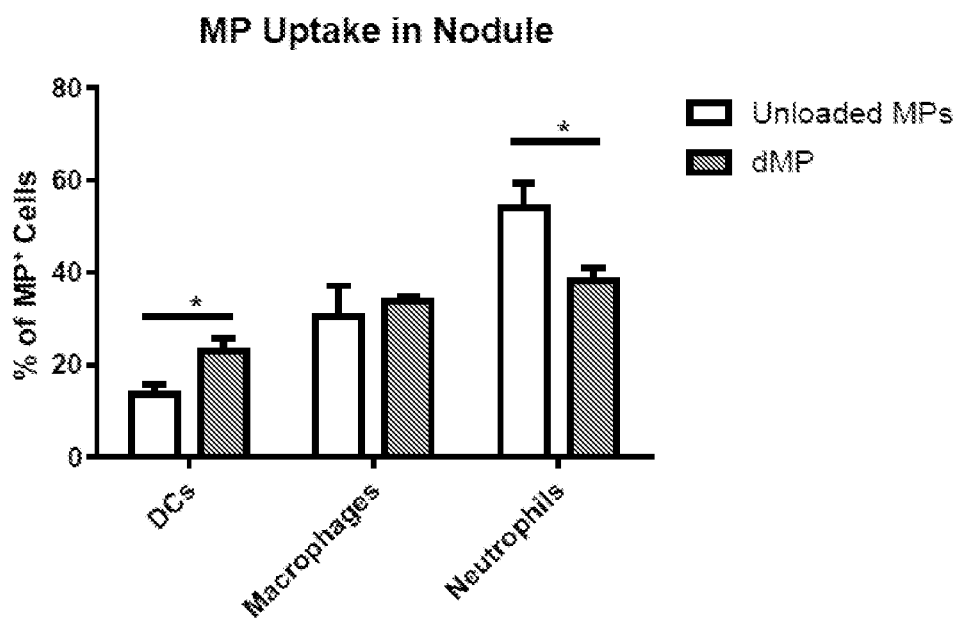
Figure 2G:
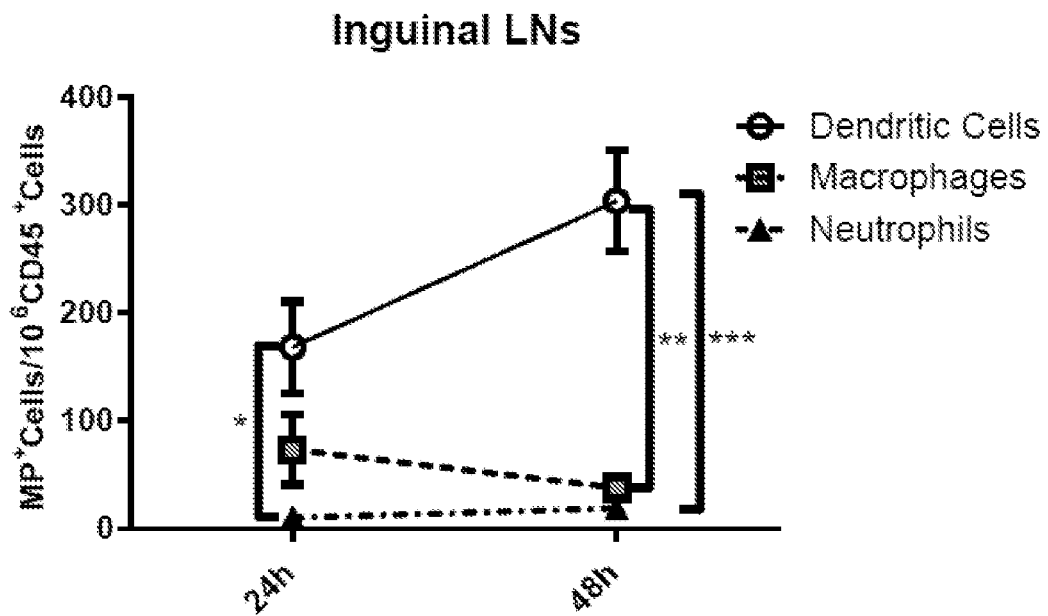
Figure 2H:
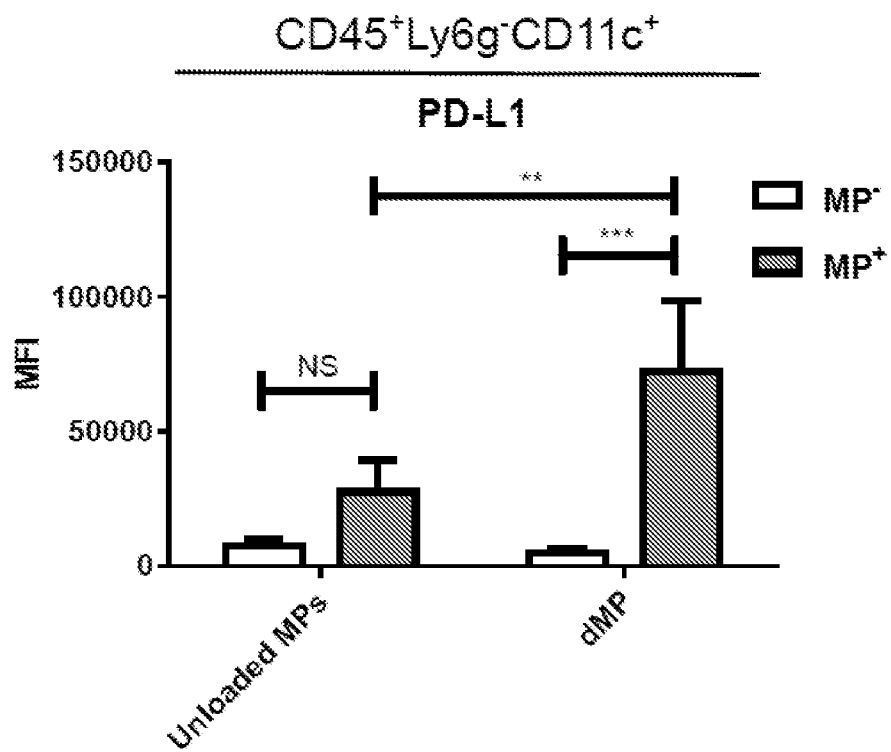
Figure 2I:
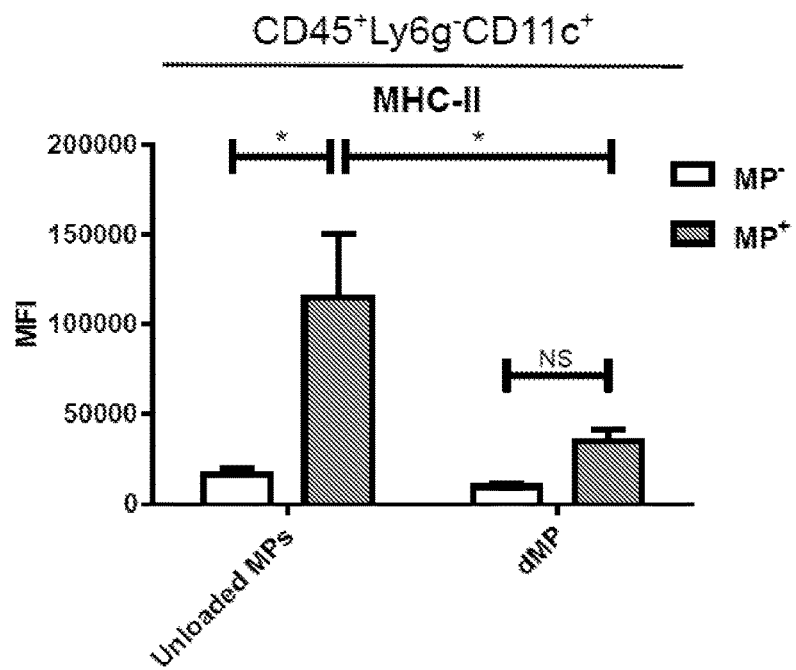

Using fluorescently-loaded phagocytosable MPs in the dMP formulation, MP uptake in the nodule was assessed in phagocyte populations. Higher uptake of the phagocytosable dMP particles compared to unloaded MPs by DCs was evident, while the uptake of dMPs versus unloaded MPs was equivalent in macrophages and lower in neutrophils (FIG. 2F). Trafficking of phagocytes associated with microparticles ($MP^+$ cells) was assessed in various peripheral lymphoid organs at multiple time points (FIG. 2G-K). At 24 and 48 h post-dMP injection, $MP^+$ DCs were shown to drain to inguinal lymph nodes (ILNs) in the highest number compared to neutrophils (24 h) and both macrophages and neutrophils (48 h) (FIG. 2G). Notably, $MP^+$ DCs isolated from ILNs 24 h after MP injection demonstrated upregulation of programmed death-ligand 1 (PD-L1) expression compared to $dMP^-$ DCs or unloaded $MP^+$ DCs, while PD-L1 expression between unloaded $MP^+$ and unloaded $MP^-$ DCs remained unchanged (FIG. 2H). Similarly, $dMP^+$ DCs isolated from ILNs 48 h after MP injection maintained immature phenotypes, whereas unloaded $MP^+$ DCs significantly upregulated MHC-II expression compared to unloaded $MP^-$ DCs (FIG. 2I).

Figures 2J, 2K:
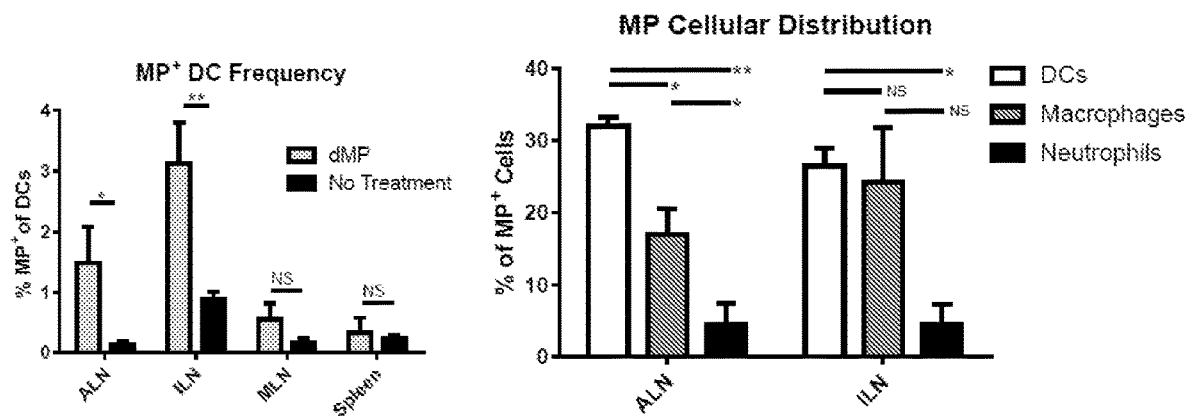
Figure 2L:
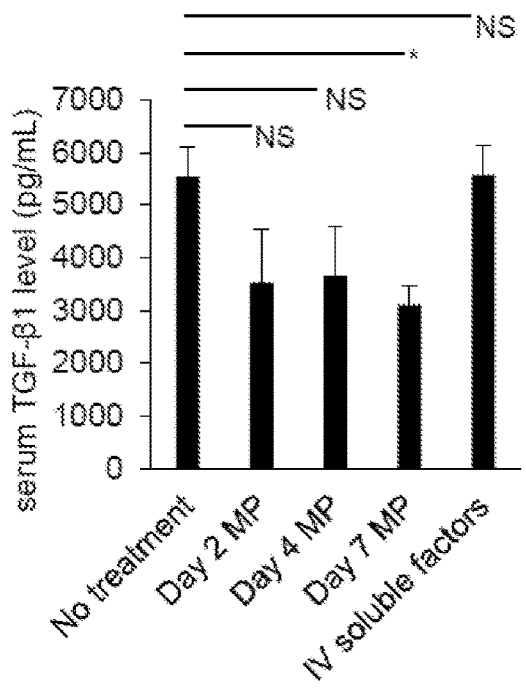
Figure 2M:
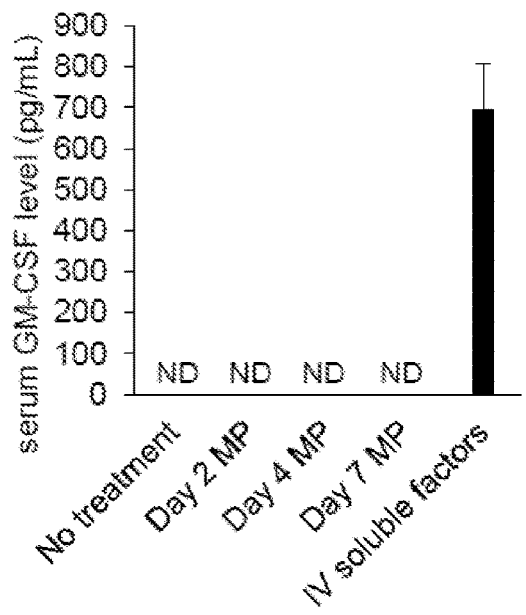

At a later time point, eight days after dMP administration, $MP^+$ DCs were present in proximal draining lymph nodes (axillary [ALNs] and ILNs), however not in distal lymphoid organs (mesenteric lymph nodes and spleen) (FIG. 2J), thus minimizing the potential for systemic immunosuppression. Upon further examination, $MP^+$ DCs had the highest frequency in ALNs, followed by $MP^+$ macrophages, while in ILNs the frequency of $MP^+$ DCs and $MP^+$ macrophages was equivalent (FIG. 2K). The frequency of $MP^+$ neutrophils was low both in ALNs and ILNs. In addition, subcutaneous injection of the dMPs did not result in serum elevation of TGF-$\beta$1 or GM-CSF at 2, 4, and 7 days compared to no treatment (FIG. 2L-M), suggesting that systemic immunosuppression is unlikely.

In sum, these proof-of-concept studies emphasize the feasibility of this platform to modulate DC recruitment and phenotype, as well as the distribution of the MP-loaded cells proximally, but not into the distal lymphoid organs or systemically.

Figure 3A:
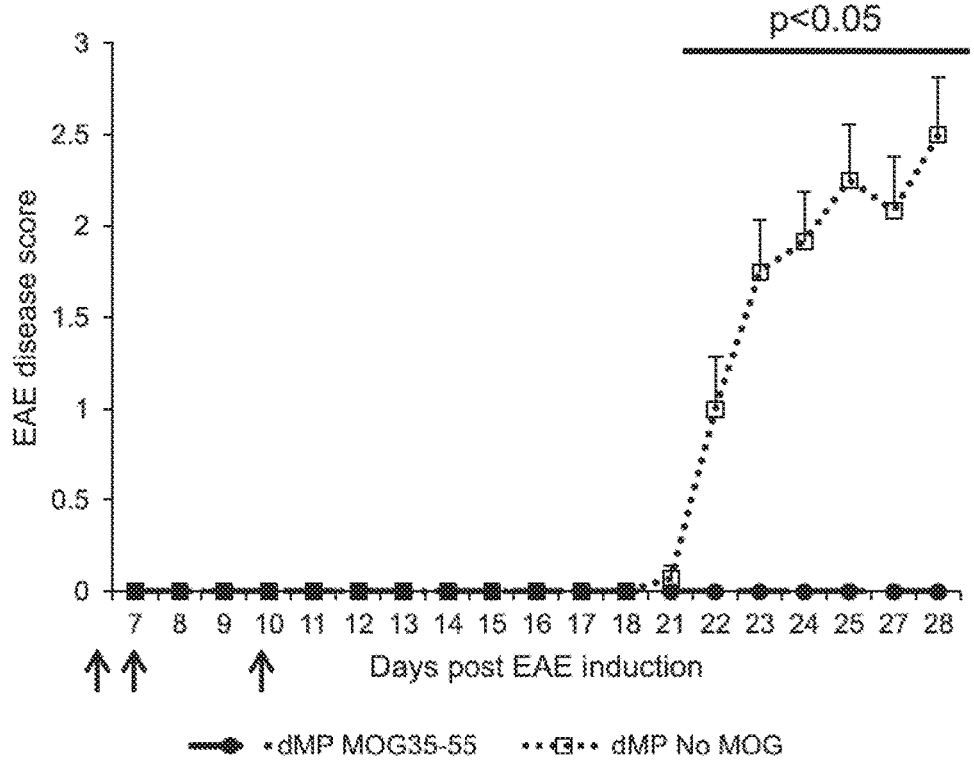
FIGS. 3A-3B show that the $dMP-MOG_{35-55}$ formulation blocks experimental autoimmune encephalomyelitis in a treatment setting.
Figure 3B:
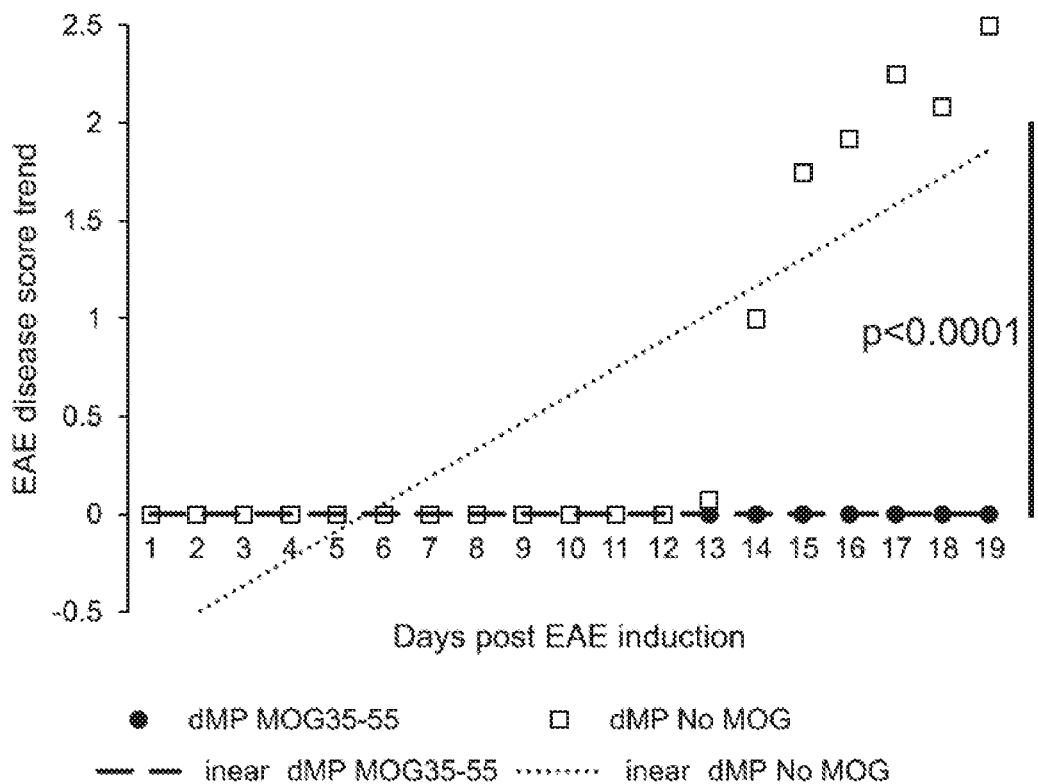

Example 9: dMP-$MOG_{35-55}$ Formulation Blocks Experimental Autoimmune Encephalomyelitis in a Semi-Therapeutic Treatment Setting It was examined whether the dMP system formulated with the antigenic $MOG_{35-55}$ peptide (dMP-$MOG_{35-55}$) can be used to treat EAE, the mouse model for multiple sclerosis (MS). Specifically, the dMP-$MOG_{35-55}$ formulation, consisting of non-phagocytosable TGF-$\beta$1 and GM-CSF MPs and phagocytosable vitamin D3 and MOG$_{35-55}$ MPs (dMP-MOG$_{35-55}$), was used. The dMP formulation without MOG$_{35-55}$ consisting of non-phagocytosable TGF-β1 and GM-CSF MPs, phagocytosable vitamin D3 MPs, and unloaded phagocytosable MPs was used as control (dMP No MOG). The dMP-MOG$_{35-55}$ treatment and the corresponding control were administered subcutaneously on days 4, 7, and 10 following EAE induction in C57BL/6 mice. The results show that EAE mice treated with the dMP-MOG$_{35-55}$ developed minimal EAE scores in significant contrast to EAE mice treated with the dMP No MOG (FIG. 3A). Linear regression analysis of EAE disease score development revealed no disease development in EAE mice treated with dMP-MOG$_{35-55}$ compared to positive disease progression in EAE mice treated with dMP without MOG$_{35-55}$ (FIG. 3B). Thus, these results demonstrate that early administration dMP-MOG$_{35-55}$, after disease induction, is highly efficacious in the prevention of EAE disease.

Figure 4A:
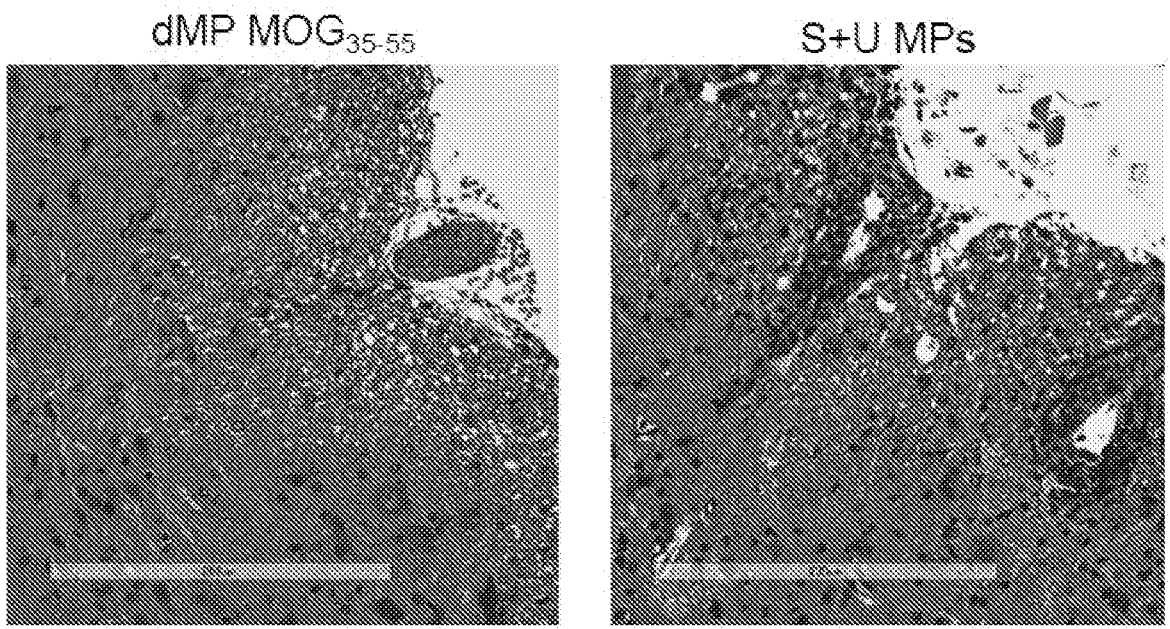
FIGS. 4A-4C show that EAE mice treated with dMP-$MOG_{35-55}$ have reduced leukocytes and $CD4^+$ T cells infiltrating into the CNS.

Example 10: EAE Mice Treated with dMP-MOG$_{35-55}$ have Reduced Leukocytes and CD4$^+$ T Cells Infiltrating into the CNS The hallmark of active MS and EAE is mononuclear immune infiltration into the CNS [4,9]. Histopathological examination of spinal cord sections from EAE mice revealed perivascular cuffing with mononuclear inflammatory cells as well as extension of mononuclear inflammatory cell infiltrate into parenchyma in mice treated with the control of soluble factors (equivalent doses of TGF-β1, GM-CSF, vitamin D3 and MOG$_{35-55}$ peptide) co-administered with empty MPs (S+U MPs) (FIG. 4A). However, spinal cord sections of EAE mice treated with dMP-MOG$_{35-55}$ revealed an intact parenchyma with the absence of perivascular mononuclear inflammatory cells, indicating that the dMP-MOG$_{35-55}$ treatment prevented EAE disease development through successfully blocking inflammatory cell infiltrating into the CNS. Lymphocyte infiltration into the CNS is observed in early and active MS and EAE and is considered the cause of autoimmune pathogenesis [4].

Figure 4B:
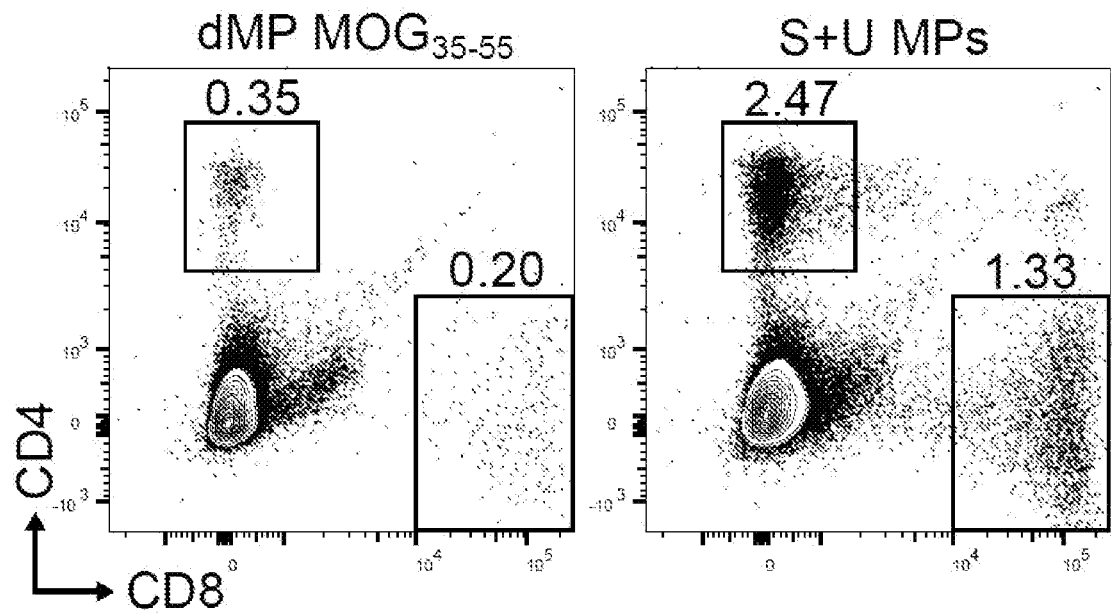
Figure 4C:
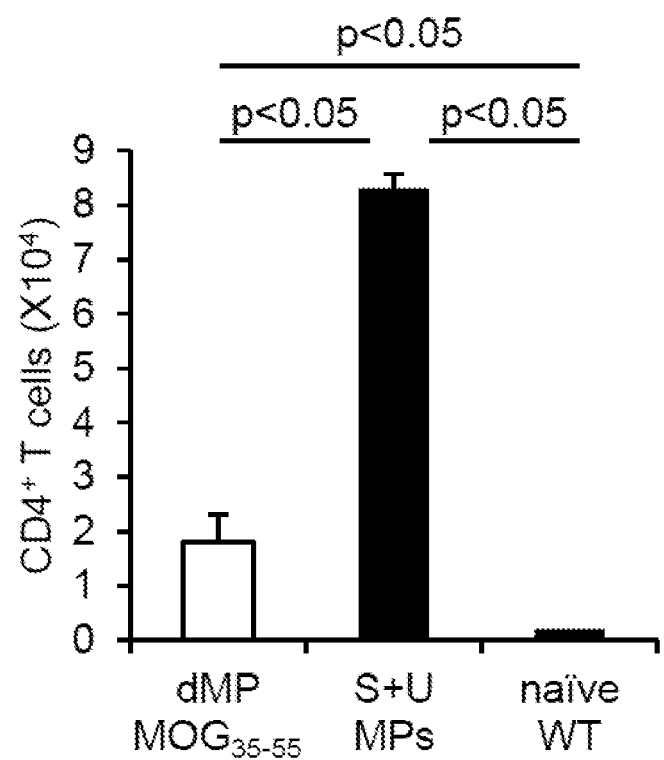

The percentages and absolute numbers of T cells in the CNS of dMP-MOG$_{35-55}$ versus S+U MPs-treated EAE mice and naïve mice were evaluated by flow cytometry. The percentages and absolute numbers of CD4$^+$ T cells were drastically reduced in the EAE mice treated with dMP-MOG$_{35-55}$, but still slightly higher than that of naïve healthy mice (FIG. 4B, C). Thus, the dMP-MOG$_{35-55}$ treatment reduced the total mononuclear inflammatory cell infiltrating into the CNS (FIG. 4A) in EAE mice, and also significantly reduced the total number of CD4$^+$ T cells infiltrating into the CNS (FIG. 4C), which indicates that dMP-MOG$_{35-55}$ prevents EAE disease development through impeding CD4$^+$ T cell infiltration in the CNS.

Figure 5A:
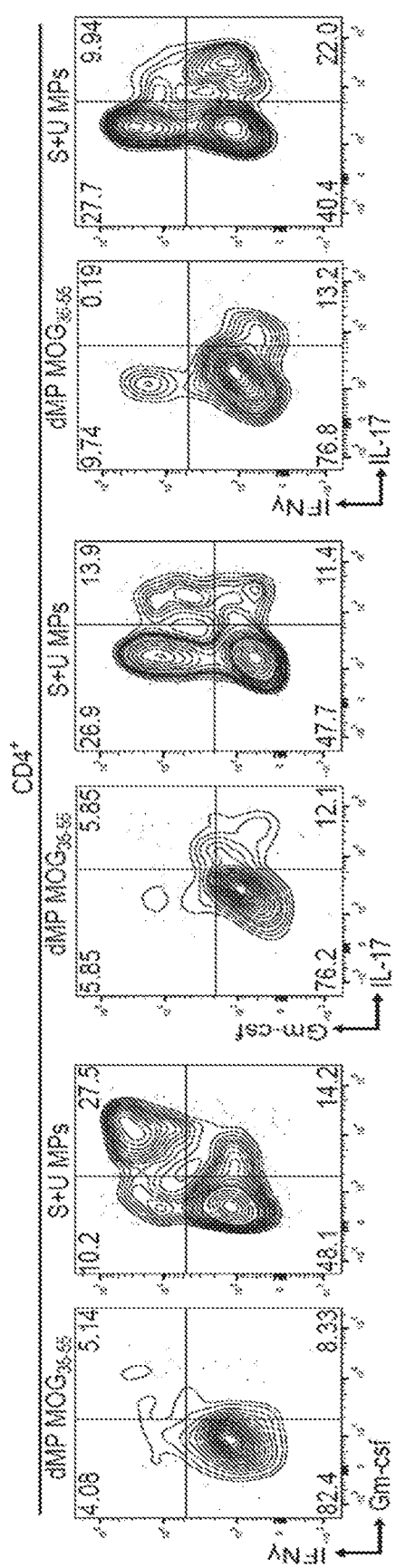
FIGS. 5A-5B show that EAE mice treated with dMP-$MOG_{35-55}$ have reduced $CD4^+$ T cells producing IL-17A, GM-CSF and IFNγ in the CNS.
Figure 5B:
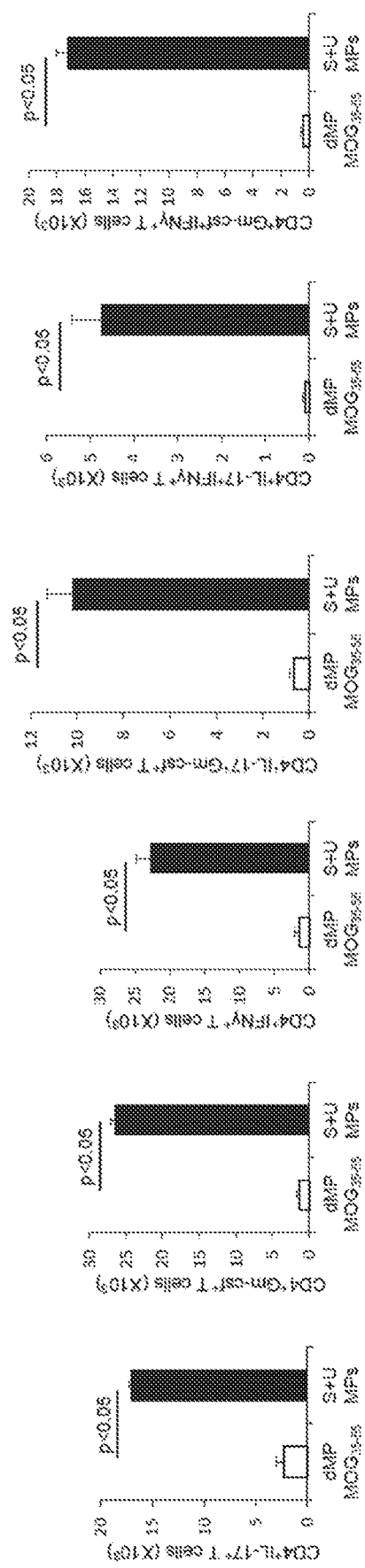

Example 11: EAE Mice Treated with dMP-MOG$_{35-55}$ have Reduced CD4$^+$ T Cells Producing IL-17A, GM-CSF and IFNγ in the CNS Given that production of proinflammatory cytokines IL-17A, GM-CSF, and IFNγ by pathogenic autoreactive CD4$^+$ T cells is critical in the EAE disease pathogenesis [14,32], it was examined whether dMP-MOG$_{35-55}$ treatment suppressed production of these proinflammatory cytokines. Not only was the number of CNS-infiltrating CD4$^+$ T cells reduced in EAE mice treated with dMP-MOG$_{35-55}$, but the production of IL-17A, GM-CSF, IFNγ, and co-production of these cytokines by the few CNS-infiltrating CD4$^+$ T cells was also severely reduced in EAE mice treated with dMP-MOG$_{35-55}$ (FIG. 5). Both the frequencies (FIG. 5A) and absolute numbers (FIG. 5B) of IL-17A, GM-CSF, IFNγ, and dual cytokine-producing CD4$^+$ T cells in the CNS were significantly reduced in EAE mice treated with dMP-MOG$_{35-55}$, suggesting that in addition to preventing the infiltration of CD4$^+$ T cells in the CNS, dMP-MOG$_{35-55}$ also suppress the production of IL-17A, GM-CSF, and IFNγ by pathogenic CD4$^+$ T cells.

Figure 6A:
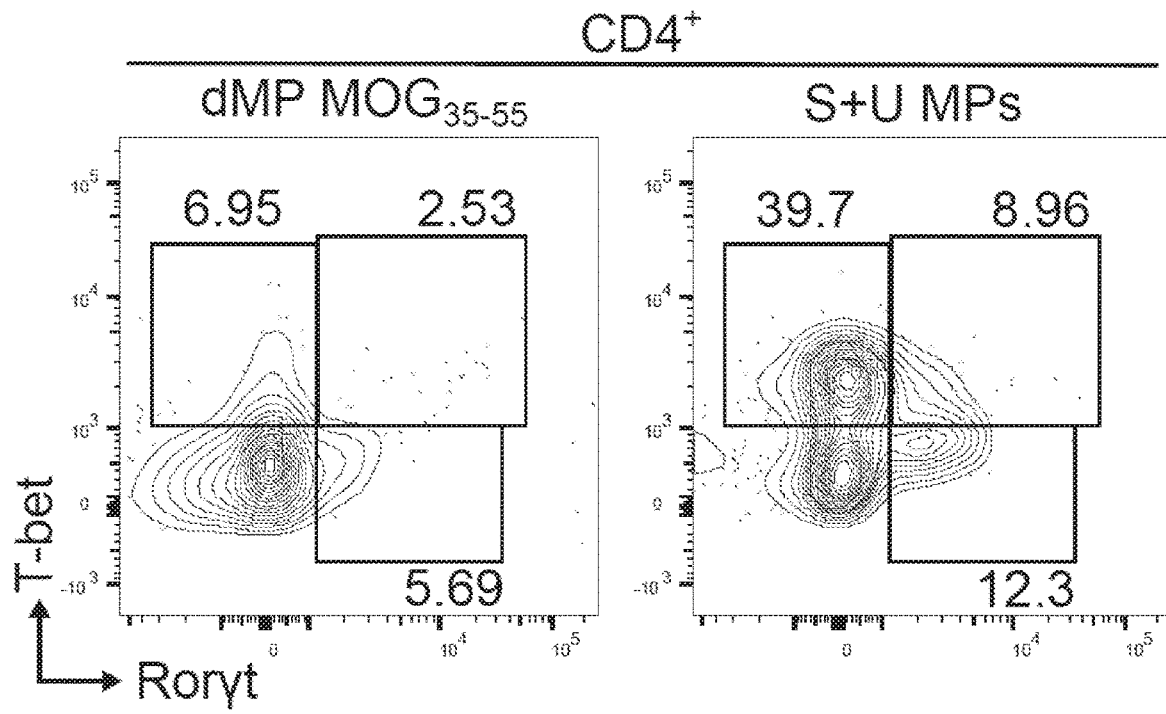
FIGS. 6A-6B show that EAE mice treated with dMP-$MOG_{35-55}$ have decreased pathogenic $CD4^+$ T cells expressing the transcription factors Rorγt and T-bet in the CNS.
Figure 6B:
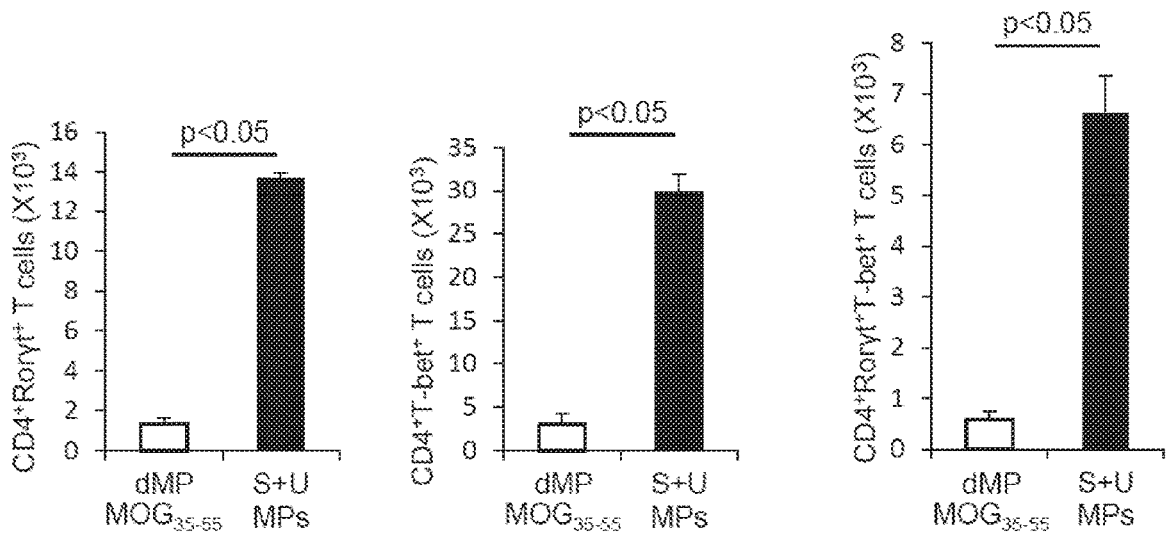

Example 12: EAE Mice Treated with dMP-MOG$_{35-55}$ have Decreased Pathogenic CD4$^+$ T Cells Expressing the Transcription Factors RORγT and T-bet in the CNS The Th17 transcription factor, Rorγt, and the Th1 transcription factor, T-bet, have been demonstrated to be crucial for GM-CSF production in pathogenic CD4$^+$ T cells and EAE disease pathogenesis [13,15, 33-35]. It was, therefore, examined whether dMP-MOG$_{35-55}$ treatment suppressed Rorγt and T-bet expression in CD4$^+$ T cells in the CNS. EAE mice treated with dMP-MOG$_{35-55}$ showed significant reduction in frequencies and absolute numbers of Rorγt$^+$, T-bet$^+$, and dual Rorγt and T-bet-expressing CD4$^+$ T cells in the CNS (FIG. 6), as well as diminished Rorγt and T-bet mean fluorescence intensity as measure for the expression levels per cell. These results indicated that dMP-MOG$_{35-55}$ treatment can block the entire transcriptional program of pathogenic CD4$^+$ T cells in EAE mice. Thus, taken together, these results indicated that the reduced EAE disease scores in the dMP-MOG$_{35-55}$-treated EAE mice were linked to reduced pathogenic CD4$^+$ T cells in the CNS.

Figure 7A:
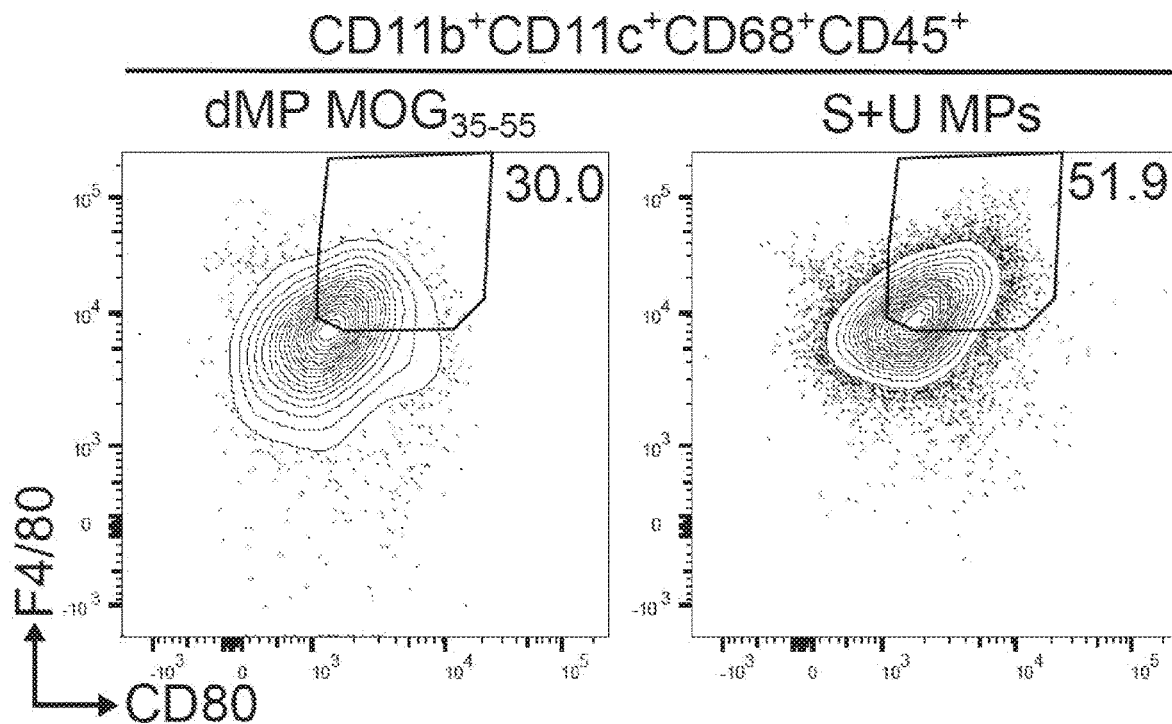
FIGS. 7A-7B show that activated macrophages/microglial cells are reduced in the CNS of mice treated with dMP-MOG$_{35-55}$.
Figure 7B:
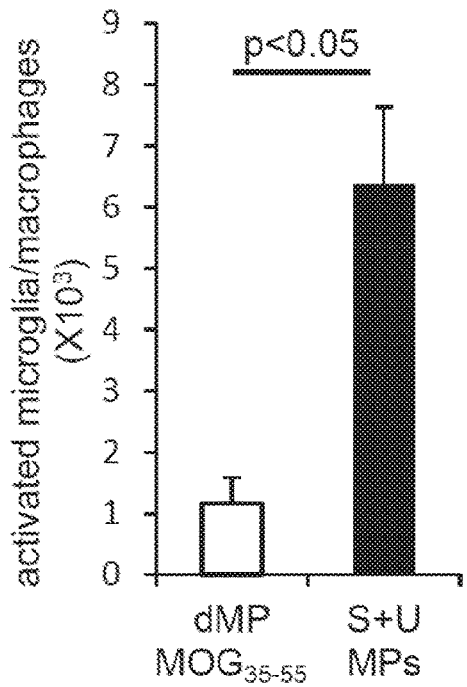

Example 13: Activated Macrophages/Microglial Cells are Reduced in the CNS of Mice Treated with MOG$_{35-55}$ In EAE and MS, pathogenic effector CD4$^+$ T cells trigger activation of CNS resident microglia and the recruitment of macrophages, which are essential for inflammatory demyelinating lesions [36]. It was therefore examined whether dMP-MOG$_{35-55}$ treatment affected activated microglia/macrophage populations in the CNS of EAE mice. Both microglia and macrophages are CD11b$^+$F4/80$^+$CD68$^+$ and upregulate MHCII and CD80 following activation [37, 38]. The frequency (FIG. 7A) and absolute number (FIG. 7B) of CD11b$^+$CD68$^+$F4/80$^+$CD80$^+$ cells, which include both activated macrophages and microglia, were significantly reduced in the CNS of EAE mice treated with dMP-MOG$_{35-55}$. These reductions are likely in relation to the decreased IL-17A, GM-CSF, and IFNγ production by CNS-infiltrating CD4$^+$ T cells (FIG. 4). Therefore, overall, the reduced EAE disease severity in mice treated with dMP-MOG$_{35-55}$ can be explained by the decreased pathogenic CD4$^+$ T cells and reduced activated macrophages/microglia in the CNS.

Example 14: Efficacy of DMP-Treatment is Dependent on Antigen Specificity

Figure 8A:
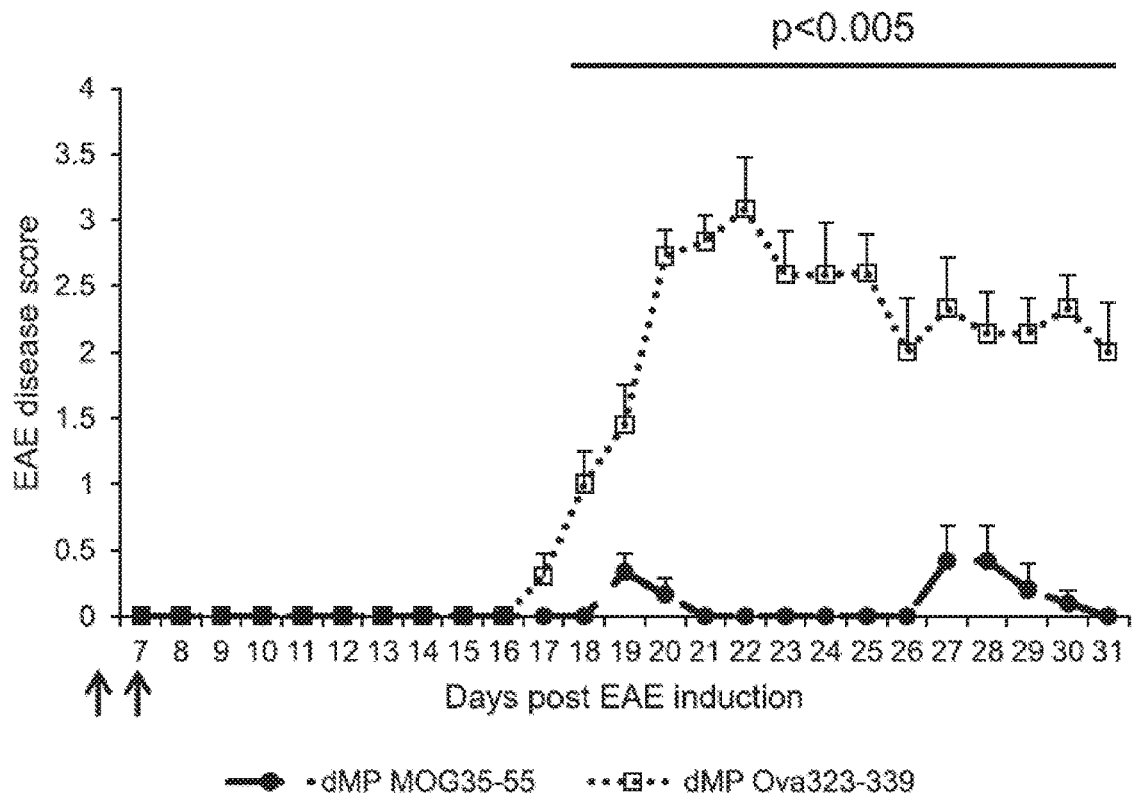
FIGS. 8A-8B show that the efficacy of dMP treatment is dependent on antigen specificity.
Figure 8B:
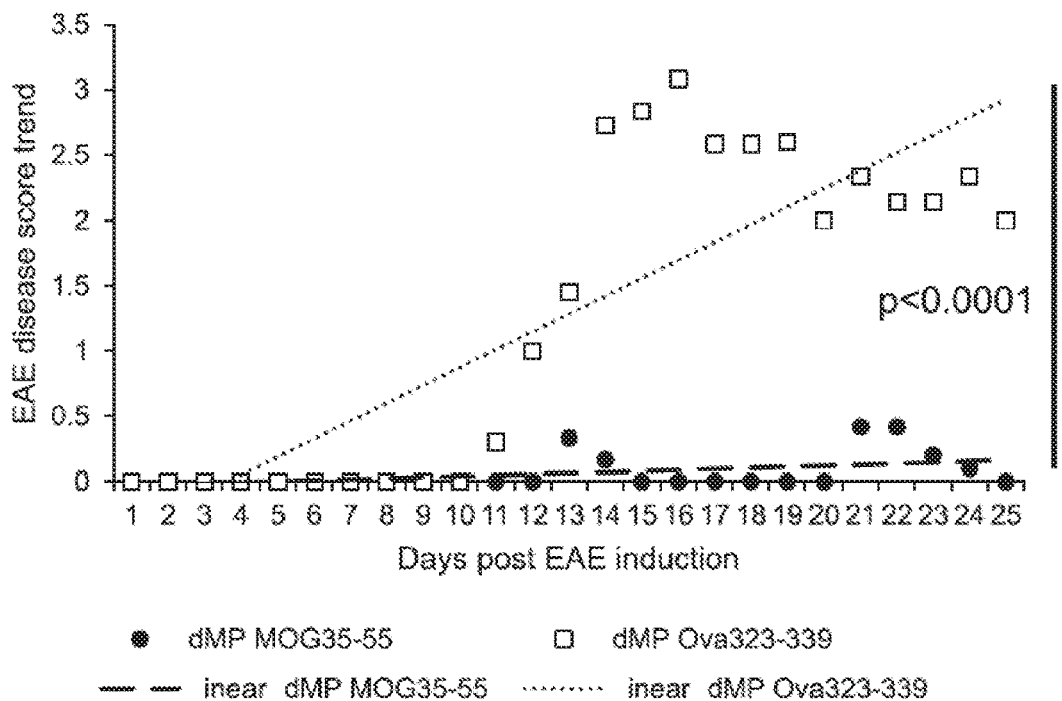

Because MS and EAE are established with a major autoimmune component [4], it was examined whether the dMP semi-therapeutic treatment was antigen-specific. EAE mice were treated with either dMP-MOG$_{35-55}$, which includes the MOG$_{35-55}$ antigenic peptide-loaded MPs, or dMP-Ova$_{323-339}$, which includes MPs loaded with an irrelevant antigenic peptide, Ova$_{323-339}$, derived from ovalbumin. Treatment with dMP-MOG$_{35-55}$ prevented EAE disease development, but treatment with dMP-Ova$_{323-339}$ did not (FIG. 8A). Linear regression analysis of EAE disease score development revealed no disease development in EAE mice treated with dMP-MOG$_{35-55}$ compared to positive disease progression in EAE mice treated with dMP-Ova$_{323-339}$ (FIG. 8B), thus demonstrating that the success of the treatment is dependent on antigen-specificity.

Figure 9A:
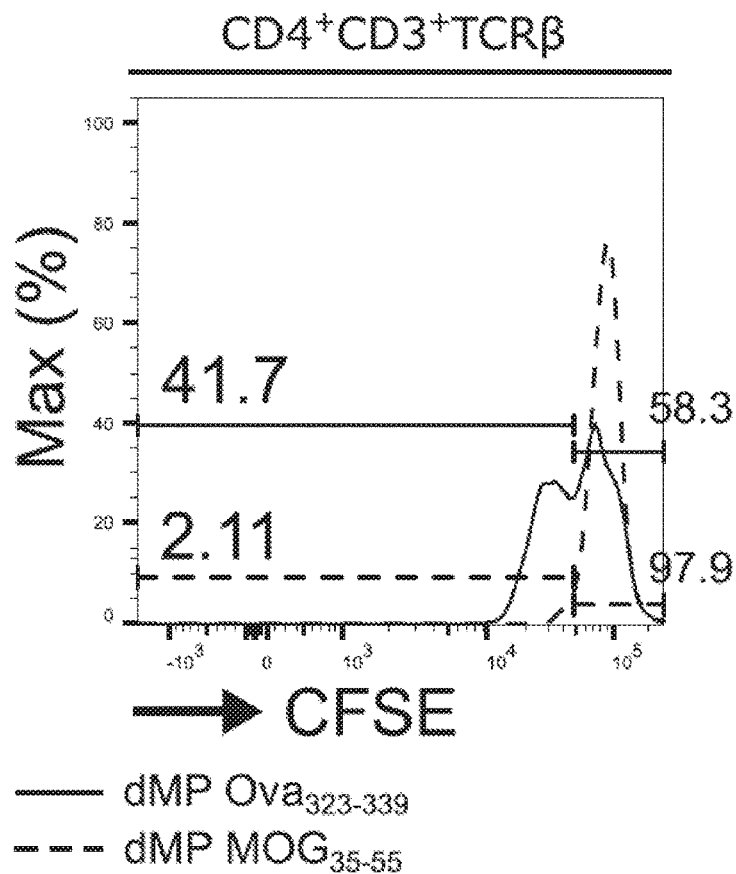
FIGS. 9A-9B show that T cells from EAE mice treated with dMP-MOG$_{35-55}$, but not with dMP-Ova$_{323-339}$, failed to expand in response to MOG$_{35-55}$-dependent stimulation.
Figure 9B:
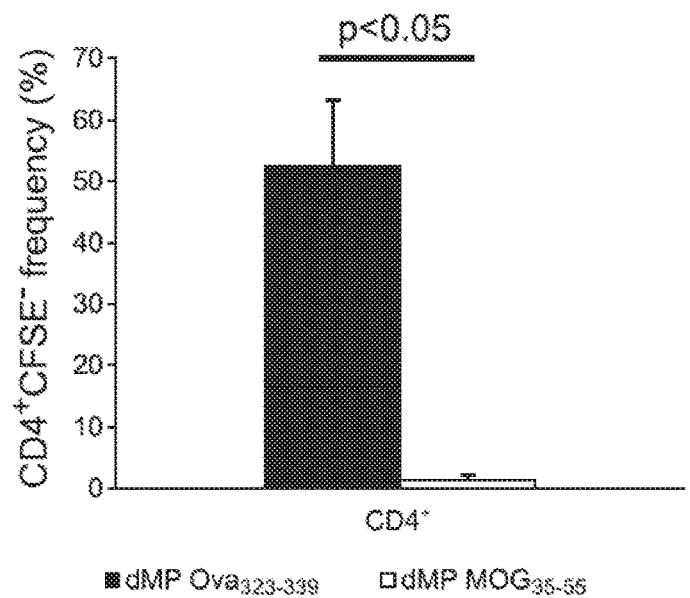

Example 15: T Cells from EAE Mice Treated with dMP-MOG$_{35-55}$, but not with DMP-Ova$_{323-339}$, Fail to Expand in Response to MOG$_{35-55}$-Dependent Stimulation Based on the demonstration that dMP-MOG$_{35-55}$ treatment of EAE is antigen-specific, it was investigated whether T cells isolated from dMP-MOG$_{35-55}$ treated EAE mice can proliferate as efficiently as T cells derived from EAE mice treated with dMP-Ova$_{323-339}$, following exogenous stimulation with splenocytes loaded with MOG$_{35-55}$ peptide, in an in vitro antigen re-stimulation assay. The results show that CD4$^+$ T cells isolated from dMP-MOG$_{35-55}$ treated EAE mice failed to proliferate, while CD4$^+$ T cells isolated from dMP-OVA$_{323-339}$ treated EAE mice expanded robustly in response to MOG$_{35-55}$-loaded splenocyte co-culture (FIG. 9). These results demonstrate that the T cells from dMP-MOG$_{35-55}$-treated EAE mice are anergic, i.e., unable to respond in an antigen-specific manner (FIG. 10).

Figure 10A:
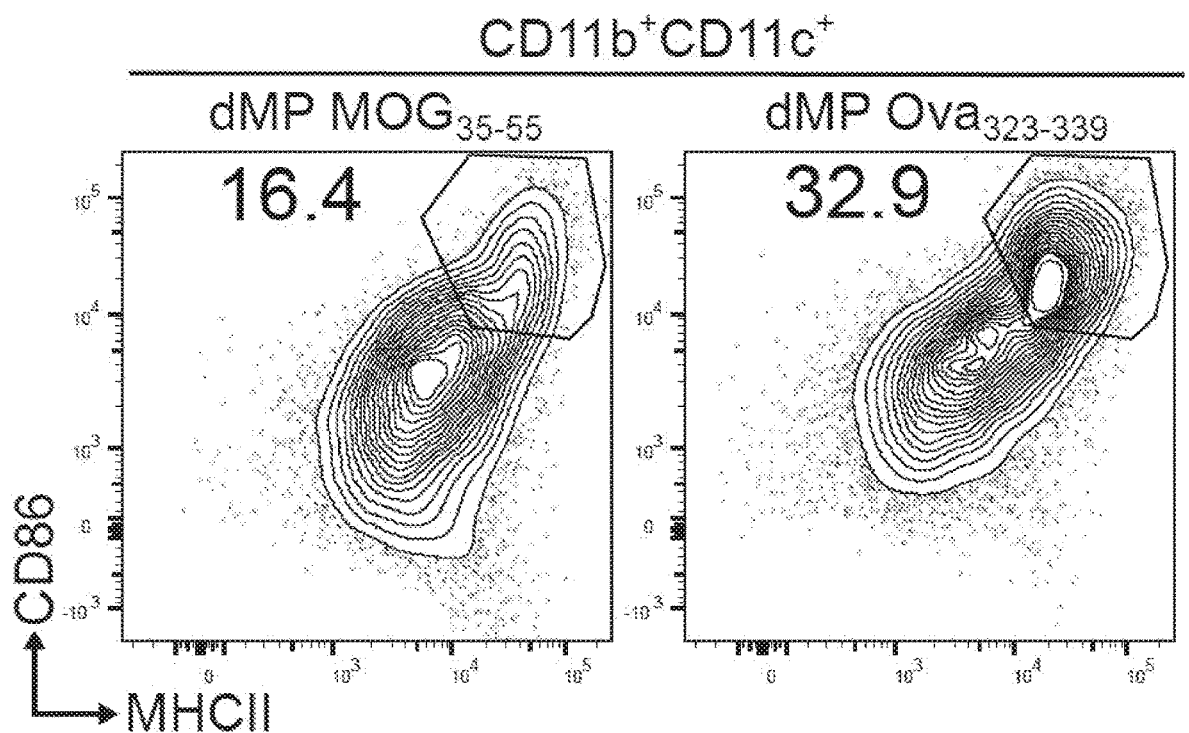
Figure 10B:
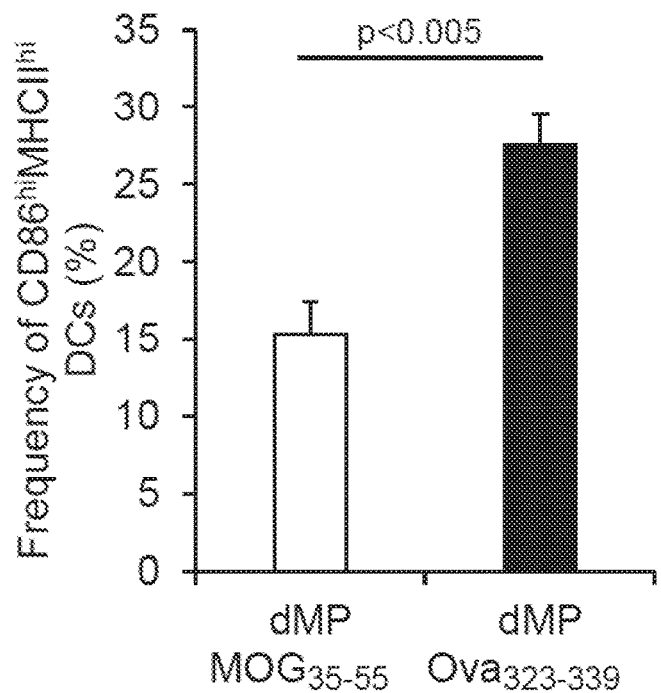

Example 16: Dendritic Cells from Draining Lymph Nodes of EAE Mice Treated with dMP-MOG$_{35-55}$ Display a Tolerized Phenotype It was investigated whether the dMP-MOG$_{35-55}$ treatment of EAE mice induced a suppressive DC phenotype, as indicated by reduced expression of CD86 and MHC-II. The frequency of CD11b$^+$CD11c$^+$ DCs that highly co-express CD86 and MHC-II in draining lymph nodes was significantly reduced in EAE mice treated with dMP-MOG$_{35-55}$ compared with those treated with irrelevant antigen-loaded dMP-Ova$_{323-339}$ (FIG. 10A-B). Similarly, the mean fluorescence intensity (MFI) of CD86 expression in dMP-MOG$_{35-55}$ was reduced (FIG. 10C). Therefore, not only are the CD4$^+$ T cells anergic in the dMP-MOG$_{35-55}$-treated group (FIG. 9), but the DCs are also suppressive in an antigen-specific manner (FIG. 10).

Figure 12:
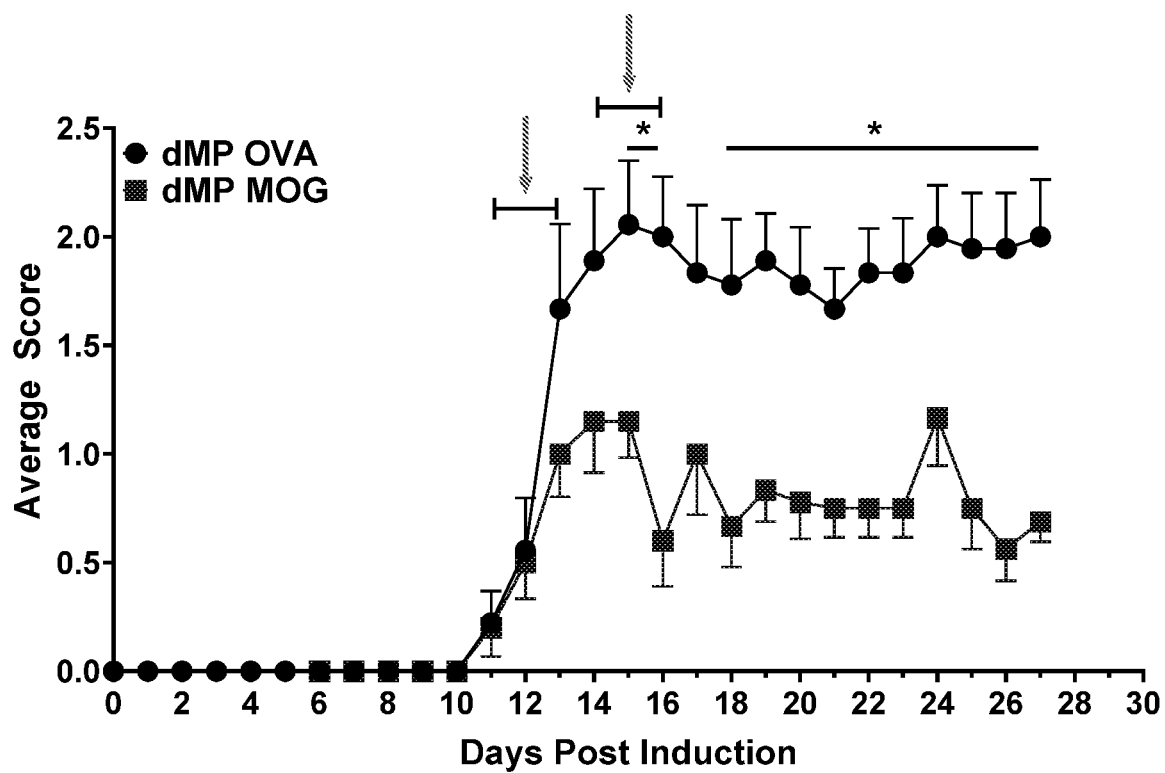
FIG. 12 shows that dMP MOG$_{35-55}$ treatment halts EAE when initiated at the onset of disease. EAE disease score (mean±SEM) of B6 mice treated with dMP MOG$_{35-55}$ (blue square) or dMP OVA$_{323-339}$ (black circle). Mice were induced with EAE and treated when they reached a score of one (onset) (first dose) and after three additional days (second dose). The range of days is due to rolling admission. n=5-7 per group. * denotes p<0.05 using Mann-Whitney U Test. Clinical scoring: score 1: flaccid tail, score 2: weak hind limbs, score 3: hind limb paralysis, score 4: quadriplegia.
Figure 13:
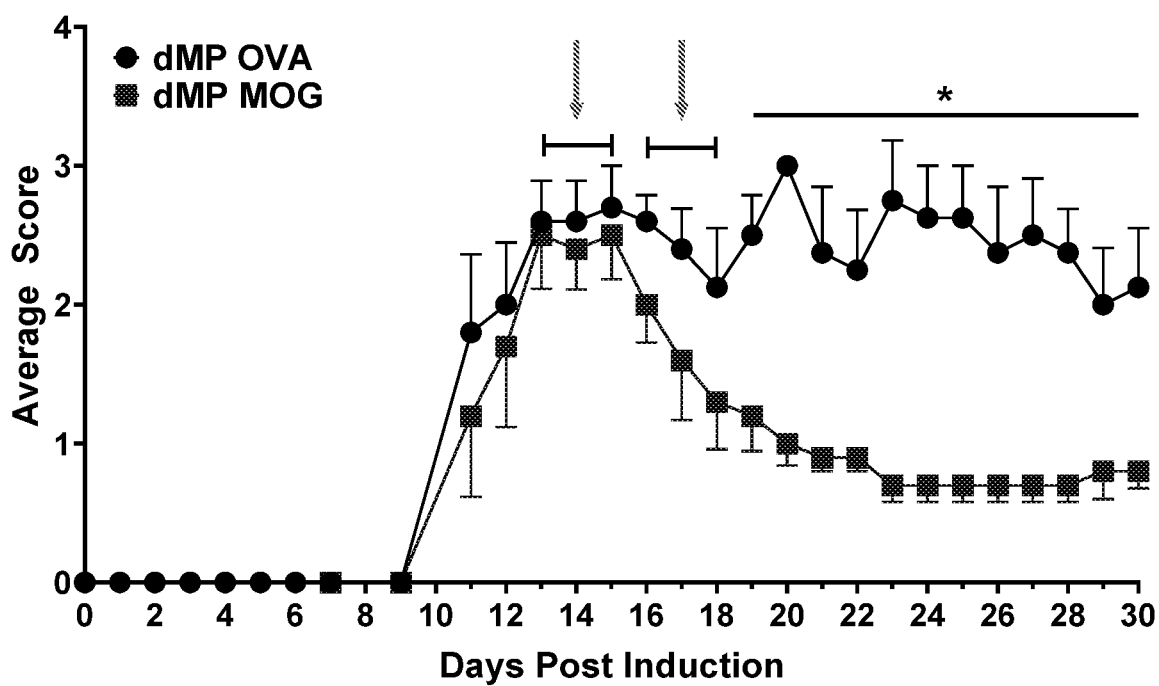
FIG. 13 shows that dMP MOG$_{35-55}$ treatment at the peak of disease majorly reduced the scores and improves mobility of EAE mice. EAE disease score (mean±SEM) of B6 mice treated with dMP MOG$_{35-55}$ (blue square) or dMP OVA$_{323-339}$ (black circle). Mice were induced with EAE and treated with two doses of dMP MOG$_{35-55}$ or dMP OVA$_{323-339}$, first when they reached a score of 3 (peak) (first dose) and after 3 additional days (second dose). The range of days is due to rolling admission. n=5-7 per group. * denotes p<0.05 using Mann-Whitney U Test. Clinical scoring: score 1: flaccid tail, score 2: weak hind limbs, score 3: hind limb paralysis, score 4: quadriplegia.

Example 17: MOG-Specific Dual Microparticle System (dMP-MOG$_{35-55}$) Reverses the Disease and Improves the Mobility of the EAE Mice when Administered at the Peak of Disease and Halts the Disease when Initiated at the EAE Onset dMP-MOG$_{35-55}$ therapy was tested at the onset of disease (score 1, limp tail) and at the peak of disease (score 3, hind limp paralysis). Results show that treatment with dMP MOG$_{35-55}$ at the onset, halted disease progression, as mice remained at a score of 1, while mice treated dMP OVA$_{323-339}$ showed EAE scores continuing to rise (FIG. 12). The efficiency of dMP-MOG$_{35-55}$ therapy was also tested at the peak disease (score 3) and found that scores dropped from 3 (hind limb paralysis to a score of 1 (limp tail) in dMP MOG$_{35-55}$ treated mice, while dMP OVA$_{323-339}$ treated mice remained at a score of 3 (FIG. 13). Thus the dMP MOG$_{35-55}$ system has not only the ability to halt EAE progression in an antigen specific manner, when administered at the onset, but even reverse the disease and significantly improve the mobility of the mice induced with EAE.

REFERENCES

[1] A. Compston, A. Coles, Multiple sclerosis, Lancet 372 (9648) (2008) 1502e1517.
[2] G. Kobelt, J. Berg, D. Atherly, O. Hadjimichael, Costs and quality of life in multiple sclerosis: a cross-sectional study in the United States, Neurology 66 (11) (2006) 1696e1702.
[3] F. D. Lublin, S. C. Reingold, J. A. Cohen, G. R. Cutter, P. S. Ssrensen, A. J. Thompson, J. S. Wolinsky, L. J. Balcer, B. Banwell, F. Barkhof, B. Bebo, P. A. Calabresi, M. Clanet, G. Comi, R. J. Fox, M. S. Freedman, A. D. Goodman, M. Inglese, L. Kappos, B. C. Kieseier, J. A. Lincoln, C. Lubetzki, A. E. Miller, X. Montalban, P. W. O'Connor, J. Petkau, C. Pozzilli, R. A. Rudick, M. P. Sormani, O. Stuve, E. Waubant, C. H. Polman, Defining the clinical course of multiple sclerosis: the 2013 revisions, Neurology 83 (3) (2014) 278e286.
[4] C. A. Dendrou, L. Fugger, M. A. Friese, Immunopathology of multiple sclerosis, Nat. Rev. Immunol. 15 (9) (2015) 545e558.
[5] A. Nylander, D. A. Hafler, Multiple sclerosis, J. Clin. Invest 122 (4) (2012) 1180e1188.
[6] H. L. Weiner, Multiple sclerosis is an inflammatory T-cell-mediated autoimmune disease, Arch. Neurol. 61 (10) (2004) 1613e1615.
[7] B. Bielekova, M. H. Sung, N. Kadom, R. Simon, H. McFarland, R. Martin, Expansion and functional relevance of high-avidity myelin-specific CD4 T cells in multiple sclerosis, J. Immunol. 172(6) (2004) 3893e3904.
[8] N. Hellings, M. Bare'e, C. Verhoeven, M. B. D'hooghe, R. Medaer, C. C. Bernard, J. Raus, P. Stinissen, T-cell reactivity to multiple myelin antigens in multiple sclerosis patients and healthy controls, J. Neurosci. Res. 63(3) (2001) 290e302.
[9] E. Lavi, C. S. Constantinescu, Experimental Models of Multiple Sclerosis, Springer, New York, 2005.
[10] C. L. Langrish, Y. Chen, W. M. Blumenschein, J. Mattson, B. Basham, J. D. Sedgwick, T. McClanahan, R. A. Kastelein, D. J. Cua, IL-23 drives a pathogenic T cell population that induces autoimmune inflammation, J. Exp. Med. 201(2) (2005) 233e240.
[11] H. Park, Z. Li, X. O. Yang, S. H. Chang, R. Nurieva, Y. H. Wang, Y. Wang, L. Hood, Z. Zhu, Q. Tian, C. Dong, A distinct lineage of CD4 T cells regulates tissue inflammation by producing interleukin 17, Nat. Immunol. 6(11) (2005) 1133e1141.
[12] I. I. Ivanov, B. S. McKenzie, L. Zhou, C. E. Tadokoro, A. Lepelley, J. J. Lafaille, D. J. Cua, D. R. Littman, The orphan nuclear receptor RORgammat directs the differentiation program of proinflammatory IL-17 T helper cells, Cell 126(6) (2006) 1121e1133.
[13] L. Codarri, G. Gyulve'szi, V. Tosevski, L. Hesske, A. Fontana, L. Magnenat, T. Suter, B. Becher, RORgt drives production of the cytokine GM-CSF in helper T cells, which is essential for the effector phase of autoimmune neuro-inflammation, Nat. Immunol. 12(6) (2011) 560e567.
[14] M. El-Behi, B. Ciric, H. Dai, Y. Yan, M. Cullimore, F. Safavi, G. X. Zhang, B. N. Dittel, A. Rostami, The encephalitogenicity of T(H)17 cells is dependent on IL-1- and IL-23-induced production of the cytokine GM-CSF, Nat. Immunol. 12(6) (2011) 568e575.

[15] E. Bettelli, B. Sullivan, S. J. Szabo, R. A. Sobel, L. H. Glimcher, V. K. Kuchroo, Loss of T-bet, but not STAT1, prevents the development of experimental autoimmune encephalomyelitis, J. Exp. Med. 200 (1) (2004) 79e87.

[16] D. M. Wingerchuk, J. L. Carter, Multiple sclerosis: current and emerging disease-modifying therapies and treatment strategies, Mayo Clin. Proc. 89(2) (2014) 225e240.

[17] D. S. Goodin, E. M. Frohman, G. P. Garmany, J. Halper, W. H. Likosky, F. D. Lublin, D. H. Silberberg, W. H. Stuart, S. van den Noort, T.a.T.A.S.o.t.A.A-.o.N.a.t.M.C.f.C.P. Guidelines, disease modifying therapies in multiple sclerosis: report of the therapeutics and technology assessment subcommittee of the american academy of neurology and the MS council for clinical practice guidelines, Neurology 58(2) (2002) 169e178.

[18] Z. Hunter, D. P. McCarthy, W. T. Yap, C. T. Harp, D. R. Getts, L. D. Shea, S. D. Miller, A biodegradable nanoparticle platform for the induction of antigen-specific immune tolerance for treatment of autoimmune disease, ACS nano 8(3) (2014) 2148e2160.

[19] A. Yeste, M. Nadeau, E. J. Burns, H. L. Weiner, F. J. Quintana, Nanoparticle-mediated codelivery of myelin antigen and a tolerogenic small molecule suppresses experimental autoimmune encephalomyelitis, Proc. Natl. Acad. Sci. U.S.A. 109(28) (2012) 11270e11275.

[20] D. S. Goodin, B. A. Cohen, P. O'Connor, L. Kappos, J. C. Stevens, T.a.T.A.S.o.t.A.A.o. Neurology, Assessment: the use of natalizumab (Tysabri) for the treatment of multiple sclerosis (an evidence-based review): report of the Therapeutics and Technology Assessment Subcommittee of the American Academy of Neurology, Neurology 71(10) (2008) 766e773.

[21] R. Amon, R. Aharoni, Mechanism of action of glatiramer acetate in multiple sclerosis and its potential for the development of new applications, Proc. Natl. Acad. Sci. U.S.A. 101 (Suppl 2) (2004) 14593e14598.

[22] R. J. Fox, D. H. Miller, J. T. Phillips, M. Hutchinson, E. Havrdova, M. Kita, M. Yang, K. Raghupathi, M. Novas, M. T. Sweetser, V. Viglietta, K. T. Dawson, C. S. Investigators, Placebo-controlled phase 3 study of oral BG-12 or glatir-amer in multiple sclerosis, N. Engl. J. Med. 367(12) (2012) 1087e1097.

[23] J. A. Cohen, J. Chun, Mechanisms of fingolimod's efficacy and adverse effects in multiple sclerosis, Ann. Neurol. 69(5) (2011) 759e777.

[24] A. Brickshawana et al. Investigation of the KIR4.1 potassium channel as a putative antigen in patients with multiple sclerosis: a comparative study. Lancet Neurol. 13, 795-806 (2014).

[25] C. Riedhammer, R Weissert, Antigen presentation, autoantigens, and immune regulation in multiple sclerosis and other autoimmune diseases, Front Immunol, 6: 322 (2015).

[26] P. A. Pino, A. E. Cardona, Isolation of brain and spinal cord mononuclear cells using percoll gradients, J. Vis. Exp. (48) (2011).

[27] D. Califano, K. J. Sweeney, H. Le, J. VanValkenburgh, E. Yager, W. O'Connor, J. S. Kennedy, D. M. Jones, D. Avram, Diverting T helper cell trafficking through increased plasticity attenuates autoimmune encephalomyelitis, J. Clin. Invest 124(1) (2014) 174e187.

[28] J. Vanvalkenburgh, D. I. Albu, C. Bapanpally, S. Casanova, D. Califano, D. M. Jones, L. Ignatowicz, S. Kawamoto, S. Fagarasan, N. A. Jenkins, N. G. Copeland, P. Liu, D. Avram, Critical role of Bcl11b in suppressor function of T regulatory cells and prevention of inflammatory bowel disease, J. Exp. Med. 208(10) (2011) 2069e2081.

[29] N. Mayuzumi, H. Matsushima, A. Takashima, IL-33 promotes DC development in BM culture by triggering GM-CSF production, Eur. J. Immunol. 39(12) (2009) 3331e3342.

[30] D. Califano, J. J. Cho, M. N. Uddin, K. J. Lorentsen, Q. Yang, A. Bhandoola, H. Li, D. Avram, Transcription factor Bcl11b controls identity and function of mature type 2 innate lymphoid cells, Immunity 43 (2) (2015) 354e368.

[31] J. S. Lewis, N. V. Dolgova, Y. Zhang, C. Q. Xia, C. H. Wasserfall, M. A. Atkinson, M. J. Clare-Salzler, B. G. Keselowsky, A combination dual-sized microparticle system modulates dendritic cells and prevents type 1 diabetes in prediabetic NOD mice, Clin. Immunol. 160(1) (2015) 90e102.

[32] A. Jaeger, V. Dardalhon, R. A. Sobel, E. Bettelli, V. K. Kuchroo, Th1, Th17, and Th9 effector cells induce experimental autoimmune encephalomyelitis with different pathological phenotypes, J. Immunol. 183(11) (2009) 7169e7177.

[33] K. Hirota, J. H. Duarte, M. Veldhoen, E. Hornsby, Y. Li, D. J. Cua, H. Ahlfors, C. Wilhelm, M. Tolaini, U. Menzel, A. Garefalaki, A. J. Potocnik, B. Stockinger, Fate mapping of IL-17-producing T cells in inflammatory responses, Nat. Immunol. 12(3) (2011) 255e263.

[34] Y. Yang, J. Weiner, Y. Liu, A. J. Smith, D. J. Huss, R. Winger, H. Peng, P. D. Cravens, M. K. Racke, A. E. Lovett-Racke, T-bet is essential for encephalitogenicity of both Th1 and Th17 cells, J. Exp. Med. 206(7) (2009) 1549e1564.

[35] Y. Lee, A. Awasthi, N. Yosef, F. J. *Quintana*, S. Xiao, A. Peters, C. Wu, M. Kleinewietfeld, S. Kunder, D. A. Hafler, R. A. Sobel, A. Regev, V. K. Kuchroo, Induction and molecular signature of pathogenic TH17 cells, Nat. Immunol. 13(10) (2012) 991e999

[36] L. Codarri, M. Greter, B. Becher, Communication between pathogenic T cells and myeloid cells in neuroinflammatory disease, Trends Immunol. 34(3) (2013) 114e119.

[37] Y. Xiao, J. Jin, M. Chang, J. H. Chang, H. Hu, X. Zhou, G. C. Brittain, C. Stansberg, Ø. Torkildsen, X. Wang, R. Brink, X. Cheng, S. C. Sun, Peli1 promotes microglia-mediated CNS inflammation by regulating Traf3 degradation, Nat. Med. 19(5) (2013) 595e602.

[38] D. M. Mosser, J. P. Edwards, Exploring the full spectrum of macrophage activation, Nat. Rev. Immunol. 8(12) (2008) 958e969.

What is claimed is:

1. A dual microparticle system for targeting an antigen-presenting immune cell in a subject who is suspected of having, at risk of having or has Multiple Sclerosis, wherein the microparticle system is a composition that comprises: microparticles that are phagocytosable by the antigen-presenting immune cell, and microparticles that are non-phagocytosable by the antigen-presenting immune cell; wherein the phagocytosable microparticles together comprise at least one myelin antigen, the at least one myelin antigen being an antigen involved in pathogenesis of multiple sclerosis, and at least one immunomodulatory agent selected from vitamin D3, vitamin D3 analog, glucocorticoid, estrogen, rapamycin, and retinoic acid; and wherein the non-phagocytosable microparticles comprise at least one immunosuppressive tolerogenic agent selected from IL-10, TGF-p, and nonsteroidal anti-inflammatory drugs (NSAIDs), an agent that recruits the antigen-presenting immune cell of interest selected from GM-CSF, G-CFS, M-CSF, CCL19, CCL20, CCL21, and VEGF-C, wherein the microparticle system further comprises a remyelinating agent selected from clemastine, clobetasol, digoxin, miconazole, phenytoin, and quetiapine.

2. The microparticle system of claim 1, wherein the remyelinating agent is administered in soluble form by intravenous injection or is incorporated into the non-phagocytosable microparticles.

3. The microparticle system of claim 1, wherein the phagocytosable microparticle has a diameter of 0.2 µm-5.0 µm and the non-phagocytosable microparticle has a diameter of 15.0 µm-50.0 µm.

4. The microparticle system of claim 1, wherein the phagocytosable microparticle or non-phagocytosable microparticle are fabricated from poly(lactic-co-glycolic acid) (PLGA).

5. The microparticle system of claim 1, wherein the at least one myelin antigen comprises at least one of SEQ ID NOs 1-25 or a contiguous fragment thereof.

6. The microparticle system of claim 5, wherein the at least one myelin-antigen comprises at least one of SEQ ID NOs 12-25 or a fragment thereof comprising contiguous amino acids of said SEQ ID NOs.

7. The microparticle system of claim 6, wherein at least one myelin-antigen comprises SEQ ID NO. 23.

8. The microparticle system of claim 1, wherein the composition is in a liquid formulation further comprising a pharmaceutically acceptable carrier.

9. The microparticle system of claim 1, wherein the phagocytosable MPs comprise the amino acid sequence of SEQ ID NO. 23 and vitamin D3.

10. The microparticle system of claim 1, wherein the non-phagocytosable MPs comprise TGF-β1 and GM-CSF.

11. A method of treating a subject who is suspected of having, at risk of having or has MS comprising administering a therapeutically effective amount of a composition of claim 1.

12. The method, according to claim 11, wherein the ratio of the at least one myelin antigen to the at least one immunomodulatory agent is between 1:20 and 1:1.

13. A method of treating a subject who is suspected of having, at risk of having or has MS comprising administering a therapeutically effective amount of a first composition that comprises microparticles that are phagocytosable by the antigen-presenting immune cell, and a second composition comprising microparticles that are non-phagocytosable by the antigen-presenting immune cell; wherein the phagocytosable microparticles together comprise at least one myelin antigen, the at least one myelin antigen being an antigen involved in pathogenesis of multiple sclerosis and at least one immunomodulatory agent selected from vitamin D3, vitamin D3 analog, glucocorticoid, estrogen, rapamycin, and retinoic acid; wherein the non-phagocytosable microparticles comprise at least one immunosuppressive tolerogenic agent selected from IL-10, TGF-p, and nonsteroidal anti-inflammatory drugs (NSAIDs), an agent that recruits the antigen-presenting immune cell of interest selected from GM-CSF, G-CFS, M-CSF, CCL19, CCL20, CCL21, and VEGF-C; wherein and wherein the first composition and second composition are admixed prior administration or are administered separately.

14. The method of claim 13, wherein the first composition and second composition are administered separately.

15. The method of claim 14, wherein the first composition and second composition are administered by the same or different modes of administration.

16. The method of claim 15, wherein the modes of administration comprise subcutaneous, intradermal, intramuscular, or intravenous administration.

* * * * *

SEQUENCE LISTING

<160> NUMBER OF SEQ ID NOS: 26

<210> SEQ ID NO 1
<211> LENGTH: 203
<212> TYPE: PRT

<213> ORGANISM: Homo sapiens

<400> SEQUENCE: 1

```
Met Ala Ser Leu Ser Arg Pro Ser Leu Pro Ser Cys Leu Cys Ser Phe
1               5                   10                  15

Leu Leu Leu Leu Leu Gln Val Ser Ser Tyr Ala Gly Gln Phe
            20                  25                  30

Arg Val Ile Gly Pro Arg His Pro Ile Arg Ala Leu Val Gly Asp Glu
            35                  40                  45

Val Glu Leu Pro Cys Arg Ile Ser Pro Gly Lys Asn Ala Thr Gly Met
50                  55                  60

Glu Val Gly Trp Tyr Arg Pro Pro Phe Ser Arg Val Val His Leu Tyr
65                  70                  75                  80

Arg Asn Gly Lys Asp Gln Asp Gly Asp Gln Ala Pro Glu Tyr Arg Gly
                85                  90                  95

Arg Thr Glu Leu Leu Lys Asp Ala Ile Gly Glu Gly Lys Val Thr Leu
                100                 105                 110

Arg Ile Arg Asn Val Arg Phe Ser Asp Glu Gly Gly Phe Thr Cys Phe
                115                 120                 125

Phe Arg Asp His Ser Tyr Gln Glu Ala Ala Met Glu Leu Lys Val
                130                 135                 140

Glu Asp Pro Phe Tyr Trp Val Ser Pro Gly Val Leu Val Leu Leu Ala
145                 150                 155                 160

Val Leu Pro Val Leu Leu Leu Gln Ile Thr Val Gly Leu Val Phe Leu
                165                 170                 175

Cys Leu Gln Tyr Arg Leu Arg Glu Ser Phe Gly Val Leu Gly Pro Gln
                180                 185                 190

Val Lys Glu Pro Lys Lys Thr Gly Asn Pro Phe
                195                 200
```

<210> SEQ ID NO 2
<211> LENGTH: 197
<212> TYPE: PRT
<213> ORGANISM: Homo sapiens

<400> SEQUENCE: 2

```
Met Ala Ser Gln Lys Arg Pro Ser Gln Arg His Gly Ser Lys Tyr Leu
1               5                   10                  15

Ala Thr Ala Ser Thr Met Asp His Ala Arg His Gly Phe Leu Pro Arg
            20                  25                  30

His Arg Asp Thr Gly Ile Leu Asp Ser Ile Gly Arg Phe Phe Gly Gly
            35                  40                  45

Asp Arg Gly Ala Pro Lys Arg Gly Ser Gly Lys Val Pro Trp Leu Lys
50                  55                  60

Pro Gly Arg Ser Pro Leu Pro Ser His Ala Arg Ser Gln Pro Gly Leu
65                  70                  75                  80

Cys Asn Met Tyr Lys Asp Ser His His Pro Ala Arg Thr Ala His Tyr
                85                  90                  95

Gly Ser Leu Pro Gln Lys Ser His Gly Arg Thr Gln Asp Glu Asn Pro
                100                 105                 110

Val Val His Phe Phe Lys Asn Ile Val Thr Pro Arg Thr Pro Pro Pro
                115                 120                 125

Ser Gln Gly Lys Gly Arg Gly Leu Ser Leu Ser Arg Phe Ser Trp Gly
                130                 135                 140

Ala Glu Gly Gln Arg Pro Gly Phe Gly Tyr Gly Gly Arg Ala Ser Asp
```

```
                145                 150                 155                 160
Tyr Lys Ser Ala His Lys Gly Phe Lys Gly Val Asp Ala Gln Gly Thr
                    165                 170                 175

Leu Ser Lys Ile Phe Lys Leu Gly Gly Arg Asp Ser Arg Ser Gly Ser
                180                 185                 190

Pro Met Ala Arg Arg
            195

<210> SEQ ID NO 3
<211> LENGTH: 277
<212> TYPE: PRT
<213> ORGANISM: Homo sapiens

<400> SEQUENCE: 3

Met Gly Leu Leu Glu Cys Cys Ala Arg Cys Leu Val Gly Ala Pro Phe
1               5                   10                  15

Ala Ser Leu Val Ala Thr Gly Leu Cys Phe Phe Gly Val Ala Leu Phe
                20                  25                  30

Cys Gly Cys Gly His Glu Ala Leu Thr Gly Thr Glu Lys Leu Ile Glu
            35                  40                  45

Thr Tyr Phe Ser Lys Asn Tyr Gln Asp Tyr Glu Tyr Leu Ile Asn Val
50                  55                  60

Ile His Ala Phe Gln Tyr Val Ile Tyr Gly Thr Ala Ser Phe Phe Phe
65                  70                  75                  80

Leu Tyr Gly Ala Leu Leu Leu Ala Glu Gly Phe Tyr Thr Thr Gly Ala
                85                  90                  95

Val Arg Gln Ile Phe Gly Asp Tyr Lys Thr Thr Ile Cys Gly Lys Gly
                100                 105                 110

Leu Ser Ala Thr Val Thr Gly Gly Gln Lys Gly Arg Gly Ser Arg Gly
            115                 120                 125

Gln His Gln Ala His Ser Leu Glu Arg Val Cys His Cys Leu Gly Lys
130                 135                 140

Trp Leu Gly His Pro Asp Lys Phe Val Gly Ile Thr Tyr Ala Leu Thr
145                 150                 155                 160

Val Val Trp Leu Leu Val Phe Ala Cys Ser Ala Val Pro Val Tyr Ile
                165                 170                 175

Tyr Phe Asn Thr Trp Thr Thr Cys Gln Ser Ile Ala Phe Pro Ser Lys
            180                 185                 190

Thr Ser Ala Ser Ile Gly Ser Leu Cys Ala Asp Ala Arg Met Tyr Gly
            195                 200                 205

Val Leu Pro Trp Asn Ala Phe Pro Gly Lys Val Cys Gly Ser Asn Leu
210                 215                 220

Leu Ser Ile Cys Lys Thr Ala Glu Phe Gln Met Thr Phe His Leu Phe
225                 230                 235                 240

Ile Ala Ala Phe Val Gly Ala Ala Ala Thr Leu Val Ser Leu Leu Thr
                245                 250                 255

Phe Met Ile Ala Ala Thr Tyr Asn Phe Ala Val Leu Lys Leu Met Gly
            260                 265                 270

Arg Gly Thr Lys Phe
        275

<210> SEQ ID NO 4
<211> LENGTH: 421
<212> TYPE: PRT
<213> ORGANISM: Homo sapiens
```

```
<400> SEQUENCE: 4

Met Asn Arg Gly Phe Ser Arg Lys Ser His Thr Phe Leu Pro Lys Ile
1               5                   10                  15

Phe Phe Arg Lys Met Ser Ser Gly Ala Lys Asp Lys Pro Glu Leu
            20                  25                  30

Gln Phe Pro Phe Leu Gln Asp Glu Asp Thr Val Ala Thr Leu Leu Glu
            35                  40                  45

Cys Lys Thr Leu Phe Ile Leu Arg Gly Leu Pro Gly Ser Gly Lys Ser
        50                  55                  60

Thr Leu Ala Arg Val Ile Val Asp Lys Tyr Arg Asp Gly Thr Lys Met
65                  70                  75                  80

Val Ser Ala Asp Ala Tyr Lys Ile Thr Pro Gly Ala Arg Gly Ala Phe
                85                  90                  95

Ser Glu Glu Tyr Lys Arg Leu Asp Glu Asp Leu Ala Ala Tyr Cys Arg
            100                 105                 110

Arg Arg Asp Ile Arg Ile Leu Val Leu Asp Asp Thr Asn His Glu Arg
        115                 120                 125

Glu Arg Leu Glu Gln Leu Phe Glu Met Ala Asp Gln Tyr Gln Tyr Gln
    130                 135                 140

Val Val Leu Val Glu Pro Lys Thr Ala Trp Arg Leu Asp Cys Ala Gln
145                 150                 155                 160

Leu Lys Glu Lys Asn Gln Trp Gln Leu Ser Ala Asp Asp Leu Lys Lys
                165                 170                 175

Leu Lys Pro Gly Leu Glu Lys Asp Phe Leu Pro Leu Tyr Phe Gly Trp
            180                 185                 190

Phe Leu Thr Lys Lys Ser Ser Glu Thr Leu Arg Lys Ala Gly Gln Val
        195                 200                 205

Phe Leu Glu Glu Leu Gly Asn His Lys Ala Phe Lys Lys Glu Leu Arg
    210                 215                 220

Gln Phe Val Pro Gly Asp Glu Pro Arg Glu Lys Met Asp Leu Val Thr
225                 230                 235                 240

Tyr Phe Gly Lys Arg Pro Pro Gly Val Leu His Cys Thr Thr Lys Phe
                245                 250                 255

Cys Asp Tyr Gly Lys Ala Pro Gly Ala Glu Glu Tyr Ala Gln Gln Asp
            260                 265                 270

Val Leu Lys Lys Ser Tyr Ser Lys Ala Phe Thr Leu Thr Ile Ser Ala
        275                 280                 285

Leu Phe Val Thr Pro Lys Thr Thr Gly Ala Arg Val Glu Leu Ser Glu
    290                 295                 300

Gln Gln Leu Gln Leu Trp Pro Ser Asp Val Asp Lys Leu Ser Pro Thr
305                 310                 315                 320

Asp Asn Leu Pro Arg Gly Ser Arg Ala His Ile Thr Leu Gly Cys Ala
                325                 330                 335

Ala Asp Val Glu Ala Val Gln Thr Gly Leu Asp Leu Leu Glu Ile Leu
            340                 345                 350

Arg Gln Glu Lys Gly Gly Ser Arg Gly Glu Val Gly Glu Leu Ser
        355                 360                 365

Arg Gly Lys Leu Tyr Ser Leu Gly Asn Gly Arg Trp Met Leu Thr Leu
    370                 375                 380

Ala Lys Asn Met Glu Val Arg Ala Ile Phe Thr Gly Tyr Tyr Gly Lys
385                 390                 395                 400

Gly Lys Pro Val Pro Thr Gln Gly Ser Arg Lys Gly Gly Ala Leu Gln
                405                 410                 415
```

Ser Cys Thr Ile Ile
            420

<210> SEQ ID NO 5
<211> LENGTH: 626
<212> TYPE: PRT
<213> ORGANISM: Homo sapiens

<400> SEQUENCE: 5

Met Ile Phe Leu Thr Ala Leu Pro Leu Phe Trp Ile Met Ile Ser Ala
1               5                   10                  15

Ser Arg Gly Gly His Trp Gly Ala Trp Met Pro Ser Ser Ile Ser Ala
            20                  25                  30

Phe Glu Gly Thr Cys Val Ser Ile Pro Cys Arg Phe Asp Phe Pro Asp
        35                  40                  45

Glu Leu Arg Pro Ala Val Val His Gly Val Trp Tyr Phe Asn Ser Pro
    50                  55                  60

Tyr Pro Lys Asn Tyr Pro Pro Val Val Phe Lys Ser Arg Thr Gln Val
65                  70                  75                  80

Val His Glu Ser Phe Gln Gly Arg Ser Arg Leu Leu Gly Asp Leu Gly
                85                  90                  95

Leu Arg Asn Cys Thr Leu Leu Leu Ser Asn Val Ser Pro Glu Leu Gly
            100                 105                 110

Gly Lys Tyr Tyr Phe Arg Gly Asp Leu Gly Gly Tyr Asn Gln Tyr Thr
        115                 120                 125

Phe Ser Glu His Ser Val Leu Asp Ile Val Asn Thr Pro Asn Ile Val
    130                 135                 140

Val Pro Pro Glu Val Val Ala Gly Thr Glu Val Glu Val Ser Cys Met
145                 150                 155                 160

Val Pro Asp Asn Cys Pro Glu Leu Arg Pro Glu Leu Ser Trp Leu Gly
                165                 170                 175

His Glu Gly Leu Gly Glu Pro Ala Val Leu Gly Arg Leu Arg Glu Asp
            180                 185                 190

Glu Gly Thr Trp Val Gln Val Ser Leu Leu His Phe Val Pro Thr Arg
        195                 200                 205

Glu Ala Asn Gly His Arg Leu Gly Cys Gln Ala Ser Phe Pro Asn Thr
    210                 215                 220

Thr Leu Gln Phe Glu Gly Tyr Ala Ser Met Asp Val Lys Tyr Pro Pro
225                 230                 235                 240

Val Ile Val Glu Met Asn Ser Ser Val Glu Ala Ile Glu Gly Ser His
                245                 250                 255

Val Ser Leu Leu Cys Gly Ala Asp Ser Asn Pro Pro Pro Leu Leu Thr
            260                 265                 270

Trp Met Arg Asp Gly Thr Val Leu Arg Glu Ala Val Ala Glu Ser Leu
        275                 280                 285

Leu Leu Glu Leu Glu Glu Val Thr Pro Ala Glu Asp Gly Val Tyr Ala
    290                 295                 300

Cys Leu Ala Glu Asn Ala Tyr Gly Gln Asp Asn Arg Thr Val Gly Leu
305                 310                 315                 320

Ser Val Met Tyr Ala Pro Trp Lys Pro Thr Val Asn Gly Thr Met Val
                325                 330                 335

Ala Val Glu Gly Glu Thr Val Ser Ile Leu Cys Ser Thr Gln Ser Asn
            340                 345                 350

Pro Asp Pro Ile Leu Thr Ile Phe Lys Glu Lys Gln Ile Leu Ser Thr

```
               355                 360                 365
Val Ile Tyr Glu Ser Glu Leu Gln Leu Glu Leu Pro Ala Val Ser Pro
        370                 375                 380

Glu Asp Asp Gly Glu Tyr Trp Cys Val Ala Glu Asn Gln Tyr Gly Gln
385                 390                 395                 400

Arg Ala Thr Ala Phe Asn Leu Ser Val Glu Phe Ala Pro Val Leu Leu
                405                 410                 415

Leu Glu Ser His Cys Ala Ala Arg Asp Thr Val Gln Cys Leu Cys
            420                 425                 430

Val Val Lys Ser Asn Pro Glu Pro Ser Val Ala Phe Glu Leu Pro Ser
        435                 440                 445

Arg Asn Val Thr Val Asn Glu Ser Glu Arg Glu Phe Val Tyr Ser Glu
450                 455                 460

Arg Ser Gly Leu Val Leu Thr Ser Ile Leu Thr Leu Arg Gly Gln Ala
465                 470                 475                 480

Gln Ala Pro Pro Arg Val Ile Cys Thr Ala Arg Asn Leu Tyr Gly Ala
                485                 490                 495

Lys Ser Leu Glu Leu Pro Phe Gln Gly Ala His Arg Leu Met Trp Ala
            500                 505                 510

Lys Ile Gly Pro Val Gly Ala Val Ala Phe Ala Ile Leu Ile Ala
        515                 520                 525

Ile Val Cys Tyr Ile Thr Gln Thr Arg Arg Lys Asn Val Thr Glu
    530                 535                 540

Ser Pro Ser Phe Ser Ala Gly Asp Asn Pro Pro Val Leu Phe Ser Ser
545                 550                 555                 560

Asp Phe Arg Ile Ser Gly Ala Pro Glu Lys Tyr Glu Ser Glu Arg Arg
                565                 570                 575

Leu Gly Ser Glu Arg Arg Leu Leu Gly Leu Arg Gly Glu Pro Pro Glu
            580                 585                 590

Leu Asp Leu Ser Tyr Ser His Ser Asp Leu Gly Lys Arg Pro Thr Lys
        595                 600                 605

Asp Ser Tyr Thr Leu Thr Glu Glu Leu Ala Glu Tyr Ala Glu Ile Arg
    610                 615                 620

Val Lys
625

<210> SEQ ID NO 6
<211> LENGTH: 183
<212> TYPE: PRT
<213> ORGANISM: Homo sapiens

<400> SEQUENCE: 6

Met Ser Gln Lys Pro Ala Lys Glu Gly Pro Arg Leu Ser Lys Asn Gln
1               5                   10                  15

Lys Tyr Ser Glu His Phe Ser Ile His Cys Cys Pro Pro Phe Thr Phe
            20                  25                  30

Leu Asn Ser Lys Glu Ile Val Asp Arg Lys Tyr Ser Ile Cys Lys
        35                  40                  45

Ser Gly Cys Phe Tyr Gln Lys Lys Glu Glu Asp Trp Ile Cys Cys Ala
    50                  55                  60

Cys Gln Lys Thr Arg Thr Ser Arg Arg Ala Lys Ser Pro Gln Arg Pro
65                  70                  75                  80

Lys Gln Gln Pro Ala Ala Pro Pro Ala Val Val Arg Ala Pro Ala Lys
                85                  90                  95
```

```
Pro Arg Ser Pro Pro Arg Ser Glu Arg Gln Pro Arg Ser Pro Pro Arg
            100                 105                 110

Ser Glu Arg Gln Pro Arg Ser Pro Pro Arg Ser Glu Arg Gln Pro Arg
        115                 120                 125

Ser Pro Pro Arg Ser Glu Arg Gln Pro Arg Pro Arg Pro Glu Val Arg
    130                 135                 140

Pro Pro Pro Ala Lys Gln Arg Pro Pro Gln Lys Ser Lys Gln Gln Pro
145                 150                 155                 160

Arg Ser Ser Pro Leu Arg Gly Pro Gly Ala Ser Arg Gly Gly Ser Pro
                165                 170                 175

Val Lys Ala Ser Arg Phe Trp
            180
```

<210> SEQ ID NO 7
<211> LENGTH: 92
<212> TYPE: PRT
<213> ORGANISM: Homo sapiens

<400> SEQUENCE: 7

```
Met Ser Glu Leu Glu Lys Ala Met Val Ala Leu Ile Asp Val Phe His
1               5                   10                  15

Gln Tyr Ser Gly Arg Glu Gly Asp Lys His Lys Leu Lys Lys Ser Glu
            20                  25                  30

Leu Lys Glu Leu Ile Asn Asn Glu Leu Ser His Phe Leu Glu Glu Ile
        35                  40                  45

Lys Glu Gln Glu Val Val Asp Lys Val Met Glu Thr Leu Asp Asn Asp
    50                  55                  60

Gly Asp Gly Glu Cys Asp Phe Gln Glu Phe Met Ala Phe Val Ala Met
65                  70                  75                  80

Val Thr Thr Ala Cys His Glu Phe Phe Glu His Glu
            85                  90
```

<210> SEQ ID NO 8
<211> LENGTH: 337
<212> TYPE: PRT
<213> ORGANISM: Homo sapiens

<400> SEQUENCE: 8

```
Met Ser Ser Ser Pro Val Lys Arg Gln Arg Met Glu Ser Ala Leu Asp
1               5                   10                  15

Gln Leu Lys Gln Phe Thr Thr Val Val Ala Asp Thr Gly Asp Phe His
            20                  25                  30

Ala Ile Asp Glu Tyr Lys Pro Gln Asp Ala Thr Thr Asn Pro Ser Leu
        35                  40                  45

Ile Leu Ala Ala Ala Gln Met Pro Ala Tyr Gln Glu Leu Val Glu Glu
    50                  55                  60

Ala Ile Ala Tyr Gly Arg Lys Leu Gly Gly Ser Gln Glu Asp Gln Ile
65                  70                  75                  80

Lys Asn Ala Ile Asp Lys Leu Phe Val Leu Phe Gly Ala Glu Ile Leu
            85                  90                  95

Lys Lys Ile Pro Gly Arg Val Ser Thr Glu Val Asp Ala Arg Leu Ser
            100                 105                 110

Phe Asp Lys Asp Ala Met Val Ala Arg Ala Arg Arg Leu Ile Glu Leu
        115                 120                 125

Tyr Lys Glu Ala Gly Ile Ser Lys Asp Arg Ile Leu Ile Lys Leu Ser
    130                 135                 140
```

-continued

Ser Thr Trp Glu Gly Ile Gln Ala Gly Lys Glu Leu Glu Glu Gln His
145                 150                 155                 160

Gly Ile His Cys Asn Met Thr Leu Leu Phe Ser Phe Ala Gln Ala Val
                165                 170                 175

Ala Cys Ala Glu Ala Gly Val Thr Leu Ile Ser Pro Phe Val Gly Arg
            180                 185                 190

Ile Leu Asp Trp His Val Ala Asn Thr Asp Lys Lys Ser Tyr Glu Pro
        195                 200                 205

Leu Glu Asp Pro Gly Val Lys Ser Val Thr Lys Ile Tyr Asn Tyr Tyr
    210                 215                 220

Lys Lys Phe Ser Tyr Lys Thr Ile Val Met Gly Ala Ser Phe Arg Asn
225                 230                 235                 240

Thr Gly Glu Ile Lys Ala Leu Ala Gly Cys Asp Phe Leu Thr Ile Ser
                245                 250                 255

Pro Lys Leu Leu Gly Glu Leu Leu Gln Asp Asn Ala Lys Leu Val Pro
            260                 265                 270

Val Leu Ser Ala Lys Ala Ala Gln Ala Ser Asp Leu Glu Lys Ile His
        275                 280                 285

Leu Asp Glu Lys Ser Phe Arg Trp Leu His Asn Glu Asp Gln Met Ala
    290                 295                 300

Val Glu Lys Leu Ser Asp Gly Ile Arg Lys Phe Ala Ala Asp Ala Val
305                 310                 315                 320

Lys Leu Glu Arg Met Leu Thr Glu Arg Met Phe Asn Ala Glu Asn Gly
                325                 330                 335

Lys

<210> SEQ ID NO 9
<211> LENGTH: 1347
<212> TYPE: PRT
<213> ORGANISM: Homo sapiens

<400> SEQUENCE: 9

Met Ala Arg Gln Pro Pro Pro Trp Val His Ala Ala Phe Leu Leu
1                   5                   10                  15

Cys Leu Leu Ser Leu Gly Gly Ala Ile Glu Ile Pro Met Asp Pro Ser
                20                  25                  30

Ile Gln Asn Glu Leu Thr Gln Pro Pro Thr Ile Thr Lys Gln Ser Ala
            35                  40                  45

Lys Asp His Ile Val Asp Pro Arg Asp Asn Ile Leu Ile Glu Cys Glu
        50                  55                  60

Ala Lys Gly Asn Pro Ala Pro Ser Phe His Trp Thr Arg Asn Ser Arg
65                  70                  75                  80

Phe Phe Asn Ile Ala Lys Asp Pro Arg Val Ser Met Arg Arg Arg Ser
                85                  90                  95

Gly Thr Leu Val Ile Asp Phe Arg Ser Gly Gly Arg Pro Glu Glu Tyr
            100                 105                 110

Glu Gly Glu Tyr Gln Cys Phe Ala Arg Asn Lys Phe Gly Thr Ala Leu
        115                 120                 125

Ser Asn Arg Ile Arg Leu Gln Val Ser Lys Ser Pro Leu Trp Pro Lys
    130                 135                 140

Glu Asn Leu Asp Pro Val Val Val Gln Glu Gly Ala Pro Leu Thr Leu
145                 150                 155                 160

Gln Cys Asn Pro Pro Pro Gly Leu Pro Ser Pro Val Ile Phe Trp Met
                165                 170                 175

```
Ser Ser Ser Met Glu Pro Ile Thr Gln Asp Lys Arg Val Ser Gln Gly
            180                 185                 190

His Asn Gly Asp Leu Tyr Phe Ser Asn Val Met Leu Gln Asp Met Gln
        195                 200                 205

Thr Asp Tyr Ser Cys Asn Ala Arg Phe His Phe Thr His Thr Ile Gln
    210                 215                 220

Gln Lys Asn Pro Phe Thr Leu Lys Val Leu Thr Thr Arg Gly Val Ala
225                 230                 235                 240

Glu Arg Thr Pro Ser Phe Met Tyr Pro Gln Gly Thr Ala Ser Ser Gln
                245                 250                 255

Met Val Leu Arg Gly Met Asp Leu Leu Leu Glu Cys Ile Ala Ser Gly
            260                 265                 270

Val Pro Thr Pro Asp Ile Ala Trp Tyr Lys Lys Gly Gly Asp Leu Pro
        275                 280                 285

Ser Asp Lys Ala Lys Phe Glu Asn Phe Asn Lys Ala Leu Arg Ile Thr
    290                 295                 300

Asn Val Ser Glu Glu Asp Ser Gly Glu Tyr Phe Cys Leu Ala Ser Asn
305                 310                 315                 320

Lys Met Gly Ser Ile Arg His Thr Ile Ser Val Arg Val Lys Ala Ala
                325                 330                 335

Pro Tyr Trp Leu Asp Glu Pro Lys Asn Leu Ile Leu Ala Pro Gly Glu
            340                 345                 350

Asp Gly Arg Leu Val Cys Arg Ala Asn Gly Asn Pro Lys Pro Thr Val
        355                 360                 365

Gln Trp Met Val Asn Gly Glu Pro Leu Gln Ser Ala Pro Pro Asn Pro
    370                 375                 380

Asn Arg Glu Val Ala Gly Asp Thr Ile Ile Phe Arg Asp Thr Gln Ile
385                 390                 395                 400

Ser Ser Arg Ala Val Tyr Gln Cys Asn Thr Ser Asn Glu His Gly Tyr
                405                 410                 415

Leu Leu Ala Asn Ala Phe Val Ser Val Leu Asp Val Pro Pro Arg Met
            420                 425                 430

Leu Ser Pro Arg Asn Gln Leu Ile Arg Val Ile Leu Tyr Asn Arg Thr
        435                 440                 445

Arg Leu Asp Cys Pro Phe Phe Gly Ser Pro Ile Pro Thr Leu Arg Trp
    450                 455                 460

Phe Lys Asn Gly Gln Gly Ser Asn Leu Asp Gly Gly Asn Tyr His Val
465                 470                 475                 480

Tyr Glu Asn Gly Ser Leu Glu Ile Lys Met Ile Arg Lys Glu Asp Gln
                485                 490                 495

Gly Ile Tyr Thr Cys Val Ala Thr Asn Ile Leu Gly Lys Ala Glu Asn
            500                 505                 510

Gln Val Arg Leu Glu Val Lys Asp Pro Thr Arg Ile Tyr Arg Met Pro
        515                 520                 525

Glu Asp Gln Val Ala Arg Arg Gly Thr Thr Val Gln Leu Glu Cys Arg
    530                 535                 540

Val Lys His Asp Pro Ser Leu Lys Leu Thr Val Ser Trp Leu Lys Asp
545                 550                 555                 560

Asp Glu Pro Leu Tyr Ile Gly Asn Arg Met Lys Lys Glu Asp Asp Ser
                565                 570                 575

Leu Thr Ile Phe Gly Val Ala Glu Arg Asp Gln Gly Ser Tyr Thr Cys
            580                 585                 590

Val Ala Ser Thr Glu Leu Asp Gln Asp Leu Ala Lys Ala Tyr Leu Thr
```

-continued

```
            595                 600                 605
Val Leu Ala Asp Gln Ala Thr Pro Thr Asn Arg Leu Ala Ala Leu Pro
610                 615                 620

Lys Gly Arg Pro Asp Arg Pro Arg Asp Leu Glu Leu Thr Asp Leu Ala
625                 630                 635                 640

Glu Arg Ser Val Arg Leu Thr Trp Ile Pro Gly Asp Ala Asn Asn Ser
                    645                 650                 655

Pro Ile Thr Asp Tyr Val Val Gln Phe Glu Glu Asp Gln Phe Gln Pro
                660                 665                 670

Gly Val Trp His Asp His Ser Lys Tyr Pro Gly Ser Val Asn Ser Ala
            675                 680                 685

Val Leu Arg Leu Ser Pro Tyr Val Asn Tyr Gln Phe Arg Val Ile Ala
        690                 695                 700

Ile Asn Glu Val Gly Ser Ser His Pro Ser Leu Pro Ser Glu Arg Tyr
705                 710                 715                 720

Arg Thr Ser Gly Ala Pro Pro Glu Ser Asn Pro Gly Asp Val Lys Gly
                    725                 730                 735

Glu Gly Thr Arg Lys Asn Asn Met Glu Ile Thr Trp Thr Pro Met Asn
                740                 745                 750

Ala Thr Ser Ala Phe Gly Pro Asn Leu Arg Tyr Ile Val Lys Trp Arg
            755                 760                 765

Arg Arg Glu Thr Arg Glu Ala Trp Asn Asn Val Thr Val Trp Gly Ser
770                 775                 780

Arg Tyr Val Val Gly Gln Thr Pro Val Tyr Val Pro Tyr Glu Ile Arg
785                 790                 795                 800

Val Gln Ala Glu Asn Asp Phe Gly Lys Gly Pro Glu Pro Glu Ser Val
                    805                 810                 815

Ile Gly Tyr Ser Gly Glu Asp Tyr Pro Arg Ala Ala Pro Thr Glu Val
                820                 825                 830

Lys Val Arg Val Met Asn Ser Thr Ala Ile Ser Leu Gln Trp Asn Arg
            835                 840                 845

Val Tyr Ser Asp Thr Val Gln Gly Gln Leu Arg Glu Tyr Arg Ala Tyr
        850                 855                 860

Tyr Trp Arg Glu Ser Ser Leu Leu Lys Asn Leu Trp Val Ser Gln Lys
865                 870                 875                 880

Arg Gln Gln Ala Ser Phe Pro Gly Asp Arg Leu Arg Gly Val Val Ser
                    885                 890                 895

Arg Leu Phe Pro Tyr Ser Asn Tyr Lys Leu Glu Met Val Val Val Asn
                900                 905                 910

Gly Arg Gly Asp Gly Pro Arg Ser Glu Thr Lys Glu Phe Thr Thr Pro
            915                 920                 925

Glu Gly Val Pro Ser Ala Pro Arg Arg Phe Arg Val Arg Gln Pro Asn
        930                 935                 940

Leu Glu Thr Ile Asn Leu Glu Trp Asp His Pro Glu His Pro Asn Gly
945                 950                 955                 960

Ile Met Ile Gly Tyr Thr Leu Lys Tyr Val Ala Phe Asn Gly Thr Lys
                    965                 970                 975

Val Gly Lys Gln Ile Val Glu Asn Phe Ser Pro Asn Gln Thr Lys Phe
                980                 985                 990

Thr Val Gln Arg Thr Asp Pro Val  Ser Arg Tyr Arg Phe  Thr Leu Ser
            995                 1000                1005

Ala Arg  Thr Gln Val Gly Ser  Gly Glu Ala Val Thr  Glu Glu Ser
    1010                1015                1020
```

```
Pro Ala Pro Pro Asn Glu Ala Thr Pro Thr Ala Ala Pro Pro Thr
        1025                1030                1035

Leu Pro Pro Thr Thr Val Gly Ala Thr Gly Ala Val Ser Ser Thr
        1040                1045                1050

Asp Ala Thr Ala Ile Ala Thr Thr Glu Ala Thr Val Pro
        1055                1060                1065

Ile Ile Pro Thr Val Ala Pro Thr Thr Ile Ala Thr Thr Thr Thr
        1070                1075                1080

Val Ala Thr Thr Thr Thr Thr Ala Ala Ala Thr Thr Thr Thr
        1085                1090                1095

Glu Ser Pro Pro Thr Thr Thr Ser Gly Thr Lys Ile His Glu Ser
        1100                1105                1110

Ala Pro Asp Glu Gln Ser Ile Trp Asn Val Thr Val Leu Pro Asn
        1115                1120                1125

Ser Lys Trp Ala Asn Ile Thr Trp Lys His Asn Phe Gly Pro Gly
        1130                1135                1140

Thr Asp Phe Val Val Glu Tyr Ile Asp Ser Asn His Thr Lys Lys
        1145                1150                1155

Thr Val Pro Val Lys Ala Gln Ala Gln Pro Ile Gln Leu Thr Asp
        1160                1165                1170

Leu Tyr Pro Gly Met Thr Tyr Thr Leu Arg Val Tyr Ser Arg Asp
        1175                1180                1185

Asn Glu Gly Ile Ser Ser Thr Val Ile Thr Phe Met Thr Ser Thr
        1190                1195                1200

Ala Tyr Thr Asn Asn Gln Ala Asp Ile Ala Thr Gln Gly Trp Phe
        1205                1210                1215

Ile Gly Leu Met Cys Ala Ile Ala Leu Leu Val Leu Ile Leu Leu
        1220                1225                1230

Ile Val Cys Phe Ile Lys Arg Ser Arg Gly Gly Lys Tyr Pro Val
        1235                1240                1245

Arg Glu Lys Lys Asp Val Pro Leu Gly Pro Glu Asp Pro Lys Glu
        1250                1255                1260

Glu Asp Gly Ser Phe Asp Tyr Ser Asp Glu Asp Asn Lys Pro Leu
        1265                1270                1275

Gln Gly Ser Gln Thr Ser Leu Asp Gly Thr Ile Lys Gln Gln Glu
        1280                1285                1290

Ser Asp Asp Ser Leu Val Asp Tyr Gly Glu Gly Glu Gly Gln
        1295                1300                1305

Phe Asn Glu Asp Gly Ser Phe Ile Gly Gln Tyr Thr Val Lys Lys
        1310                1315                1320

Asp Lys Glu Glu Thr Glu Gly Asn Glu Ser Ser Glu Ala Thr Ser
        1325                1330                1335

Pro Val Asn Ala Ile Tyr Ser Leu Ala
        1340                1345

<210> SEQ ID NO 10
<211> LENGTH: 1018
<212> TYPE: PRT
<213> ORGANISM: Homo sapiens

<400> SEQUENCE: 10

Met Lys Met Trp Leu Leu Val Ser His Leu Val Ile Ile Ser Ile Thr
1               5                   10                  15

Thr Cys Leu Ala Glu Phe Thr Trp Tyr Arg Arg Tyr Gly His Gly Val
```

```
                20                  25                  30
Ser Glu Glu Asp Lys Gly Phe Gly Pro Ile Phe Glu Glu Gln Pro Ile
                35                  40                  45
Asn Thr Ile Tyr Pro Glu Glu Ser Leu Glu Gly Lys Val Ser Leu Asn
                50                  55                  60
Cys Arg Ala Arg Ala Ser Pro Phe Pro Val Tyr Lys Trp Arg Met Asn
65                  70                  75                  80
Asn Gly Asp Val Asp Leu Thr Ser Asp Arg Tyr Ser Met Val Gly Gly
                85                  90                  95
Asn Leu Val Ile Asn Asn Pro Asp Lys Gln Lys Asp Ala Gly Ile Tyr
                100                 105                 110
Tyr Cys Leu Ala Ser Asn Asn Tyr Gly Met Val Arg Ser Thr Glu Ala
                115                 120                 125
Thr Leu Ser Phe Gly Tyr Leu Asp Pro Phe Pro Pro Glu Glu Arg Pro
                130                 135                 140
Glu Val Arg Val Lys Glu Gly Lys Gly Met Val Leu Leu Cys Asp Pro
145                 150                 155                 160
Pro Tyr His Phe Pro Asp Asp Leu Ser Tyr Arg Trp Leu Leu Asn Glu
                165                 170                 175
Phe Pro Val Phe Ile Thr Met Asp Lys Arg Arg Phe Val Ser Gln Thr
                180                 185                 190
Asn Gly Asn Leu Tyr Ile Ala Asn Val Glu Ala Ser Asp Lys Gly Asn
                195                 200                 205
Tyr Ser Cys Phe Val Ser Ser Pro Ser Ile Thr Lys Ser Val Phe Ser
                210                 215                 220
Lys Phe Ile Pro Leu Ile Pro Ile Pro Glu Arg Thr Thr Lys Pro Tyr
225                 230                 235                 240
Pro Ala Asp Ile Val Val Gln Phe Lys Asp Val Tyr Ala Leu Met Gly
                245                 250                 255
Gln Asn Val Thr Leu Glu Cys Phe Ala Leu Gly Asn Pro Val Pro Asp
                260                 265                 270
Ile Arg Trp Arg Lys Val Leu Glu Pro Met Pro Ser Thr Ala Glu Ile
                275                 280                 285
Ser Thr Ser Gly Ala Val Leu Lys Ile Phe Asn Ile Gln Leu Glu Asp
                290                 295                 300
Glu Gly Ile Tyr Glu Cys Glu Ala Glu Asn Ile Arg Gly Lys Asp Lys
305                 310                 315                 320
His Gln Ala Arg Ile Tyr Val Gln Ala Phe Pro Glu Trp Val Glu His
                325                 330                 335
Ile Asn Asp Thr Glu Val Asp Ile Gly Ser Asp Leu Tyr Trp Pro Cys
                340                 345                 350
Val Ala Thr Gly Lys Pro Ile Pro Thr Ile Arg Trp Leu Lys Asn Gly
                355                 360                 365
Tyr Ala Tyr His Lys Gly Glu Leu Arg Leu Tyr Asp Val Thr Phe Glu
                370                 375                 380
Asn Ala Gly Met Tyr Gln Cys Ile Ala Glu Asn Thr Tyr Gly Ala Ile
385                 390                 395                 400
Tyr Ala Asn Ala Glu Leu Lys Ile Leu Ala Leu Ala Pro Thr Phe Glu
                405                 410                 415
Met Asn Pro Met Lys Lys Lys Ile Leu Ala Ala Lys Gly Gly Arg Val
                420                 425                 430
Ile Ile Glu Cys Lys Pro Lys Ala Ala Pro Lys Pro Lys Phe Ser Trp
                435                 440                 445
```

```
Ser Lys Gly Thr Glu Trp Leu Val Asn Ser Ser Arg Ile Leu Ile Trp
450                 455                 460
Glu Asp Gly Ser Leu Glu Ile Asn Asn Ile Thr Arg Asn Asp Gly Gly
465                 470                 475                 480
Ile Tyr Thr Cys Phe Ala Glu Asn Asn Arg Gly Lys Ala Asn Ser Thr
                485                 490                 495
Gly Thr Leu Val Ile Thr Asp Pro Thr Arg Ile Ile Leu Ala Pro Ile
                500                 505                 510
Asn Ala Asp Ile Thr Val Gly Glu Asn Ala Thr Met Gln Cys Ala Ala
                515                 520                 525
Ser Phe Asp Pro Ala Leu Asp Leu Thr Phe Val Trp Ser Phe Asn Gly
530                 535                 540
Tyr Val Ile Asp Phe Asn Lys Glu Asn Ile His Tyr Gln Arg Asn Phe
545                 550                 555                 560
Met Leu Asp Ser Asn Gly Glu Leu Leu Ile Arg Asn Ala Gln Leu Lys
                565                 570                 575
His Ala Gly Arg Tyr Thr Cys Thr Ala Gln Thr Ile Val Asp Asn Ser
                580                 585                 590
Ser Ala Ser Ala Asp Leu Val Val Arg Gly Pro Pro Gly Pro Pro Gly
                595                 600                 605
Gly Leu Arg Ile Glu Asp Ile Arg Ala Thr Ser Val Ala Leu Thr Trp
610                 615                 620
Ser Arg Gly Ser Asp Asn His Ser Pro Ile Ser Lys Tyr Thr Ile Gln
625                 630                 635                 640
Thr Lys Thr Ile Leu Ser Asp Asp Trp Lys Asp Ala Lys Thr Asp Pro
                645                 650                 655
Pro Ile Ile Glu Gly Asn Met Glu Ala Ala Arg Ala Val Asp Leu Ile
                660                 665                 670
Pro Trp Met Glu Tyr Glu Phe Arg Val Val Ala Thr Asn Thr Leu Gly
                675                 680                 685
Arg Gly Glu Pro Ser Ile Pro Ser Asn Arg Ile Lys Thr Asp Gly Ala
690                 695                 700
Ala Pro Asn Val Ala Pro Ser Asp Val Gly Gly Gly Gly Gly Arg Asn
705                 710                 715                 720
Arg Glu Leu Thr Ile Thr Trp Ala Pro Leu Ser Arg Glu Tyr His Tyr
                725                 730                 735
Gly Asn Asn Phe Gly Tyr Ile Val Ala Phe Lys Pro Phe Asp Gly Glu
                740                 745                 750
Glu Trp Lys Lys Val Thr Val Thr Asn Pro Asp Thr Gly Arg Tyr Val
                755                 760                 765
His Lys Asp Glu Thr Met Ser Pro Ser Thr Ala Phe Gln Val Lys Val
770                 775                 780
Lys Ala Phe Asn Asn Lys Gly Asp Gly Pro Tyr Ser Leu Leu Ala Val
785                 790                 795                 800
Ile Asn Ser Ala Gln Asp Ala Pro Ser Glu Ala Pro Thr Glu Val Gly
                805                 810                 815
Val Lys Val Leu Ser Ser Ser Glu Ile Ser Val His Trp Glu His Val
                820                 825                 830
Leu Glu Lys Ile Val Glu Ser Tyr Gln Ile Arg Tyr Trp Ala Ala His
                835                 840                 845
Asp Lys Glu Glu Ala Ala Asn Arg Val Gln Val Thr Ser Gln Glu Tyr
850                 855                 860
```

-continued

Ser Ala Arg Leu Glu Asn Leu Leu Pro Asp Thr Gln Tyr Phe Ile Glu
865                 870                 875                 880

Val Gly Ala Cys Asn Ser Ala Gly Cys Gly Pro Pro Ser Asp Met Ile
            885                 890                 895

Glu Ala Phe Thr Lys Lys Ala Pro Pro Ser Gln Pro Pro Arg Ile Ile
            900                 905                 910

Ser Ser Val Arg Ser Gly Ser Arg Tyr Ile Ile Thr Trp Asp His Val
            915                 920                 925

Val Ala Leu Ser Asn Glu Ser Thr Val Thr Gly Tyr Lys Val Leu Tyr
            930                 935                 940

Arg Pro Asp Gly Gln His Asp Gly Lys Leu Tyr Ser Thr His Lys His
945                 950                 955                 960

Ser Ile Glu Val Pro Ile Pro Arg Asp Gly Glu Tyr Val Val Glu Val
            965                 970                 975

Arg Ala His Ser Asp Gly Gly Asp Gly Val Val Ser Gln Val Lys Ile
            980                 985                 990

Ser Gly Ala Pro Thr Leu Ser Pro  Ser Leu Leu Gly Leu Leu Leu Pro
            995                 1000                1005

Ala Phe Gly Ile Leu Val Tyr  Leu Glu Phe
    1010                1015

<210> SEQ ID NO 11
<211> LENGTH: 379
<212> TYPE: PRT
<213> ORGANISM: Homo sapiens

<400> SEQUENCE: 11

Met Thr Ser Val Ala Lys Val Tyr Tyr Ser Gln Thr Gln Thr Glu
1               5                   10                  15

Ser Arg Pro Leu Met Gly Pro Gly Ile Arg Arg Arg Val Leu Thr
                20                  25                  30

Lys Asp Gly Arg Ser Asn Val Arg Met Glu His Ile Ala Asp Lys Arg
            35                  40                  45

Phe Pro Tyr Leu Lys Asp Leu Trp Thr Thr Phe Ile Asp Met Gln Trp
50                  55                  60

Arg Tyr Lys Leu Leu Leu Phe Ser Ala Thr Phe Ala Gly Thr Trp Phe
65                  70                  75                  80

Leu Phe Gly Val Val Trp Tyr Leu Val Ala Val Ala His Gly Asp Leu
                85                  90                  95

Leu Glu Leu Asp Pro Pro Ala Asn His Thr Pro Cys Val Val Gln Val
            100                 105                 110

His Thr Leu Thr Gly Ala Phe Leu Phe Ser Leu Glu Ser Gln Thr Thr
            115                 120                 125

Ile Gly Tyr Gly Phe Arg Tyr Ile Ser Glu Glu Cys Pro Leu Ala Ile
            130                 135                 140

Val Leu Leu Ile Ala Gln Leu Val Leu Thr Thr Ile Leu Glu Ile Phe
145                 150                 155                 160

Ile Thr Gly Thr Phe Gln Ala Lys Ile Ala Arg Pro Lys Lys Arg Ala
                165                 170                 175

Glu Thr Ile Arg Phe Ser Gln His Ala Val Val Ala Ser His Asn Gly
            180                 185                 190

Lys Pro Cys Leu Met Ile Arg Val Ala Asn Met Arg Lys Ser Leu Leu
            195                 200                 205

Ile Gly Cys Gln Val Thr Gly Lys Leu Leu Gln Thr His Gln Thr Lys
            210                 215                 220

```
Glu Gly Glu Asn Ile Arg Leu Asn Gln Val Asn Val Thr Phe Gln Val
225                 230                 235                 240

Asp Thr Ala Ser Asp Ser Pro Phe Leu Ile Leu Pro Leu Thr Phe Tyr
            245                 250                 255

His Val Val Asp Glu Thr Ser Pro Leu Lys Asp Leu Pro Leu Cys Ser
        260                 265                 270

Gly Glu Gly Asp Phe Glu Leu Val Leu Ile Leu Ser Gly Thr Val Glu
            275                 280                 285

Ser Thr Ser Ala Thr Cys Gln Val Arg Thr Ser Tyr Leu Pro Glu Glu
        290                 295                 300

Ile Leu Trp Gly Tyr Glu Phe Thr Pro Ala Ile Ser Leu Ser Ala Ser
305                 310                 315                 320

Gly Lys Tyr Ile Ala Asp Phe Ser Leu Phe Asp Gln Val Val Lys Val
            325                 330                 335

Ala Ser Pro Ser Gly Leu Arg Asp Ser Thr Val Arg Tyr Gly Asp Pro
        340                 345                 350

Glu Lys Leu Lys Leu Glu Glu Ser Leu Arg Glu Gln Ala Glu Lys Glu
            355                 360                 365

Gly Ser Ala Leu Ser Val Arg Ile Ser Asn Val
        370                 375

<210> SEQ ID NO 12
<211> LENGTH: 20
<212> TYPE: PRT
<213> ORGANISM: Homo sapiens

<400> SEQUENCE: 12

Lys Tyr Leu Ala Thr Ala Ser Thr Met Asp His Ala Arg His Gly Phe
1               5                   10                  15

Leu Pro Arg His
            20

<210> SEQ ID NO 13
<211> LENGTH: 17
<212> TYPE: PRT
<213> ORGANISM: Homo sapiens

<400> SEQUENCE: 13

Glu Asn Pro Val Val His Phe Phe Lys Asn Ile Val Thr Pro Arg Thr
1               5                   10                  15

Pro

<210> SEQ ID NO 14
<211> LENGTH: 19
<212> TYPE: PRT
<213> ORGANISM: Homo sapiens

<400> SEQUENCE: 14

Leu Ser Arg Phe Ser Trp Gly Ala Glu Gly Gln Arg Pro Gly Phe Gly
1               5                   10                  15

Tyr Gly Gly

<210> SEQ ID NO 15
<211> LENGTH: 25
<212> TYPE: PRT
<213> ORGANISM: Homo sapiens

<400> SEQUENCE: 15
```

Ala Ser Asp Tyr Lys Ser Ala His Lys Gly Leu Lys Gly Val Asp Ala
1               5                   10                  15

Gln Gly Thr Leu Ser Lys Ile Phe Lys
            20                  25

<210> SEQ ID NO 16
<211> LENGTH: 25
<212> TYPE: PRT
<213> ORGANISM: Homo sapiens

<400> SEQUENCE: 16

Ala Gln Gly Thr Leu Ser Lys Ile Phe Lys Leu Gly Gly Arg Asp Ser
1               5                   10                  15

Arg Ser Gly Ser Pro Met Ala Arg Arg
            20                  25

<210> SEQ ID NO 17
<211> LENGTH: 21
<212> TYPE: PRT
<213> ORGANISM: Homo sapiens

<400> SEQUENCE: 17

Thr Gly Thr Glu Lys Leu Ile Glu Thr Tyr Phe Ser Lys Asn Tyr Gln
1               5                   10                  15

Asp Tyr Glu Tyr Leu
            20

<210> SEQ ID NO 18
<211> LENGTH: 18
<212> TYPE: PRT
<213> ORGANISM: Homo sapiens

<400> SEQUENCE: 18

Gly Phe Tyr Thr Thr Gly Ala Val Arg Gln Ile Phe Gly Asp Tyr Lys
1               5                   10                  15

Thr Thr

<210> SEQ ID NO 19
<211> LENGTH: 16
<212> TYPE: PRT
<213> ORGANISM: Homo sapiens

<400> SEQUENCE: 19

His Cys Leu Gly Lys Trp Leu Gly His Pro Asp Lys Phe Val Gly Ile
1               5                   10                  15

<210> SEQ ID NO 20
<211> LENGTH: 20
<212> TYPE: PRT
<213> ORGANISM: Homo sapiens

<400> SEQUENCE: 20

Asn Thr Trp Thr Thr Cys Gln Ser Ile Ala Phe Pro Ser Lys Thr Ser
1               5                   10                  15

Ala Ser Ile Gly
            20

<210> SEQ ID NO 21
<211> LENGTH: 21
<212> TYPE: PRT
<213> ORGANISM: Homo sapiens

<400> SEQUENCE: 21

```
Ser Lys Thr Ser Ala Ser Ile Gly Ser Leu Cys Ala Asp Ala Arg Met
 1               5                  10                  15

Tyr Gly Val Leu Pro
            20

<210> SEQ ID NO 22
<211> LENGTH: 20
<212> TYPE: PRT
<213> ORGANISM: Homo sapiens

<400> SEQUENCE: 22

Gly Gln Phe Arg Val Ile Gly Pro Arg His Pro Ile Arg Ala Leu Val
 1               5                  10                  15

Gly Asp Glu Val
            20

<210> SEQ ID NO 23
<211> LENGTH: 20
<212> TYPE: PRT
<213> ORGANISM: Homo sapiens

<400> SEQUENCE: 23

Pro Ile Arg Ala Leu Val Gly Asp Glu Val Glu Leu Pro Cys Arg Ile
 1               5                  10                  15

Ser Pro Gly Lys
            20

<210> SEQ ID NO 24
<211> LENGTH: 21
<212> TYPE: PRT
<213> ORGANISM: Homo sapiens

<400> SEQUENCE: 24

Met Glu Val Gly Trp Tyr Arg Pro Pro Phe Ser Arg Val Val His Leu
 1               5                  10                  15

Tyr Arg Asn Gly Lys
            20

<210> SEQ ID NO 25
<211> LENGTH: 31
<212> TYPE: PRT
<213> ORGANISM: Homo sapiens

<400> SEQUENCE: 25

Glu Val Gly Glu Leu Ser Arg Gly Lys Leu Tyr Ser Leu Gly Asn Gly
 1               5                  10                  15

Arg Trp Met Leu Thr Leu Ala Lys Asn Met Glu Val Arg Ala Ile
            20                  25                  30

<210> SEQ ID NO 26
<211> LENGTH: 33
<212> TYPE: PRT
<213> ORGANISM: Homo sapiens

<400> SEQUENCE: 26

Gly Asn Gly Arg Trp Met Leu Thr Leu Ala Lys Asn Met Glu Val Arg
 1               5                  10                  15

Ala Ile Phe Thr Gly Tyr Tyr Gly Lys Gly Lys Pro Val Pro Thr Gln
            20                  25                  30

Gly
```